US010226642B2

(12) United States Patent
Rabiner et al.

(10) Patent No.: US 10,226,642 B2
(45) Date of Patent: Mar. 12, 2019

(54) SYSTEMS AND METHODS FOR ANTI-MICROBIAL EFFECT FOR BONES

(71) Applicant: IlluminOss Medical, Inc., East Providence, RI (US)

(72) Inventors: Robert A. Rabiner, Barrington, RI (US); Daniel E. Rabiner, Chelsea, MA (US); Gene P. DiPoto, Upton, MA (US); Augustus C. Shanahan, Newton, MA (US); Franklin D. Shuler, Huntington, WV (US)

(73) Assignee: IlluminOss Medical, Inc., East Providence, RI (US)

( * ) Notice: Subject to any disclaimer, the term of this patent is extended or adjusted under 35 U.S.C. 154(b) by 35 days.

(21) Appl. No.: 15/343,738

(22) Filed: Nov. 4, 2016

(65) Prior Publication Data
US 2017/0128742 A1 May 11, 2017

Related U.S. Application Data

(60) Provisional application No. 62/252,275, filed on Nov. 6, 2015, provisional application No. 62/272,420, filed on Dec. 29, 2015.

(51) Int. Cl.
A61B 17/70 (2006.01)
A61B 17/88 (2006.01)
(Continued)

(52) U.S. Cl.
CPC .......... *A61N 5/0624* (2013.01); *A61M 25/10* (2013.01); *A61N 5/0601* (2013.01); *A61N 5/062* (2013.01);
(Continued)

(58) Field of Classification Search
CPC .................................................... A61M 25/10
See application file for complete search history.

(56) References Cited

U.S. PATENT DOCUMENTS 5,445,608 A  8/1995  Chen et al.
5,930,424 A  7/1999  Heimberger et al.
(Continued)

OTHER PUBLICATIONS

PCT International Search Report based on PCT/US2016/60603 dated Jan. 30, 2017.

*Primary Examiner* — Zade Coley
(74) *Attorney, Agent, or Firm* — Greenberg Traurig, LLP; David J. Dykeman; Roman Fayerberg

(57) ABSTRACT

Systems and methods for restructure and stabilization of bones that provide an anti-microbial effect are disclosed herein. A device includes a delivery catheter having an inner void for passing at least one light sensitive liquid, and an inner lumen; an expandable member releasably engaging the distal end of the delivery catheter; at least one channel positioned in the expandable member; and a light conducting fiber sized to pass through the inner lumen of the delivery catheter and into the expandable member, wherein, when the light conducting fiber is in the at least one channel, the light conducting fiber is able to disperse light energy to provide an anti-microbial effect. When the light conducting fiber is in the expandable member, the light conducting fiber is able to disperse the light energy to initiate hardening of the light sensitive liquid within the expandable member to form a photodynamic implant.

11 Claims, 40 Drawing Sheets

(51) Int. Cl.
  *A61N 5/06*   (2006.01)
  *A61M 25/10*  (2013.01)

(52) U.S. Cl.
  CPC .... *A61M 2210/02* (2013.01); *A61N 2005/063* (2013.01)

(56) References Cited

U.S. PATENT DOCUMENTS

| | | | |
|---|---|---|---|
| 7,806,900 B2 | 10/2010 | Rabiner | |
| 7,811,284 B2 | 10/2010 | Rabiner | |
| 7,811,290 B2 | 10/2010 | Rabiner | |
| 7,842,040 B2 | 11/2010 | Rabiner et al. | |
| 7,843,328 B2 | 11/2010 | Redmond et al. | |
| 7,879,041 B2 | 2/2011 | Rabiner et al. | |
| 8,012,157 B2 | 9/2011 | Chang et al. | |
| 8,210,729 B2 | 7/2012 | O'Leary et al. | |
| 8,226,659 B2 | 7/2012 | Rabiner et al. | |
| 8,246,628 B2 | 8/2012 | Rabiner | |
| 8,308,749 B2 * | 11/2012 | Johnson .................. A61F 2/856 606/192 | |
| 8,328,402 B2 | 12/2012 | O'Leary et al. | |
| 8,348,956 B2 | 1/2013 | Rabiner | |
| 8,366,711 B2 | 2/2013 | Rabiner et al. | |
| 8,403,968 B2 | 3/2013 | Rabiner et al. | |
| 8,431,074 B2 | 4/2013 | Neer | |
| 8,475,732 B2 | 7/2013 | Simmons et al. | |
| 8,512,338 B2 | 8/2013 | Rabiner et al. | |
| 8,523,901 B2 | 9/2013 | Rabiner et al. | |
| 8,574,233 B2 | 11/2013 | Rabiner et al. | |
| 8,668,701 B2 | 3/2014 | Rabiner et al. | |
| 8,672,982 B2 | 3/2014 | Rabiner et al. | |
| 8,684,965 B2 | 4/2014 | Rabiner et al. | |
| 8,734,460 B2 | 5/2014 | Rabiner et al. | |
| 8,777,950 B2 | 7/2014 | Colleran et al. | |
| 8,870,965 B2 | 10/2014 | Rabiner et al. | |
| 8,906,030 B2 | 12/2014 | Rabiner et al. | |
| 8,906,031 B2 | 12/2014 | Rabiner et al. | |
| 8,915,966 B2 | 12/2014 | Rabiner et al. | |
| 8,936,382 B2 | 1/2015 | O'Leary et al. | |
| 8,936,644 B2 | 1/2015 | Rabiner et al. | |
| 8,939,977 B2 | 1/2015 | DiPoto et al. | |
| 9,005,254 B2 | 4/2015 | Rabiner et al. | |
| 9,050,079 B2 | 6/2015 | Rabiner et al. | |
| 9,101,419 B2 | 8/2015 | Colleran et al. | |
| 9,125,706 B2 | 9/2015 | Rabiner et al. | |
| 9,144,442 B2 | 9/2015 | Rabiner et al. | |
| 9,179,959 B2 * | 11/2015 | Rabiner .............. A61B 17/7097 | |
| 9,216,049 B2 | 12/2015 | Rabiner et al. | |
| 9,254,156 B2 | 2/2016 | Rabiner | |
| 9,254,195 B2 | 2/2016 | Rabiner et al. | |
| 9,265,549 B2 | 2/2016 | Rabiner | |
| 9,427,289 B2 | 8/2016 | Rabiner et al. | |
| 9,433,450 B2 | 9/2016 | Rabiner et al. | |
| 2001/0055462 A1 | 12/2001 | Seibel | |
| 2002/0091424 A1 | 7/2002 | Biel | |
| 2003/0055483 A1 * | 3/2003 | Gumm .................. A61F 2/856 623/1.11 | |
| 2005/0101854 A1 | 5/2005 | Larson et al. | |
| 2006/0100547 A1 | 5/2006 | Rabiner et al. | |
| 2007/0255287 A1 | 11/2007 | Rabiner | |
| 2008/0039854 A1 * | 2/2008 | Rabiner .............. A61B 17/7275 606/92 | |
| 2008/0125784 A1 | 5/2008 | Rabiner et al. | |
| 2009/0048629 A1 | 2/2009 | Rabiner | |
| 2009/0054900 A1 | 2/2009 | Rabiner et al. | |
| 2009/0112196 A1 | 4/2009 | Rabiner et al. | |
| 2009/0171358 A1 | 7/2009 | Chang et al. | |
| 2009/0177204 A1 | 7/2009 | Colleran et al. | |
| 2009/0187192 A1 | 7/2009 | Rabiner et al. | |
| 2010/0256641 A1 | 10/2010 | Rabiner et al. | |
| 2010/0262069 A1 | 10/2010 | Rabiner et al. | |
| 2010/0262188 A1 * | 10/2010 | Rabiner .............. A61B 17/7004 606/249 | |
| 2010/0265733 A1 | 10/2010 | O'Leary et al. | |
| 2010/0331850 A1 | 12/2010 | Rabiner | |
| 2011/0004213 A1 | 1/2011 | Rabiner et al. | |
| 2011/0009871 A1 | 1/2011 | Rabiner | |
| 2011/0046746 A1 * | 2/2011 | Rabiner ................ A61B 17/56 623/23.5 | |
| 2011/0098713 A1 | 4/2011 | Rabiner et al. | |
| 2011/0213339 A1 | 9/2011 | Bak | |
| 2011/0313356 A1 | 12/2011 | Rabiner et al. | |
| 2012/0065643 A1 | 3/2012 | Rabiner et al. | |
| 2012/0100601 A1 | 4/2012 | Simmons et al. | |
| 2012/0150190 A1 | 6/2012 | Rabiner | |
| 2012/0165941 A1 * | 6/2012 | Rabiner .............. A61B 17/7097 623/17.12 | |
| 2012/0262939 A1 | 10/2012 | O'Leary et al. | |
| 2012/0289968 A1 | 11/2012 | Rabiner | |
| 2013/0003406 A1 | 1/2013 | O'Leary et al. | |
| 2013/0006304 A1 | 1/2013 | Rabiner et al. | |
| 2013/0013008 A1 | 1/2013 | Rabiner et al. | |
| 2013/0013009 A1 | 1/2013 | Colleran et al. | |
| 2013/0013010 A1 | 1/2013 | Rabiner et al. | |
| 2013/0023876 A1 | 1/2013 | Rabiner et al. | |
| 2013/0023877 A1 | 1/2013 | Rabiner et al. | |
| 2013/0023886 A1 | 1/2013 | Rabiner et al. | |
| 2013/0041472 A1 | 2/2013 | Rabiner et al. | |
| 2013/0046390 A1 | 2/2013 | Rabiner et al. | |
| 2013/0066326 A1 | 3/2013 | Rabiner et al. | |
| 2013/0158607 A1 | 6/2013 | Rabiner et al. | |
| 2013/0184715 A1 | 7/2013 | Rabiner et al. | |
| 2013/0310875 A1 | 11/2013 | Rabiner et al. | |
| 2013/0323120 A1 | 12/2013 | Ma | |
| 2014/0018806 A1 | 1/2014 | DiPoto et al. | |
| 2014/0135847 A1 | 5/2014 | Rabiner et al. | |
| 2014/0142581 A1 | 5/2014 | Rabiner et al. | |
| 2014/0148813 A1 | 5/2014 | Rabiner et al. | |
| 2014/0163453 A1 | 6/2014 | Rabiner et al. | |
| 2014/0180288 A1 | 6/2014 | Rabiner et al. | |
| 2015/0066028 A1 | 3/2015 | Rabiner et al. | |
| 2015/0066085 A1 | 3/2015 | Rabiner et al. | |
| 2015/0080900 A1 | 3/2015 | Rabiner et al. | |
| 2015/0088268 A1 | 3/2015 | Rabiner et al. | |
| 2015/0374498 A1 | 12/2015 | Rabiner et al. | |
| 2016/0022333 A1 | 1/2016 | Rabiner et al. | |
| 2016/0128750 A1 | 5/2016 | Rabiner et al. | |
| 2016/0128836 A1 | 5/2016 | Rabiner et al. | |

\* cited by examiner

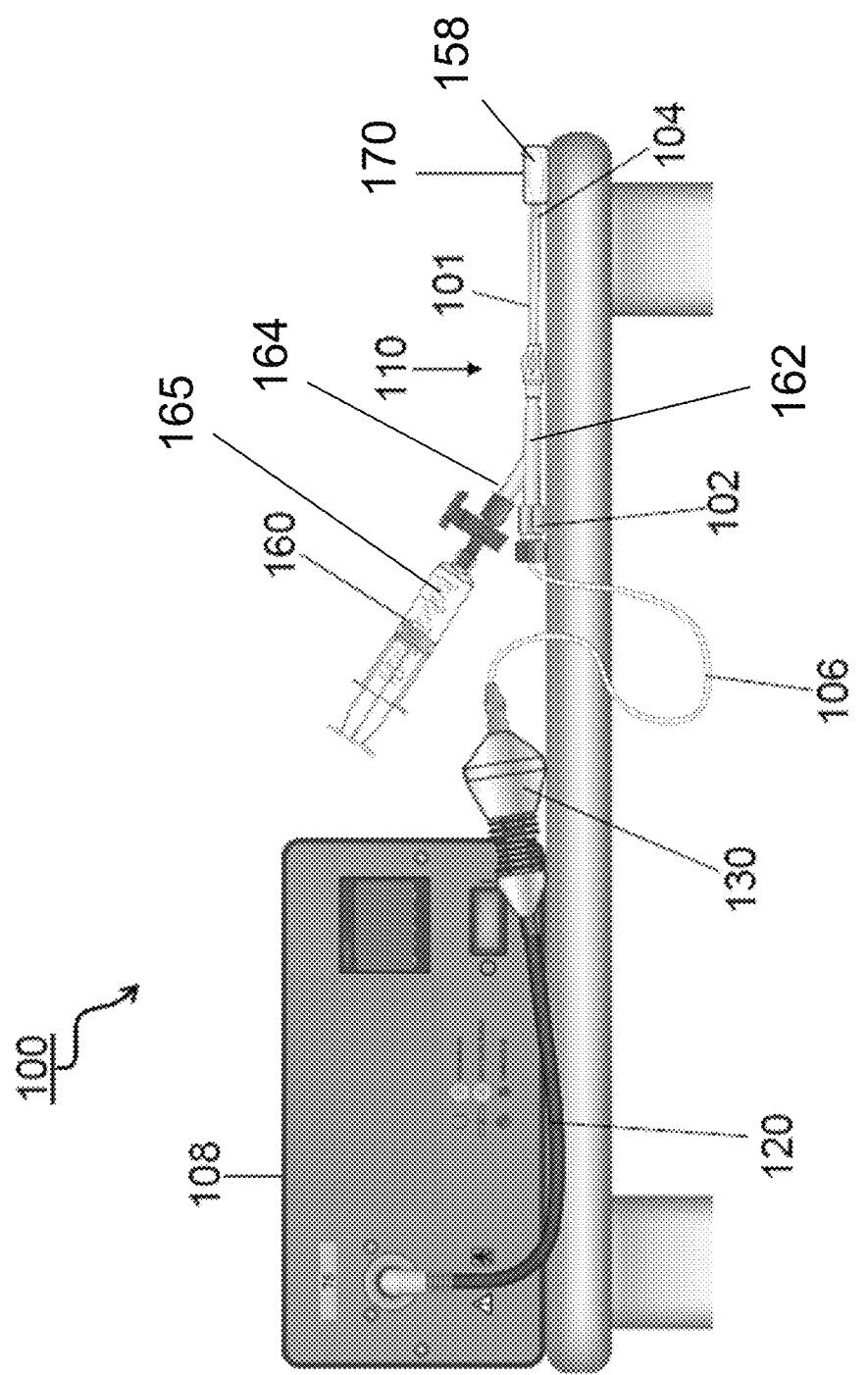

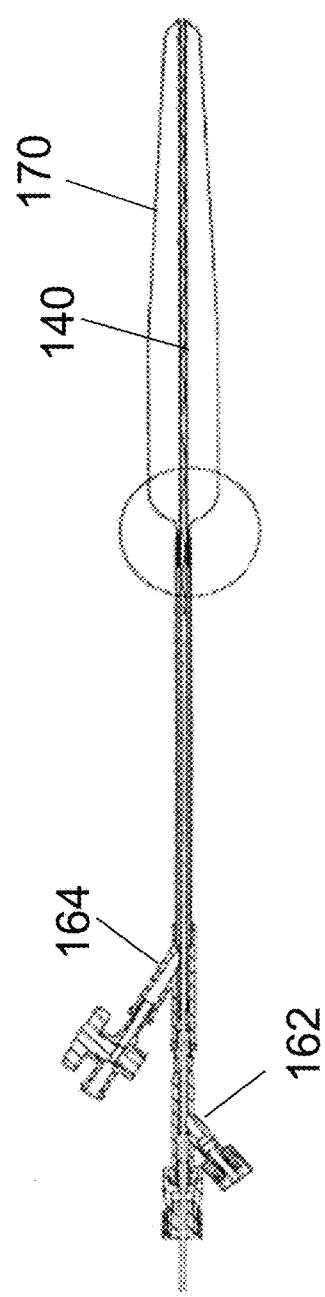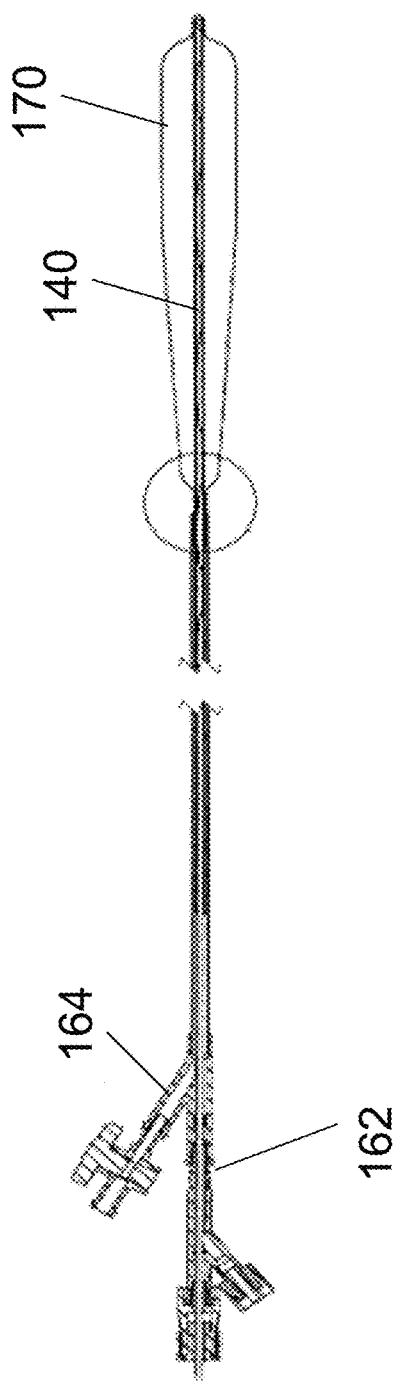

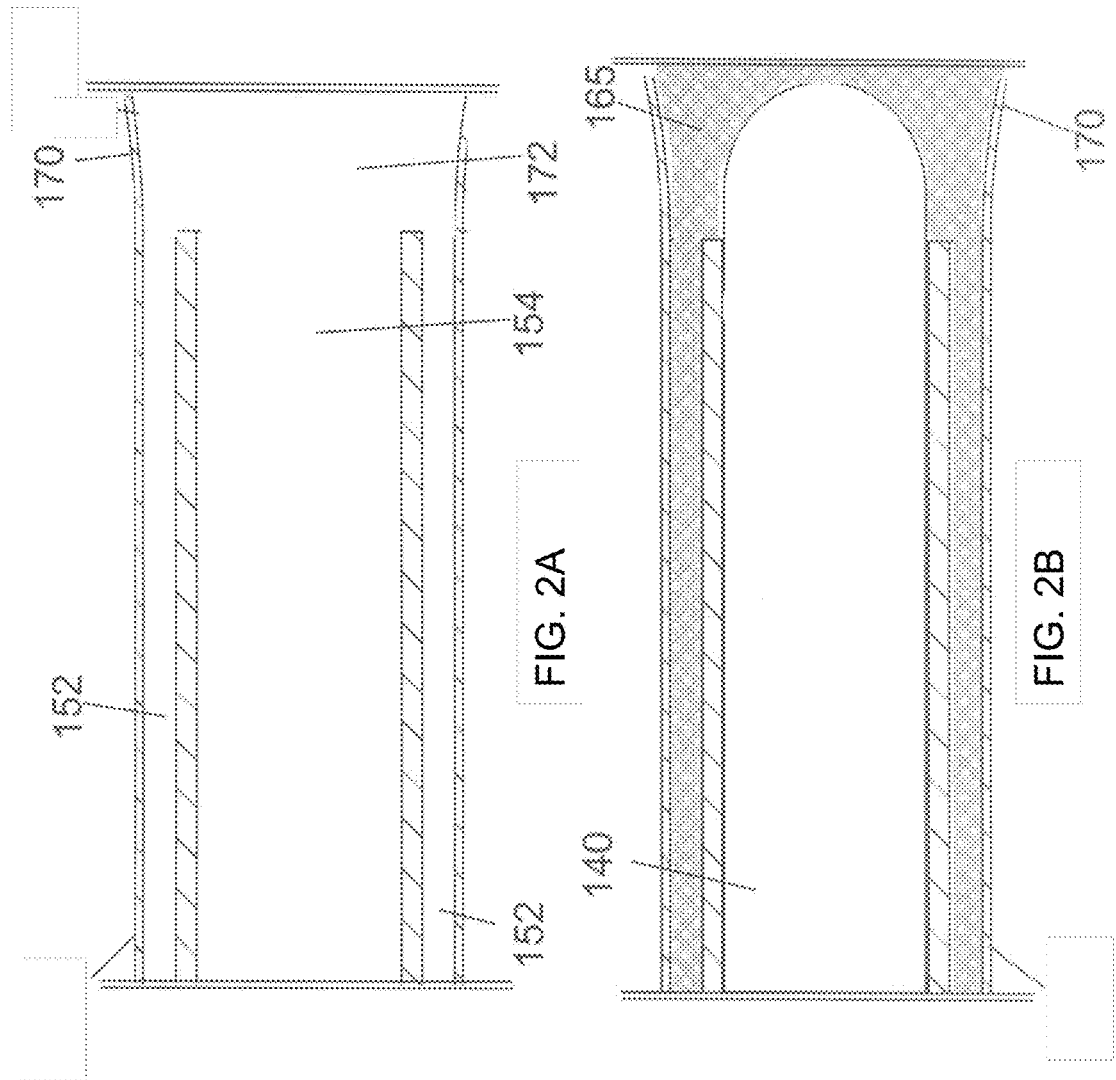

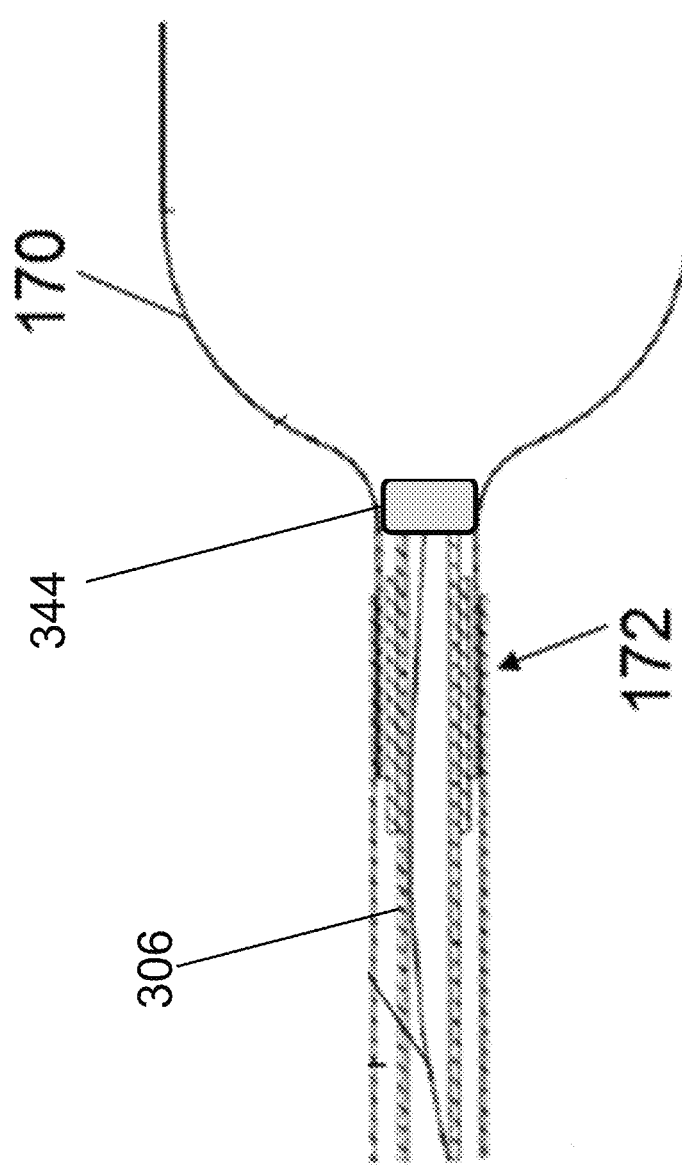

Studies on the in vitro antimicrobial effect of blue light

| Light Source | Radiant exposure | Bacterial species/strains | Inactivation efficacy | Ref |
|---|---|---|---|---|
| 405-nm diode laser | 20 J/cm² | H. pylori | >99.9% | 222 |
| 405 nm light-emitting diode | 15 J/cm² at lamp aperture | P. gingivalis | >75% | 223 |
| 380-520 nm broadband light | 4.2–42 J/cm² | P. gingivalis, P. intermedia, P. nigrescens, P. melaninogenica, S. constellatus | P. intermedia and P. nigrescens >5 log10 at 4.2 J/cm²; P. melaninogenica >5 log10 at 21 J/cm²; P. gingivalis 1.83 log10 at 42 J/cm² | 228 |
| 400–500 nm blue lamps | 200 and 1300 mW/cm² for up to 3 min | P. gingivalis, F. nucleatum, S. mutans, E. faecalis | The minimal inhibitory dose for P. gingivalis and F. nucleatum was 16-62 J/cm², for S. mutans and E. faecalis was 159-212 J/cm² | 229 |
| 405 and 470 nm light | 15 J/cm² | S. aureus, P. aeruginosa | S. aureus 90% at 405 nm, 62% at 470 nm, P. aeruginosa 95.1% at 405 nm, 96.5% at 470 nm | 230 |
| 407–420 nm | | five P. acnes strains | Decreased by 15.7% immediately and 24.4% at 60 min after the irradiation | 231 |
| 407–420 nm | 75 J/cm² | P. acnes | less than 2-log10 units (99%) illuminated once, decreased by 4-log10 units (99.99%) after two illuminations and by 5-log10 units (99.999%) after three illuminations | 231 |

FIG. 14G

SYSTEMS AND METHODS FOR ANTI-MICROBIAL EFFECT FOR BONES

RELATED APPLICATIONS

This application claims the benefit of and priority to U.S. Provisional Application No. 62/272,420, filed Dec. 29, 2015 and to U.S. Provisional Application No. 62/252,275, filed Nov. 6, 2015. The contents of each of these applications are incorporated herein by reference in their entireties.

FIELD

The embodiments disclosed herein relate to bone implants, and more particularly to systems and methods providing an anti-microbial effect for bones.

BACKGROUND

Bones form the skeleton of the body and allow the body to be supported against gravity and to move and function in the world. Bone fractures can occur, for example, from an outside force or from a controlled surgical cut (an osteotomy). A fracture's alignment is described as to whether the fracture fragments are displaced or in their normal anatomic position. In some instances, surgery may be required to re-align and stabilize the fractured bone. A bone infection may occur when bacteria or fungi invade the bone, such as when a bone is fractured or from bone fracture repair. These bacteria commonly appear and if not addressed properly can cause server health problems. It would be desirable to have an improved systems and methods for stabilizing, positioning, and repairing a fractured or weakened bone that further includes eliminating bacteria.

SUMMARY

System and methods for providing an anti-microbial effect on a bone are disclosed. According to aspects of the disclosed subject matter, a system for providing an anti-microbial effect on a bone comprising: a delivery catheter having an elongated shaft with a proximal end, a distal end, and a longitudinal axis therebetween, an inner void for passing at least one light sensitive liquid, and an inner lumen; an expandable member releasably engaging the distal end of the delivery catheter, the expandable member capable of moving from a deflated state to an inflated state by infusing at least one light sensitive liquid into the expandable member; and a light conducting fiber sized to pass through the inner lumen of the delivery catheter and into the expandable member, wherein, when the light conducting fiber is in the expandable member, the light conducting fiber is able to initiate hardening of the at least one light sensitive liquid within the expandable member to form a photodynamic implant and the light conducting fiber is able to disperse light energy to provide an anti-microbial effect to the bone.

According to aspects of the disclosed subject matter, a system for providing an anti-microbial effect on a bone comprising: a delivery catheter having an elongated shaft with a proximal end, a distal end, and a longitudinal axis therebetween, an inner void for passing at least one light sensitive liquid, and an inner lumen; an expandable member releasably engaging the distal end of the delivery catheter, the expandable member trial fits into a space within a bone by alternatingly moving from a deflated state to an inflated state and back to the deflated state only by at least one light sensitive liquid, when the at least one light sensitive liquid is passed in and out of the expandable member, one or more channels in the expandable member; and a light conducting fiber sized to pass through the inner lumen of the delivery catheter and into the at least one channel in the expandable member, wherein, when the light conducting fiber is in the one or more channels, the light conducting fiber is able to disperse light energy to provide an anti-microbial effect to the bone.

According to aspects of the disclosed subject matter, a system for restructuring or stabilizing of bones that provides an anti-microbial effect. The system includes a delivery catheter having an elongated shaft with a proximal end, a distal end and a longitudinal axis there between. The delivery catheter includes an inner void for passing at least one light sensitive liquid and also includes an inner lumen. An expandable member releasably engaging the distal end of the delivery catheter, the expandable member trial fits into a space within a bone by alternatingly moving from a deflated state to an inflated state and back to the deflated state only by at least one light sensitive liquid, when the at least one light sensitive liquid is passed in and out of the expandable member. The expandable member is designed to be at least partially placed into the space within the bone, and directly in contact with the bone and to form fit to a surface contact area within the space of the bone. A light conducting fiber sized to pass through the inner lumen of the delivery catheter and into the expandable member, wherein, when the light conducting fiber is in the expandable member, the light conducting fiber is able to disperse light energy to provide an anti-microbial effect prior to infusing the at least one light sensitive liquid in the expandable member. Infusing the at least one light sensitive liquid in the expandable member, wherein the at least one light sensitive liquid is passed in and out of the expandable member to form fit to the surface contact area within the space of the bone. Wherein, when the light conducting fiber is in the expandable member initiate hardening of the at least one light sensitive liquid within the expandable member to form a photodynamic implant. Wherein, an amount of the light sensitive liquid is hardened within the trial fitted expandable member, such that a size and a shape of the formed photodynamic implant has a size and a shape of the space inside the bone, so the bone is restructured to a substantially original size and an original shape around the formed photodynamic implant.

According to aspects of the disclosed subject matter, the system including a cavity in the expandable member includes at least one channel, such that the light conducting fiber is configured to pass into the at least one channel and provide the anti-microbial effect from within the at least one channel.

According to aspects of the disclosed subject matter, a method for providing an anti-microbial effect on a bone comprises gaining access to a cavity in a bone; delivering in an unexpanded state, an expandable member having at least one channel to the cavity in the bone; infusing the at least one light sensitive liquid in the expandable member to move the expandable member from a deflated state to an inflated state; positioning an optical fiber sufficiently designed to emit light energy along a length of the optical fiber inside the at least one channel in the expandable member; activating a light source engaging the optical fiber; and delivering light energy from the light source to the optical fiber to providing an anti-microbial effect on a bone.

The method may further comprise curing the light-curable fluid inside the balloon to harden the expandable member. The method may further comprise prior to the step of infusing the at least one light sensitive liquid in the expandable member, the step of: positioning the optical fiber inside the at least one channel in the expandable member; activating the light source; delivering light energy to the optical fiber from the light source; and removing the optical fiber from the at least one channel in the expandable member.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A shows a schematic illustration of an embodiment of a bone implant system of the present disclosure. The system includes a light source, a light pipe or multiple light pipes, an attachment system, a light-conducting fiber(s), a light-sensitive liquid, a delivery catheter and an expandable member sufficiently shaped to fit within the confines of the medullary canal or other spaces, cavities or gaps in a fractured bone, according to an embodiment of the disclosure;

FIG. 1B and FIG. 1C show schematic illustrations of embodiments of a bone implant device that includes a delivery catheter and an expandable member sufficiently shaped to fit within a space, cavity or a gap in a fractured bone, according to embodiments of the disclosure;

FIG. 2A and FIG. 2B show close-up cross-sectional views of the region circled in FIG. 1A. FIG. 2A shows a cross-sectional view of a distal end of the delivery catheter and the expandable member prior to the device being infused with light-sensitive liquid. FIG. 2B shows a cross-sectional view of the distal end of the delivery catheter and the expandable member after the device has been infused with light-sensitive liquid and light energy from the light-conducting fiber is introduced into the delivery catheter and inner lumen of the expandable member to cure the light-sensitive liquid, according to embodiments of the disclosure;

FIG. 2C and FIG. 2D each show a cross-sectional view of a distal end of the delivery catheter and the expandable member and a light-conducting fiber in the delivery catheter and inner lumen of the expandable member, according to embodiments of the disclosure;

FIG. 7A and FIG. 7B show at least one manifold located within at least one lumen of the expandable member, wherein the at least one lumen of the expandable member is in communication with the one or more channels located within the expandable member as shown in FIG. 3. FIG. 7A shows a manifold located at a proximal end of the expandable member. FIG. 7B shows a manifold located in a lumen at a distal area of the expandable member, according to embodiments of the disclosure;

FIG. 14A, FIG. 14B, FIG. 14C, FIG. 14D, FIG. 14E, FIG. 14F, and FIG. 14G show the initial experimental set up;

Figure 2C:
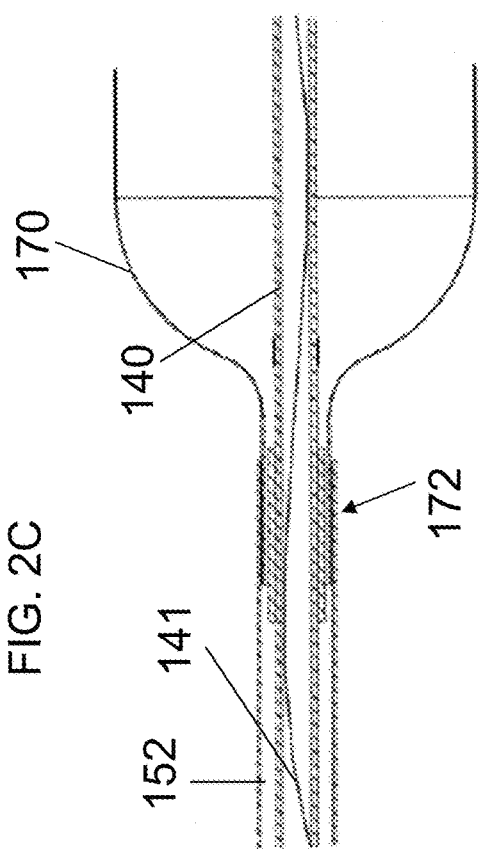
FIG. 2C and FIG. 2D show a close-up cross-sectional view of the regions circled in FIG. 1B and FIG. 1C, respectively.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods for bone fixation procedures are disclosed herein. In some embodiments, devices and methods including stabilization and providing an anti-microbial effect for bone restructuring are disclosed. An anti-microbial effect may also include a bactericidal effect or an antibacterial effect, among other things.

A medical device disclosed herein may be used for treating conditions and diseases of the bone, including, but not limited to, the femur, tibia, fibula, humerus, ulna, radius, metatarsals, phalanx, phalanges, ribs, spine, vertebrae, clavicle and other bones and still be within the scope and spirit of the disclosed embodiments.

Overview

According to embodiments of the present disclosure, the device, system and methods disclosed provide, among other things, a site specific treatment approach to target a specific infection area within a bone. For example, in some embodiments, the site specific treatment approach is designed to provide treatment in the endosteal, i.e. inside surface of the bone, so as to treat infection in the bone from the medullary canal, i.e. from the inside to the outside. This is contrast to treatments using antibiotics to fight infection; the treatment used of antibiotics results in a systemic broad approach towards treating the infection, which is not a targeted site specific treatment as per the instant disclosure. For example, after an invasive surgical procedure an infection may develop in the patient, requiring the patient to undergo antibiotic treatment. Treatments using antibiotics are delivered either orally or by infusion, wherein such broad treatment goes towards an entire anatomical treatment of the body. For example, even during the course of this broad treatment using antibiotics, the specific area of the actual infection may not be properly treated and/or as a result this broad treatment likely will deliver more drugs than is required to treat the specific infection area or mall area. The present disclosure is directed to a site specific approach by applying light to the specific infection area to kill the infected matter or bacteria. The aspects of the present disclosure results in, providing direct treatment to the infection area, using only an amount of treatment necessary to kill the infection, i.e. which is in contrast to the broad treatment approach of using antibiotics. Further, the use of light to treat infection of the present disclosure results in only may be in an additional small amount of antibiotic as a "cleanup" that may be required. Further, at least one aspect of the site specific treatment results in a faster "kill" or termination of the infection versus the broad treatment approach of using the systematic drug, i.e. antibiotics.

According to embodiments of the present disclosure, the device, systems and methods disclosed provide an antimicrobial effect on bones.

According to embodiments of the present disclosure, the device, systems and methods disclosed provide a bactericidal effect on bones.

According to embodiments of the present disclosure, the device, systems and methods disclosed provide an antibacterial effect on bones.

According to embodiments of the present disclosure, the device, systems and methods disclosed provide an anti-infective effect on bones.

According to embodiments of the present disclosure, the device, system and methods disclosed provide for an application of light to kill the infection which creates the formation and transfers energy to molecular oxygen, thus forming the reactive singlet oxygen. This oxidizing species can destroy proteins, lipids, and nucleic acids causing cell death and tissue necrosis. The instant disclosure's application of light creates molecular oxygen, thus forming the reactive porphyrins. For example, during treatment, electromagnetic radiation having wavelengths in the visible spectrum (i.e., visible light above 395 nm, by non-limiting example) reacts with naturally produced and/or concentrated "endogenous" chromophores (porphyrins). At least one effect of the application of the electromagnetic radiation (illumination) is that the light in conjunction with or in combination with the porphyrins produces necrosis or cell death to the bacteria as evidenced by the microorganism's inability to divide. It is noted that the application of treatment of the instant disclosure provides treatment without the addition of ancillary drugs or chemicals, which can be considered as a "holistic" killing treatment or approach to fighting infection.

According to embodiments of the present disclosure, the device, system and methods disclosed provide for an application that can be used as a self-standing instrument to "wand" the canal of the bone or as a part of a balloon (with monomer) to both stabilize and kill the infection, i.e. providing a site specific treatment approach. It is possible that treatment for an infection within a canal of the bone may only include using a balloon placed within the canal and merely introducing the application of light disclosed in the present disclosure to treat or kill the infection area. For example, the use of the balloon can provide at least one benefit, in that the expanded balloon acts as filler within the canal compressing and causing the remaining medullary canal materials to be displaced and putting the balloon in direct apposition to the medullary canal wall. Whereby, the results of the application of the balloon within the medullary canal allow for an environment for an appropriate transmission or application of light to kill bacteria in the infection area. For example, failure to displace the medullary canal materials would result in an occluded canal, which would be preclusive to light meeting the bone walls or endosteal surface, thus failure in treating the infection area.

Further, at least one benefit of the use of light in accordance with the present disclosure may include the termination of newer and more virulent strains of drug resistant bacteria, i.e. "super bugs". Traditional antibiotic methods of killing infections using antibiotic fails to kill virulent strains of drug resistant bacteria, i.e." super bugs. Traditional antibiotic methods kill using a chemical and biologic response associated with O2, i.e. necrosis and cell inability to divide and replicate. As noted above, the present disclosure incorporates the application of light which causes the formation of porphyrins, wherein the application of electromagnetic radiation (illumination) in conjunction with or in combination with the porphyrins, produces necrosis or cell death to the bacteria as evidenced by the microorganism's inability to divide. Further, as noted above, the application of electromagnetic radiation (illumination) according the present disclosure presents a treatment of the infection area from inside the bone to outward.

Illumination Providing an Antimicrobial Effect within Cavities of the Bone

FIG. 1A is a schematic illustration showing various components of an embodiment of a system 100 of the present disclosure. the system 100 includes a light source 108, a light pipe 120, an attachment system 130 and a light-conducting optical fiber 106 having a nonlinear light-emitting portion 158, which emits light from the outside of the optical fiber 106 along its length. The attachment system 130 communicates light energy from the light source 108 to the optical fiber 106. In an embodiment, the light source 108 emits frequency that corresponds to a band in the vicinity of 350 nm to 770 nm, the visible spectrum. In an embodiment, the light source 108 emits frequency that corresponds to a band in the vicinity of 380 nm to 500 nm. In some embodiments, the light source 108 emits frequency that corresponds to a band in the vicinity of 430 nm to 450 nm. In some embodiments, the light source 108 emits frequency that corresponds to a band in the vicinity of 430 nm to 440 nm.

The system 100 includes emitting a beam of a blue light or violet-blue light within a cavity of the bone via an optical fiber for both illuminating towards polymerization as well as towards providing an antimicrobial effect. For example, light from a light source can be used to kill micro-bacteria located within a cavity of a bone before, during and after the healing process of the fractured bone. Steps to kill the micro-bacteria in the cavity of the bone can include emitting the beam of blue light or violet-blue light having a wavelength from about 380 nm to about 500 nm. For example, in some embodiments, the beam of blue light or violet-blue light can have a wavelength from about 400 nm to about 470 nm, including, for example, about 436 nm. However, it will be appreciated in view of this disclosure that, in some embodiments, the blue light/beam may have a wavelength from about 350 to about 500 nm, about 350 to about 550 nm, about 350 nm to about 600 nm, about 350 nm to about 650 nm, about 350 nm to about 700 nm, about 350 nm to about 750 nm, or about 350 nm to about 770 nm. For example, in some embodiments, the blue light/beam may have a wavelength of about 405 nm, about 380 nm, about 436 nm, or about 470 nm.

Still referring to FIG. 1A, the beam of blue light/beam can deliver variable energy densities to bone walls of the cavity of the bone, which can increase the temperature, i.e. bone walls of the cavity of the bone, while emitting the blue light/beam. The steps of emitting the blue light/beam within the cavity of the bone may be completed without: (1) exposing the bone walk to further evasive surgical procedures due to antimicrobial effect related treatments; (2) the need for applying antimicrobial type liquids or related applications; and (3) the need of removing the killed micro bacteria from the affected area. Micro-bacteria may be defined, by non-limiting example, as an opportunistic microorganism. For example, a bacterium, virus, fungus or the like, that takes advantage of certain opportunities to cause disease, i.e. those opportunities can be called opportunistic conditions. These microorganisms are often ones that the human immune system cannot raise an adequate response, such these microorganisms can eventually overwhelm the body's weakened defenses.

For example, according to at least one aspect of the disclosure, it is contemplated to kill micro bacteria that may have an opportunity to exist or already exists within the cavity of the bone. The use of the blue light/beam can include many variables when treating an affected area, by non-limiting example, the blue light/beam may incorporate many combination of aspects when being applied to an affected area such as: (1) variable energy densities, conceptually by altering the wave form on the light liber it is possible to emit more or less light in different and specific areas—and similarly alter the temperature on a local level or site specific area; (2) variable generated temperature(s) at a specific location within the affected area; (3) variable exposure time emitted to the affected area; (4) variable distance of the optical fiber's distal end to the affected area; and (5) a pulsing or constant blue light/beam emitted or a combination thereof, among other things.

Still referring to FIG. 1A, the instant disclosure may additionally include step or steps of incorporating variable temperatures such as cooling an affected area (before, during or after treatment), so that the bone wall temperature along the blue light/beam emission does not exceed a temperature that may result in irreversible damage to the bone walls of the cavity of the bone. It is contemplated that possibly cooling vents may be used in the process so as to pulse a cooling liquid, i.e. water, through channels to cool the implant and the surround tissue. It is also possible that to fill the balloon with a super cooled material so as to necrose or freeze the biofilm, i.e. bacterial colony, through an overall thermal effect and in conjunction with the blue light. By non-limiting example, the bone wall temperature along the blue light/beam emission may be contemplated not to exceed a temperature of about 42° C. or between 40° C. to 45° C. It is contemplated that a super cooled device may be used so that the application necroses tissue.

Further, the energy emitted by the blue light/beam may be termed in portions of joules (i.e. radiant energy), joules per cubic meter (i.e. radiant energy density), watts (i.e. radiant flux), watt per meter and watt per hertz (i.e. spectral flux), watt per steradan (i.e. radiant intensity), or the like.

It is noted that in the application of light to kill bacteria and to have success it is likely dependent upon a variety of factors, not the least of which, may be intensity as defined by joules or (watts) intensity multiplied by time. Further, the polymerization and antimicrobial effects are not the same, i.e. at the same time, or dependent. Such that, where polymerization can be the marriage of a known frequency light to a known monomer, i.e. photo initiator, with a specified time toward polymerization, the successful ability to kill bacteria may require a higher energy deposition than required to cure. It may be possible to circumvent a need to apply non-clinically relevant times, more light, i.e. energy that may need to be applied. Among other things, a possible solution may be to attempt to use higher energy and illumination sources. The limitations in the transference and limitations to the amount of energy may be transported down the fiber.

Among other things, laser light has a limitation, such that energy needs to be dispersed over a wide area and the light needs, unlike an end fire, needs to be transmitted. Further, laser light, which is intense, requires the need to "bleed it off" or disperse it in a fashion over the entire length of the implant, wherein the process of doing so reduces the mw of light energy. Further still, with reduction of the intensity, and mw being a byproduct of implant length, the exposure area requires time to increase. At some point the increased time is no longer clinically relevant, such that when increased to a point where it's longer by some degree, as compared to that of the curing of the implant.

The optical fiber 106 used in the system 100 can be made from any material, such as glass, silicon, silica glass, quartz, sapphire, plastic, combinations of materials, or any other material, and may have any diameter. Further, the optical fiber 106 can be made from a polymethyl methacrylate core with a transparent polymer cladding. It should be noted that the term "optical fiber" is not intended to be limited to a single optical fiber, but may also refer to multiple optical fibers as well as other means for communicating light from the light source to the expandable member. It is possible the fibers, after exciting the light source, may be twisted so as to form into a single fiber. Further, the optical fiber may comprise of a single fiber at a location that is in combination with multiple fibers at another location. It is possible, the multiple fibers positioned at the other location may be further incorporated into another single fiber at yet at another location within the system, i.e. the method of using the light fiber may be a single or multiple fibers or any variation thereof.

Light Source

Still referring to FIG. 1A, it is contemplated the light source may include a single bulb or multiple bulbs, wherein the light source may further include one or multiple ports to attach light fibers. The light fibers or light guides may be joined, mixed or include some combination thereof, within the system. Depending upon the application, the light source can be designed to provide higher outputs in different frequencies, i.e. using multiple bulbs, so as to overcome potential fall off aspects that may occur using a single bulb. If multiple bulbs are used, it is contemplated that there may be multiple types of bulbs used in the system. For example, each different type of bulb may provide a specific attribute to meet an intended design aspect for the particular application, which may include attributes relating frequency ranges, energy density ranges, operation life expectancies, etc. Further, regarding other elements within the system where multiple elements of the same element are used, i.e. light fibers (optical fibers, light guides, etc.), light conductive materials and the like, it is contemplated that there may be different types of the same element used within the system. As noted above, each different type of element may be used depending upon the specific attribute to meet an intended design aspect for the particular application, which may include attributes relating material type(s), performance related ranges, operation life expectancies, etc. In conjunction with choosing a specific element, any materials and elements used with that specific element may be further used, so as to meet the intended planned design for the particular application. For example, it is contemplated a clear liquid epoxy may be used to bind and fill in interstices of multiple fibers towards a smooth tube or the like, with the system.

Delivering Light to Cavities of the Bone

Referring to FIG. 1A, FIG. 1B, FIG. 1C and FIG. 2A and FIG. 2B, for the system to deliver the light to the cavity of the bone, the system 100 further includes a balloon catheter 110 having an elongated shaft 101 with a proximal end 102, a distal end 104, and a longitudinal axis there between. In an embodiment, the balloon catheter 110 can have an outside diameter ranging from about 3 mm (9 French) to about 8 mm (24 French). However, it is noted the balloon catheter 110 may have an outside diameter of about 3 mm (9 French). At least one inner lumen is incorporated within the elongated shaft 101 of the balloon catheter 110. The elongated shaft 101 of the balloon catheter 110 may include two inner lumens. The elongated shaft 101 of the balloon catheter 110 may include three inner lumens, four inner lumens or more. It is contemplated the one or more inner lumens may accept one or more optical fibers. The proximal end 102 of the balloon catheter 110 includes an adapter for passage of at least one of inflation fluids or medical instruments.

The distal end 104 of the balloon catheter 110 includes at least one expandable member 170. The expandable member 170 of FIG. 1A has a bulbous shape; however, the expandable member 170 may have any other suitable shape. It is possible, the at least one expandable member 170 includes multiple expandable members. For example, the distal end 104 of the balloon catheter 110 may include a first inner inflatable balloon positioned inside and completely surrounded by an outer inflatable balloon. In an embodiment, the expandable member 170 can be manufactured from a non-compliant (non-stretch/non-expansion) conformable material. In an embodiment, the expandable member 170 is manufactured from a conformable compliant material that is limited in dimensional change by embedded fibers. One or more radiopaque markers, bands or beads may be placed at various locations along the expandable member 170 and/or the balloon catheter 110 so that components of the system 100 may be viewed using fluoroscopy.

FIG. 1B and FIG. 1C show schematic illustrations of embodiments of a bone implant device. The devices include a balloon catheter 110 and an expandable member 170 sufficiently shaped to fit within a space, cavity or a gap in a fractured bone. It is contemplated the expandable member may be of any shape so as to fit within a space, cavity or a gap in a fractured bone. For example, the expandable members 170 of FIG. 1B and FIG. 1C can have a tapered elongated shape to fill the space, cavity or gap in certain fractured or weakened bones to be repaired or stabilized. In an embodiment, the expandable member 170 can have an antegrade shape as shown in FIG. 1B. In an embodiment, the expandable member 170 can have a retrograde shape as shown in FIG. 1C. In FIG. 1B, the expandable member 170 can have a larger diameter at its distal end than the proximal end. In FIG. 1C, the expandable member 170 can have a larger diameter at its proximal end than the distal end.

In the embodiments shown in FIG. 1A, FIG. 1B, and FIG. 1C, the proximal end of the balloon catheter 110 includes a first port 162 and a second port 164. The first port 162 can accept, for example, the light-conducting fiber 140 or multiple light-conducting fibers. The second port 164 can accept, for example, a syringe 160 housing a light-sensitive liquid 165. In an embodiment, the syringe 160 maintains a low pressure during the infusion and aspiration of the light-sensitive liquid 165. In an embodiment, the syringe 160 maintains a low pressure of about 10 atmospheres or less during the infusion and aspiration of the light-sensitive liquid 165. In an embodiment, the syringe 160 maintains a low pressure of less than about 5 atmospheres during the infusion and aspiration of the light-sensitive liquid 165. In an embodiment, the syringe 160 maintains a low pressure of about 4 atmospheres or less during the infusion and aspiration of the light-sensitive liquid 165. In an embodiment, the light-sensitive liquid 165 is a photodynamic (light-curable) monomer. In an embodiment, the photodynamic (light-curable) monomer is exposed to an appropriate frequency of light and intensity to cure the monomer inside the expandable member 170 and form a rigid structure.

FIG. 2A and FIG. 2B show close-up cross-sectional views of the region circled in FIG. 1. FIG. 2A shows a cross-sectional view of a distal end of the balloon catheter 110 and the expandable member 170 prior to the device being infused with light-sensitive liquid. FIG. 2B shows a cross-sectional view of the distal end of the balloon catheter 110 and the expandable member 170 after the device has been infused with light-sensitive liquid and light energy from the light-conducting fiber is introduced into the balloon catheter 110 and inner lumen of the expandable member 170 to cure the light-sensitive liquid.

As illustrated in FIG. 2A and FIG. 2B, the flexible balloon catheter 110 includes an inner void 152 for passage of the light-sensitive liquid 165, and an inner lumen 154 for passage of the light-conducting fiber 140. In the embodiment illustrated in FIG. 2A and FIG. 2B, the inner lumen 154 and the inner void 152 are concentric to one another. The light-sensitive liquid 165 has a low viscosity or low resistance to flow, to facilitate the delivery of the light-sensitive liquid 165 through the inner void 152. In an embodiment, the light-sensitive liquid 165 has a viscosity of about 1000 cP or less. In an embodiment, the light-sensitive liquid 165 has a viscosity ranging from about 650 cP to about 450 cP. The expandable member 170 may be inflated, trial fit and adjusted as many times as a user wants with the light-sensitive liquid 165, up until the light source 110 is activated, when the polymerization process is initiated. Because the light-sensitive liquid 165 has a liquid consistency and is viscous, the light-sensitive liquid 165 may be delivered using low pressure delivery and high pressure delivery is not required, but may be used.

Figure 2D:
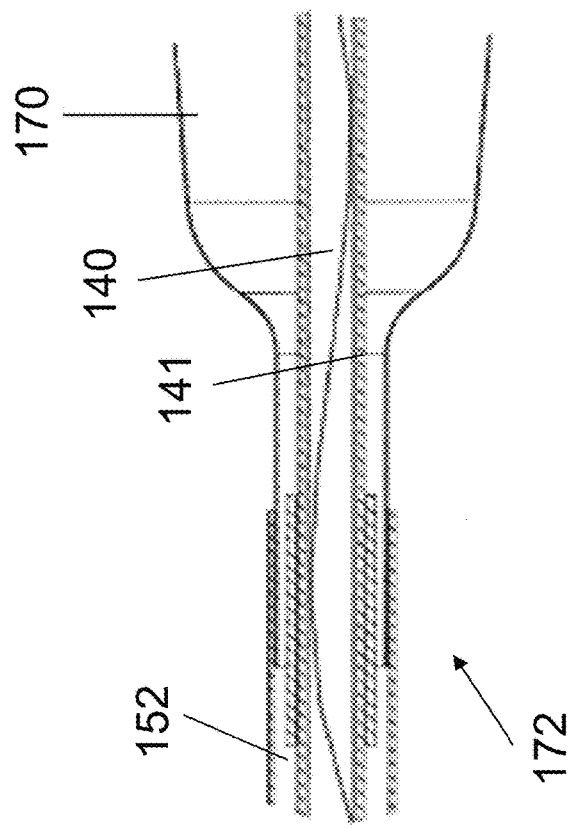

FIG. 2C and FIG. 2D show a close-up cross-sectional view of the region circled in FIG. 1B and FIG. 1C, respectively. FIG. 2C and FIG. 2D show cross-sectional views of a distal end of the balloon catheter 110 and the expandable member 170 and a light-conducting fiber 140 with a cut 141 in the fiber in the balloon catheter 110 and inner lumen of the expandable member 170. The device also has a separation area 172 at the junction of the balloon catheter 110 and the expandable member 170 where the balloon catheter 110 may be separated from the expandable member 170.

Channels within the Expandable Member for the Optical Fibers

Figure 3:
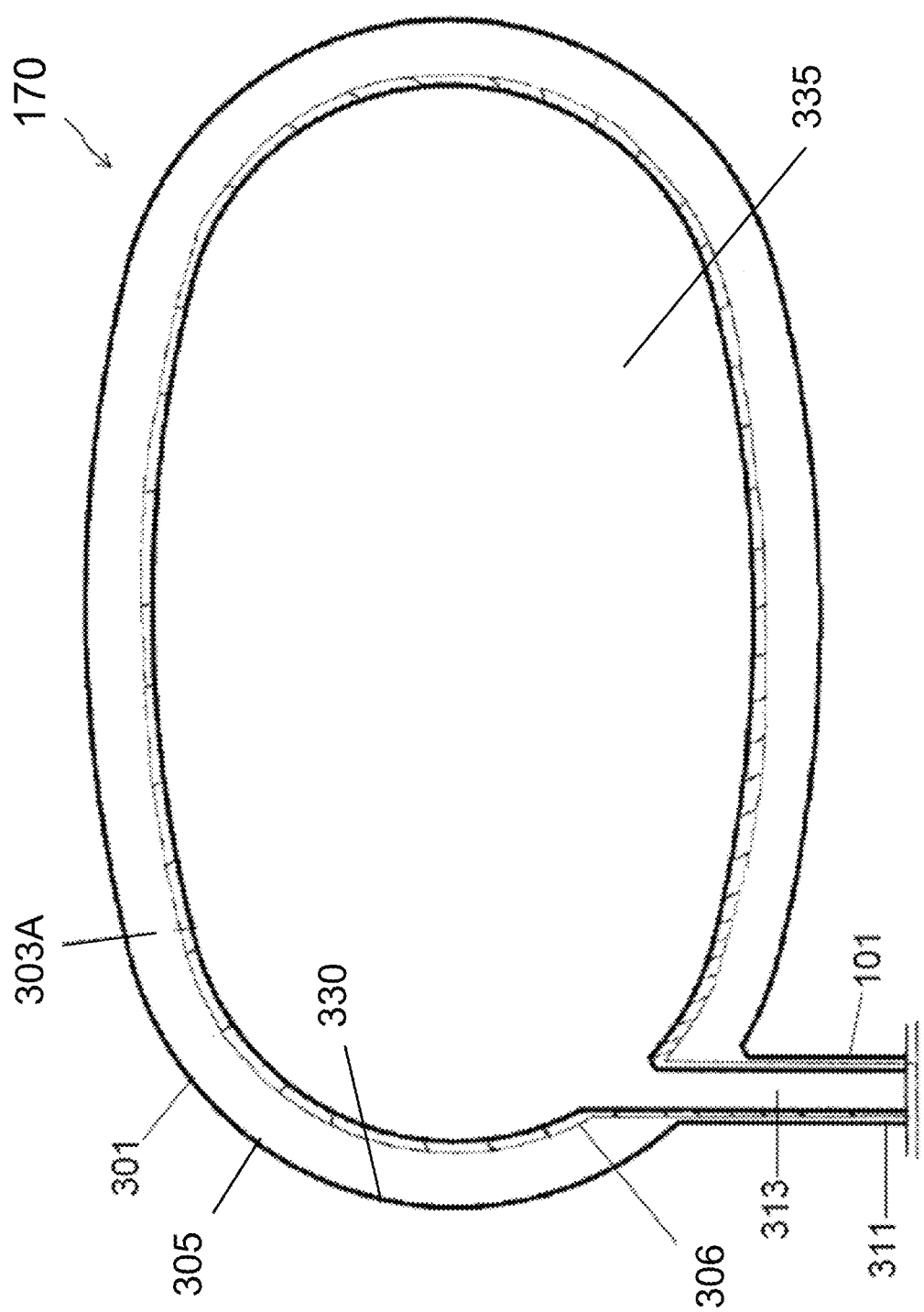
FIG. 3 shows a view of an embodiment of a distal end of a balloon catheter in commutation with expandable member, which comprises an inflatable balloon having at least one channel located in the inflatable balloon approximate an outer surface of the inflatable balloon for at least one optic fiber to enter there through, according to embodiments of the disclosure.

FIG. 3 shows a view of another embodiment of a distal end of a balloon catheter of the present disclosure. The distal end of the balloon catheter includes expandable member 170, which comprises an inflatable balloon 301. The inflatable balloon 301 has a wall with an outer surface 305 and an inner surface 330. The inner surface 330 defines an inner cavity 335.

Further, at least one channel 303A is located in the cavity 305 of the inflatable balloon 301 approximate the inner surface 330 of the inflatable balloon 301. The balloon catheter includes an elongated shaft having a first inner lumen 311 in fluid communication with the expandable balloon 301 which is also in communication with the at least one channel 303A. A separate optical fiber 306 can be incorporated within the elongated shaft of the balloon catheter and encircle the inner surface of the expandable balloon 303A within the at least one channel 303A.

Further, the elongated shaft of the balloon catheter includes a second inner lumen 313 in fluid communication with the expandable balloon 301, wherein another channel (not shown) or multiple channels (not shown) may be incorporated. For example, the additional channels may be used for additional optical fibers that can be incorporated within the elongated shaft of the balloon catheter and encircle the inner surface(s) of the expandable balloon 303A. It is possible that, the channel or channels may be shaped longitudinally within the expandable member, wherein there may be 1, 2, 3, 5, 8 or more longitudinal channels extending from one end to another end of the expandable member. It is possible that a longitudinal channel or channels may be inter-connected with one or more other channels, so that an optical fiber or multiple optical fibers may extend there through. The longitudinal channel may be linear, non-linear or some combination thereof extending from one end to another end of the expandable member.

In an embodiment, the channel or channels may be spiral shaped within the expandable member, wherein there may be 1, 2, 3, 5, 8 or more spiral channels. It is possible that a spiral shaped channel or channels may be inter-connected with one or more other channels, so that an optical fiber or multiple optical fibers may extend there through. The spiral shaped channel or channels may be linear, non-linear or some combination thereof. At least one aspect, by non-limiting example, among other things, is that the channel or channels can be configured to provide a maximum amount of light to the bone walls within the cavity of the bone. At least one benefit, among other things, of a spiral configuration is the large amount of light provided.

Figure 4:
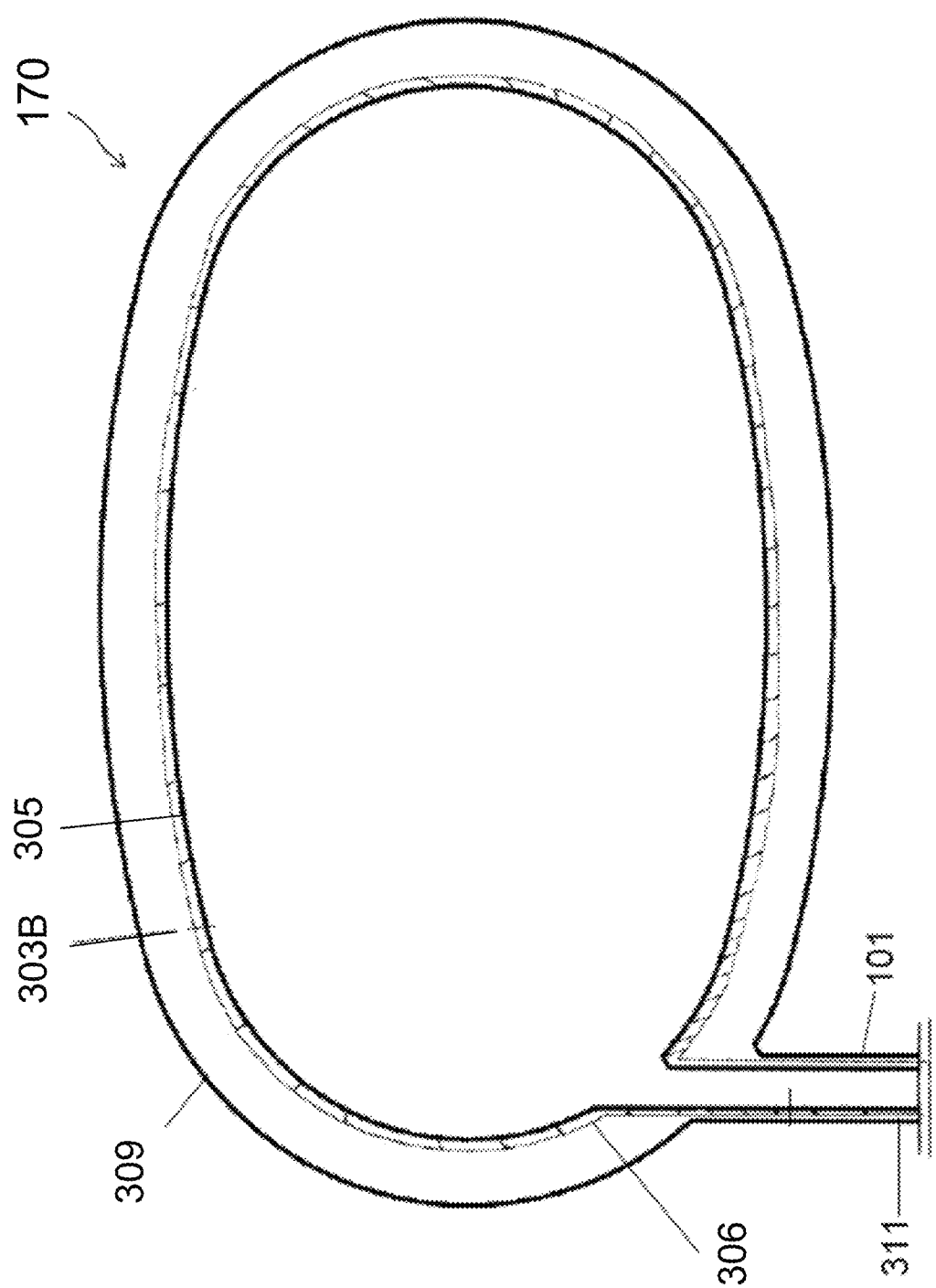
FIG. 4 shows ridges located on an outer surface of the balloon of the expandable member, wherein the ridges include at least one channel for the optical fibers to enter there through, according to embodiments of the disclosure.

Ridges Located on an Outer Surface of Expandable Member Having at Least One Channel for the Optical Fibers FIG. 4 shows ridges 309 located on an outer surface 305 of the balloon 301 of the expandable member 170, wherein the ridges 309 include at least one channel 303B for the optical fibers 306 to enter there through. The distal end of the balloon catheter includes expandable member 170, with the inflatable balloon 301 includes an inner lumen 311 and one or more ridge 309 located the outer surface 305 of the inflatable balloon 301, wherein at least one or more channel 303B is located within the one or more ridge 309. The ridge 309 can be configured to incorporate at least one or more channel 303B for at least one or more optical fiber 306, such that the at least one or more optical fiber 306 is capable of entering and exiting the at least one or more channel 303B.

The ridge or ridges 309 may be shaped longitudinally along an outer surface of the expandable member, wherein there may be 1, 2, 3, 5, 8 or more longitudinal ridges 309 extending from one end to another end of the expandable member 170. It is possible that a longitudinal ridges 309 may be inter-connected with other ridges 309, so that an optical fiber or multiple optical fibers 306, i.e. within the channel's 303B of the ridges 309, may extend there through. The longitudinal ridges 309 may be linear, non-linear or some combination thereof extending from one end to another end of the expandable member.

In an embodiment, the ridge or ridges 309 may be spiral shaped within the expandable member 170, wherein there may be 1, 2, 3, 5, 8 or more spiral ridge or ridges 309. It is possible that a spiral shaped ridge or ridges 309 may be inter-connected with one or more other channels, so that an optical fiber or multiple optical fibers 306 may extend there through. The spiral shaped ridge or ridges 309 may be linear, non-linear or some combination thereof. At least one aspect, by non-limiting example, among other things, is that the ridge or ridges 309 can be configured to provide a maximum amount of light to the bone walls within the cavity of the bone.

The ridges that include channels are configured to provide access for passing optic fibers to pass there through and within the cavity of the bone; either prior to, during the delivery of the light-sensitive liquid, or after the light-sensitive liquid has been cured and hardened. It is contemplated the optical fiber(s) may provide for an antimicrobial effect while light-sensitive liquid is infused through the inner void 210 in the delivery catheter 101 and enters the inner cavity 295 of the expandable member 170.

Figure 5:
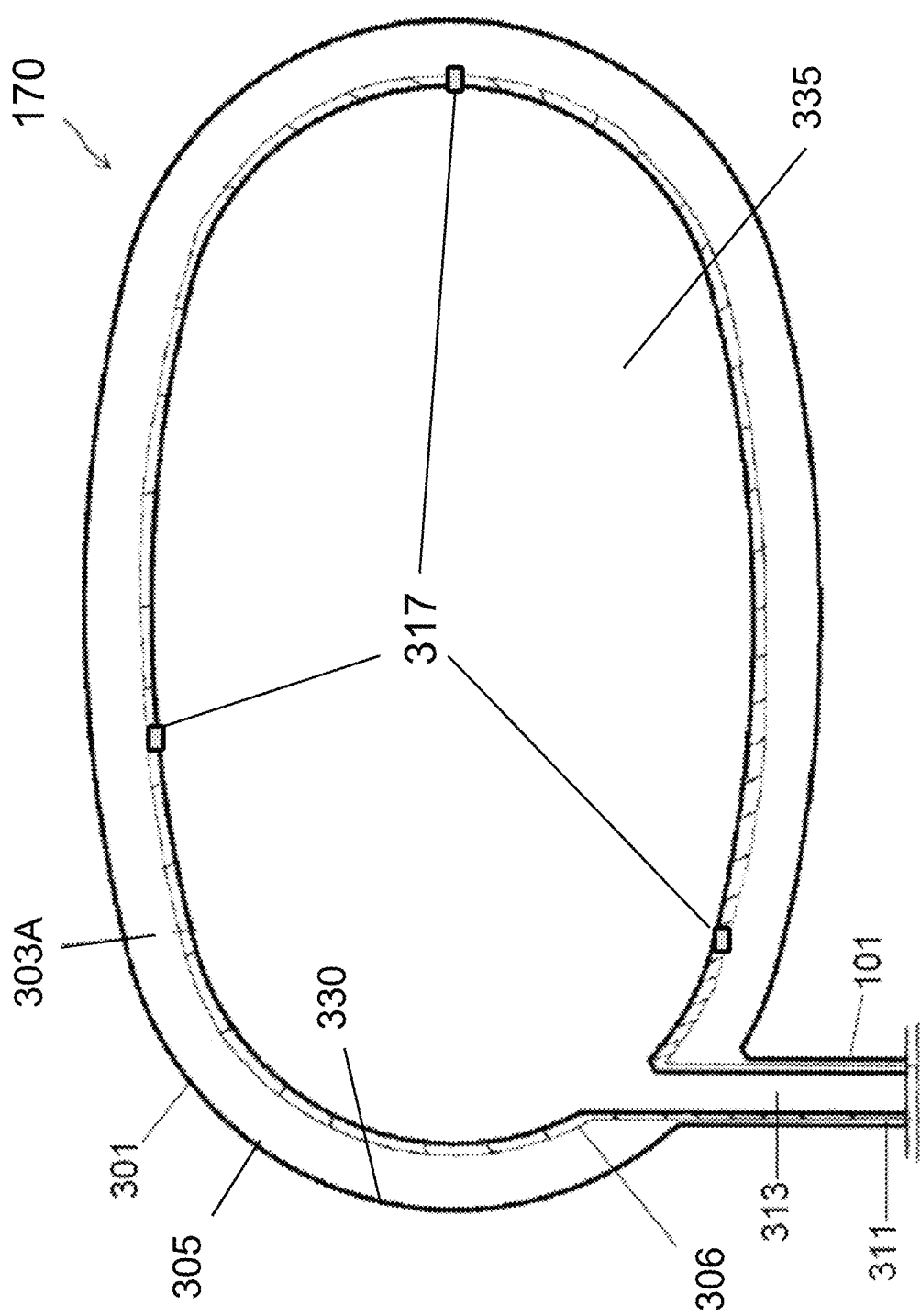
FIG. 5 shows a channel or channels configured with at least one or more reflective prisms, i.e. magnification devices, for magnifying light from the optical fibers, according to embodiments of the disclosure.

Channels Having One or More Reflective Prisms, i.e. Magnification Devices, for Magnifying Light from the Optical Fibers FIG. 5 is similar to and includes the elements of FIG. 3, however, FIG. 5 shows a channel or channels 303A configured with at least one or more reflective prisms 317, i.e. magnification devices, for magnifying light from the optical fibers. The reflective prisms may include reflective prism arrays, reflective prism assemblies and the like, wherein the reflective prisms can be located along the channels 303A, 303B, and/or at an end of the channels 303A, 303B. The reflective prism can be used to reflect light, in order to flip, invert, rotate, deviate or displace the light beam from the optical fiber. For example, the reflective prism may comprise of different types of materials, including reflective tape, among other things.

Figure 6:
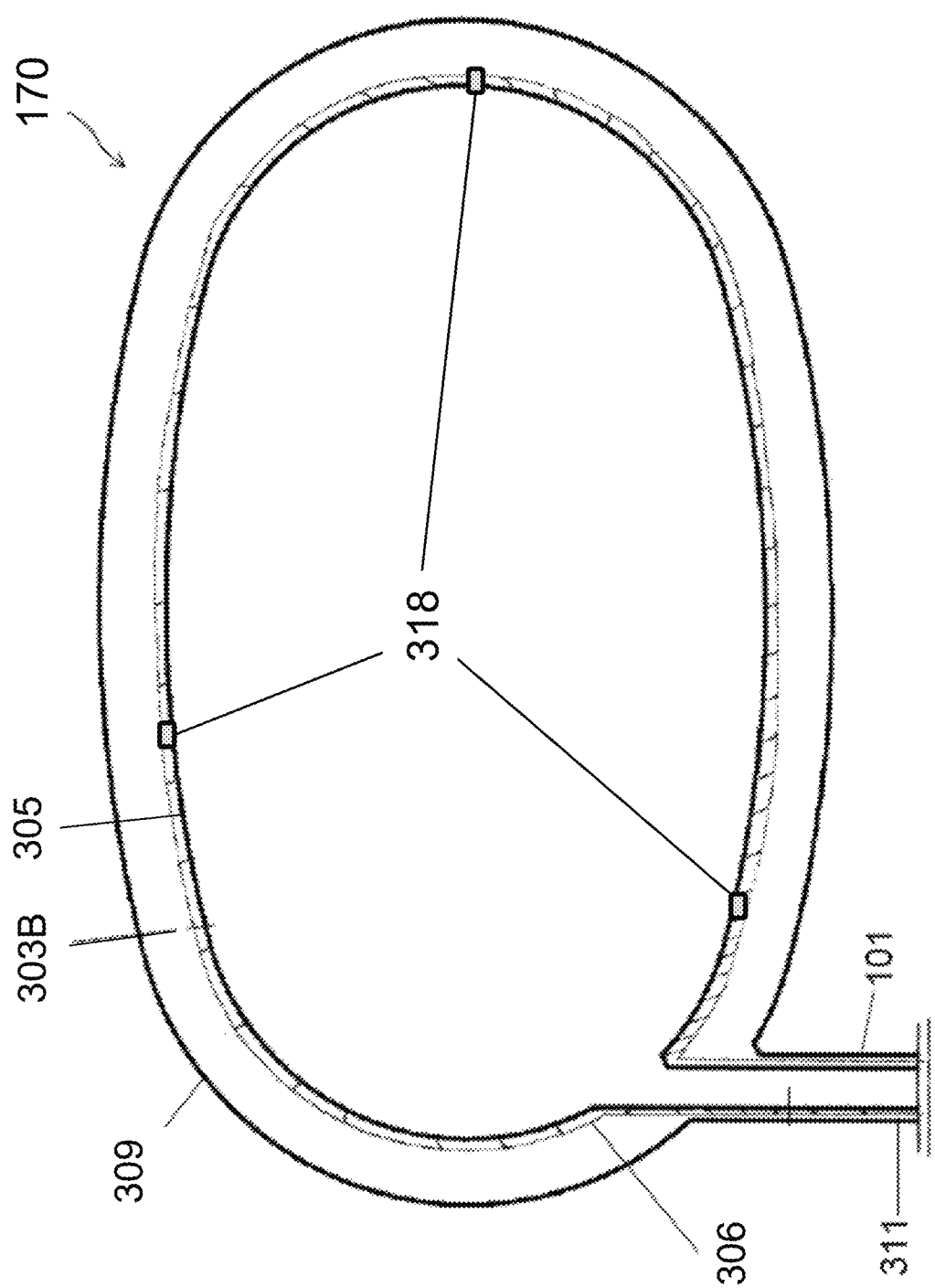
FIG. 6 shows a ridge or ridges configured to include at least one or more reflective prisms, i.e. magnification devices, according to embodiments of the disclosure.

Ribs Having One or More Reflective Prisms, i.e. Magnification Devices, for Magnifying Light from the Optical Fibers FIG. 6 is similar to and includes the elements of FIG. 4, however, FIG. 6 shows a ridge or ridges 309 configured to include at least one or more reflective prisms 318, i.e. magnification devices. The reflective prisms may include reflective prism arrays, reflective prism assemblies and the like, wherein the reflective prisms can be located along the ridge or ridges 309, and/or at an end of the ridge or ridges 309. The reflective prism can be used to reflect light, in order to flip, invert, rotate, deviate or displace the light beam from the optical fiber.

Figure 7B:
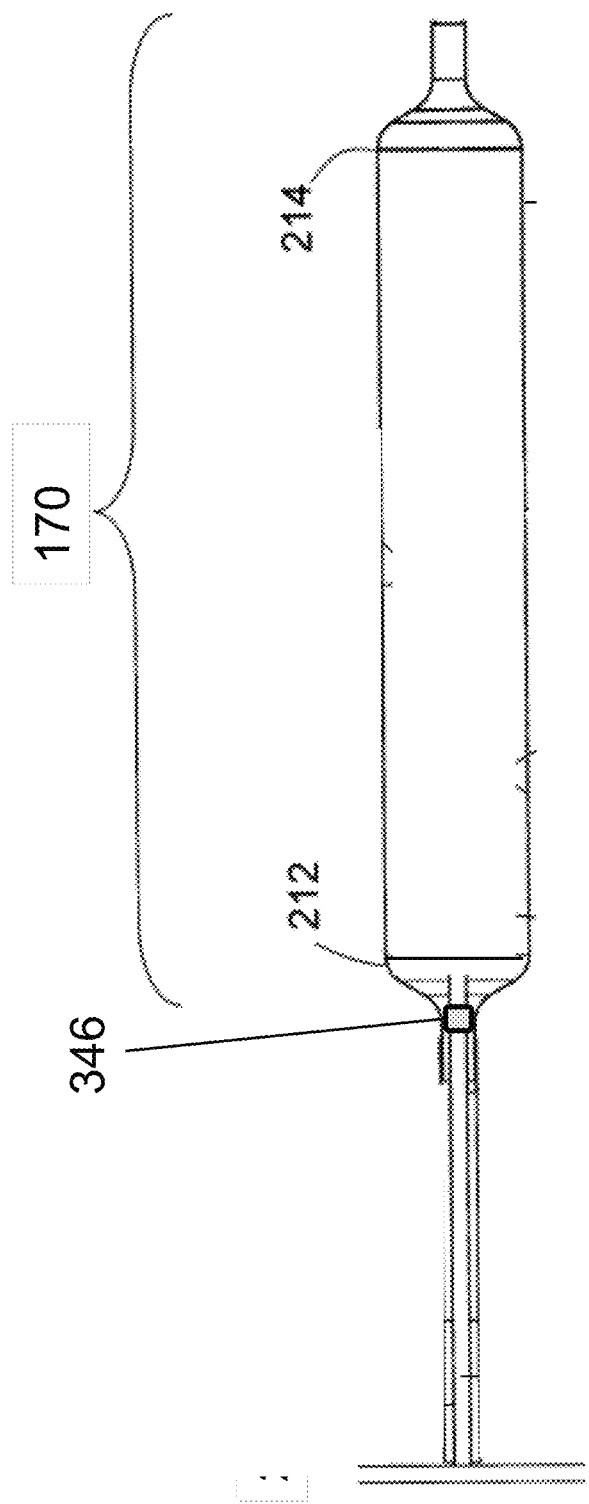

Manifold Incorporated within an End of Expandable Member for Allowing Access to Channels for the Optical Fibers FIG. 7A and FIG. 7B show at least one manifold 344, 346 located within at least one lumen of the expandable member 170.

FIG. 7A is similar to and includes the elements of FIG. 2C, however, FIG. 7A shows the manifold 344 in communication with the at least one lumen of the expandable member 170 and in communication with the one or more channels (not shown) located within the expandable member 170 as shown in FIG. 3. The manifold 344, by non-limiting example, can provide access for one or more light-conducting fiber 306 to enter the at least one lumen of the expandable 170 and through the manifold 344 and further into the channels located within the expandable member 170. The manifold 344 is configured to provide access for passing optic fibers 306 within the cavity of the bone; either prior to, during the delivery of the light-sensitive liquid, or after the light-sensitive liquid has been cured and hardened.

Still referring to FIG. 7A shows the manifold 344 located at a proximal end of the expandable member 170. For example, the manifold 344 may be located within a lumen of the expandable member 170 from about an end of the separation area 172 closest to the proximal end of the expandable member 170 to the proximal end of the expandable member 170 (see FIG. 2C and FIG. 2D). The manifold 344 of FIG. 7A may be utilized by first accessing the flexible balloon catheter first port with the light-conducting fiber (see FIG. 1A, FIG. 1B, and FIG. 1C), then passing the light-conducting fiber through the inner lumen (see FIG. 2A and FIG. 2B), through the a distal end of the balloon catheter and into the separation area 172 (see FIG. 2C and FIG. 2D), then into at least one lumen of the expandable member to enter into the manifold 344.

FIG. 7B shows a manifold 346 located in a lumen at a proximal area 212 of the expandable member 170. Wherein, the manifold 346 of FIG. 7B may be utilized by entry through the flexible balloon catheter, however, the manifold 346 may be utilized by the optical fiber entering the distal end 214 of the expandable member 170.

Regarding FIG. 7A and FIG. 7B, the manifold 344, 346 may comprise of a flexible material, a non-flexible material or some combination thereof. The manifold 344, 346 may comprise of two or more openings that connect with two or more channels located within the expandable member.

Removable Cap to Seal Lumens of Expandable Member

Figure 8A:
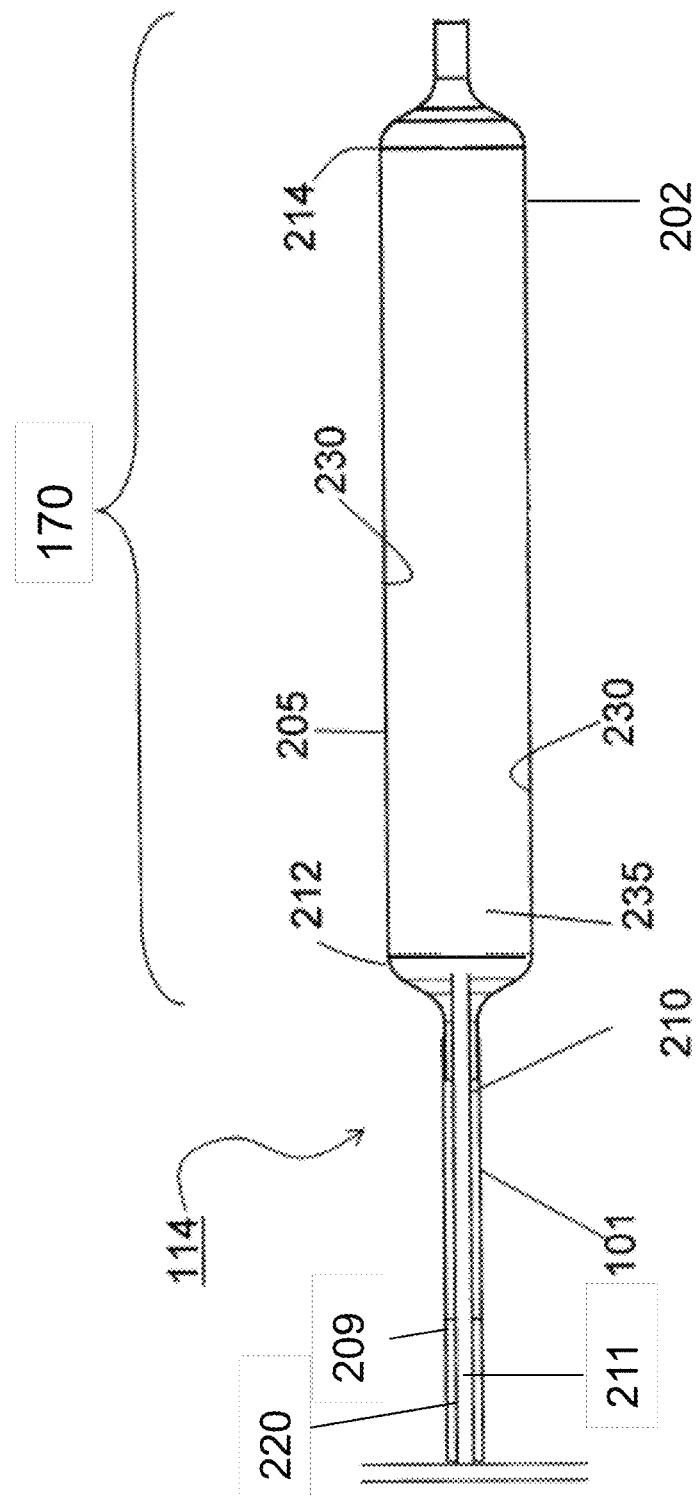
FIG. 8A, FIG. 8B and FIG. 8C show views of a distal end of a device having a removable cap for repairing a weakened or fractured bone of the present disclosure, according to embodiments of the disclosure.
Figure 8B:
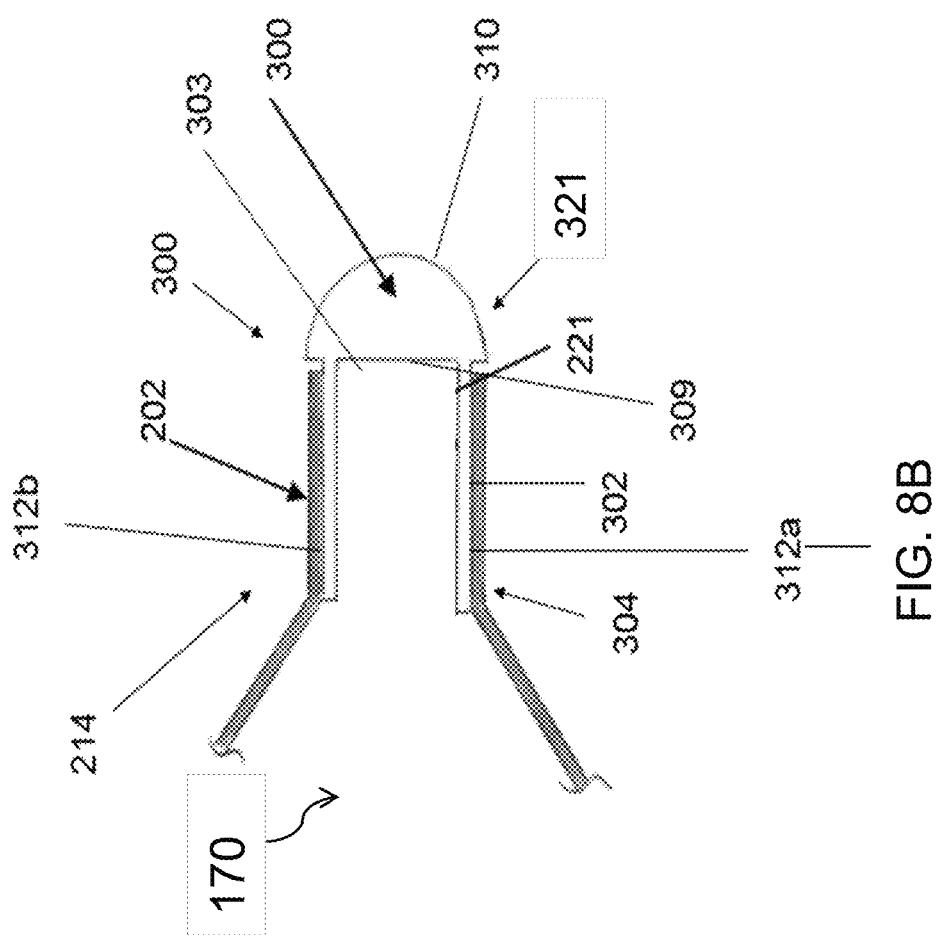
Figure 8C:
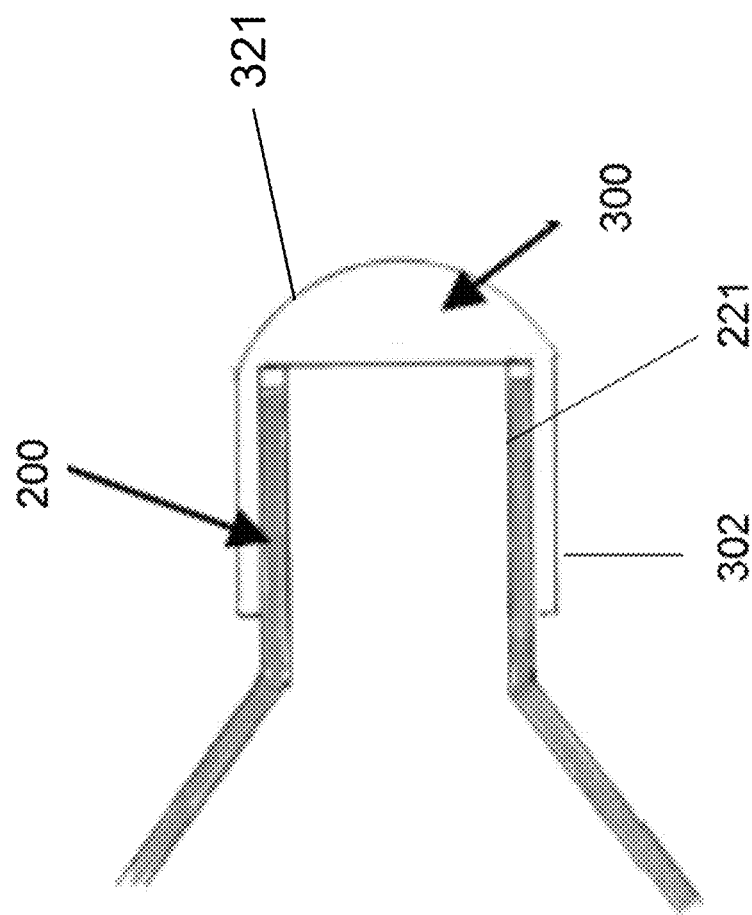

FIG. 8A, FIG. 8B and FIG. 8C show views of a distal end of a device having a removable cap for repairing a weakened or fractured bone of the present disclosure.

It is contemplated the removable cap may be used after the light sensitive liquid has been cured, wherein the hardened expandable member is formed into a formed photodynamic implant. For example, it is possible the formed photodynamic implant may have a removable cap that seals the lumen from fluids and/or other tissue from entering, thus keeping the lumen clean, as well as the light intensity in the future is not diminished. It is possible the central lumen may include a receptacle for at least one rod that may be used to fill the lumen, such that screws on the end of the implant may be designed and/or intended to keep the lumen clean and optically transparent. Further, lumen can be accessed in the future by a removal of the cap, and the rod or the cap may have a valve or access point to allow a minimally invasive means to post operatively introduce the light source. Further still, the cap may have a valve and/or access port that can be accessed in a minimally invasive fashion. It is possible that a small percutaneous needle may be used, where the fiber is introduced through the cap, and/or the fiber may lead in to it. The cap and implant end can be designed to guide and steer the fiber into the lumen. It is possible that there may be a conical end that acts as a recipient. Further, the cap can be of a radiopaque material that it can be located by x-ray.

FIG. 8A is a view of an embodiment of a distal end 114 of the flexible delivery catheter 101. The distal end 114 includes the expandable member 170 releasably mounted on the flexible delivery catheter 101. The expandable member 170 has a wall 202 with an outer surface 205 and an inner surface 230. The inner surface 230 defines an inner cavity 235. In some embodiments, the delivery catheter 101 may include multiple inner lumens or voids. For example, as shown in FIG. 8A, the delivery catheter 101 may include an outer tube 209 and a central tube 220 concentrically disposed within the delivery catheter 101. An inner void 210 may be formed between the outer tube 209 and the central tube 220. The inner void 210 may be utilized for passing a light-sensitive liquid into the inner cavity 235 of the expandable member 170. In some embodiments, the central tube 220 includes an inner lumen 211 for passing a light-conducting fiber (which is not illustrated in FIG. 2) into the expandable member 170 to cure the light sensitive liquid inside the inner cavity 235 of the expandable member, as described in detail below. It should be noted that while the delivery catheter 101 is described as having the central lumen 220 concentric with the outer tube 209, the central lumen 220 may be off-set relative to the outer tube 209.

The expandable member 170 includes a proximal area 212 and a distal area 214. The proximal area 212 of the expandable member 170 is releasably connected to the delivery catheter 101. The distal area 214 may be connected to the delivery catheter 101 in a variety of ways.

In reference to FIG. 8B, in some embodiments, the distal area 214 of the expandable member 170 may be connected to a distal cap 300. The distal cap 300 terminates and seals off the area 214 (or lumen) of the expandable member 170 to prevent the flow of a light-sensitive liquid outside the balloon and the ingress of bodily fluids inside the balloon. One potential benefit of utilizing the distal cap 300 is ease of manufacture and more consistent tip quality when compared to traditional melt forming of expandable member 170 directly to the delivery catheter. An additional benefit of the use of the distal cap 300 may also include the ability to reflect back or scatter light radiating from the end of the conducting fiber to improve the light-sensitive liquid cure times or depth of cure. The reflected light from the distal cap 300 may increase the energy that is directed towards the light-sensitive liquid in the expandable member 170 and thus may increase the photo-initiation rate (and thus polymerization rate) of the light-sensitive liquid.

In some embodiments, the distal cap 300 may be formed, molded or machined from an implant grade polymer (e.g., PET), or another biocompatible material. The distal cap 300 may also be made from a filled material. For example, the PET polymer may be blended with a radiopaque material (e.g., barium sulfate, tungsten, tantalum, etc.) such that the distal cap 300 may be viewed with the assistance of fluoroscopic imaging. In some embodiments, the distal cap 300 may also be covered with a reflective material such as a gold film (or other metallic highly polished implant grade film) to enable the distal cap 300 to reflect light radiating from the end of the light pipe back into the balloon. This reflected light can help to reduce the cure time of the light sensitive liquid contained within the expandable member 170 to due to the increase in light energy directed at the light sensitive liquid. In some embodiments, the distal cap 300 may also be fabricated from a crystalline material (such as crystalline PET) to block the transmission of light through the end of the device 100 and to reflect and/or scatter the light back to the light sensitive liquid in the expandable member 170.

As illustrated in FIG. 8B, a distal cap 300 includes a body 302 having a proximal end 304 and a distal end 321. The body 302 defines an inner compartment 303 wherein at least one manifold (not shown) may optionally be positioned. The distal cap 300 may stabilize the at least one manifold and may minimize movement of the at least one manifold during the operation. It is possible the at least one manifold may be secured inside the compartment 303 by press fitting the at least one manifold into the compartment 303; applying permanent adhesive on the surfaces between the at least one manifold and the compartment 303; melt bonding the two surfaces together or other techniques.

FIG. 8B and FIG. 8C show the distal end 321 of the body 302 may be either open or closed. In some embodiments, the distal cap 300 closes the distal tip 321 of the body 302 to close the distal tip 321. The distal cap 300 includes an inner surface 309, which faces the body 302, and an outer surface 310, which faces away from the body 302. In some embodiments, the outer surface 310 of the distal cap 300 may be rounded or smooth to provide the device 100 with an atraumatic distal point. In some embodiments, the distal cap 300 may have a semi-circular shape with a flat inner surface and a curved outer surface.

In reference to FIG. 8B, in some embodiments, the material forming the expandable member 170 may be attached to the outer surface of the body 302. In some embodiments, the outer surface of the body 302 includes recessed attachment sections 312a, 312b to which the material of the expandable member 170 can be attached. In some embodiments, the outer surface of the body 302 may be recessed by a depth approximately equal to the thickness of the expandable member material. In this manner, when the expandable member material is attached to the body 302, the outside of the expandable member material is substantially aligned with the outer surface 310 of the distal cap 300. The material of the expandable member 170 can be attached to the body 302 by a variety of methods, including, without limitation, adhesives such as cyano-acrylates or epoxies, crimping metallic rings over the expandable portion, melt bonding the expandable member to the body 302 with the use of heat (e.g., RF generated), ultrasonically welding the expandable member to the body 302, or another method or combination of methods.

In reference to FIG. 8C, in some embodiments, the material of the expandable member 170 may be attached to the inner surface of the body 302 of the distal cap 300.

Optic Fibers

The light conducting fibers or optical fibers may include a single optical fiber or a plurality of light conducting fibers 140, wherein the optical fibers may be positioned side-by-side or in parallel in the expandable member 170 (see FIG. 1B and FIG. 1C). In an embodiment, a plurality of light conducting fibers 140 can be positioned serially with ends of adjacent light conducting fibers 140 aligned or abutting on another in an end to end fashion (see FIG. 1B and FIG. 1C). For example, one light conducting fiber may be positioned in the distal portion of the expandable member and another light conducting fiber may be positioned in the proximal portion of the expandable member 170. In an embodiment, a plurality of light conducting fibers can be positioned in a combination of parallel and serial positions, such as partially overlapping or any other suitable configuration. In an embodiment, a plurality of light conducting fibers can be attached to a single light source with a splitter, or can be attached to a plurality of light sources.

The most basic function of a fiber is to guide light, i.e., to keep light concentrated over longer propagation distances despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding may be protected with a polymer coating. Light is kept in the "core" of the light-conducting fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face.

In an embodiment, an optical fiber of the present disclosure is manufactured from a Lumenyte STA-FLEX® "SEL" END LIGHT OPTICAL FIBER, available from Lumenyte International Corporation of Foothill Ranch, Calif., can be employed. These optical fibers may each consist of a light transmitting solid large core, a Teflon® clad and a black bondable outer jacket. The optical fiber may transmit light from a light source to the distal tip for use as a point source. The optical fiber may have a wide 80 degree acceptance angle and 80 degree beam spread, allowing the light to be viewed from more oblique angles. The light transmitting core may be solid, may have no light diminishing packing fraction losses and may be easily spliced. The jacket may be bondable. Custom jackets may be available for more flexibility and color options. The optical fiber can each have a transmission loss (attenuation) of less than approximately 1.5% per foot, a bend radius (minimum) of approximately 6 times the fiber's diameter, temperature stability of up to approximately 90° C. (194° F.), spectral transmission range of approximately 350-800 nm, an acceptance angle of approximately 80°, a refractive index core of approximately 1.48 or greater, cladding of approximately 1.34 or less and a numerical aperture of approximately 0.63. The length of the optical fiber can be approximately 100 continuous feet. Splicing may be achieved in the field using a splice kit, such as the Lumenyte Splice Kit, and carefully following the instructions. Factory splicing may be an option. An optic cutter, such as Lumenyte's Optic Cutter, may be advised for straight, clean, 90° fiber cuts. These fibers may be installed by removing approximately 4 inches (10 cm) of the outer jacket (not the fluoropolymer cladding) before inserting fiber into the light source. An end of the fiber may be near, but not touching the illuminator (light source) glass to assist in achieving maximum brightness.

In an embodiment, an optical fiber of the present disclosure is manufactured from a ESKA™ High-performance Plastic Optical Fiber: SK-10 and SK-60 and/or ESKA™ Plastic Fiber Optic & Cable Wiring, manufactured by Mitsubishi Rayon Co., Ltd., which are all available from Mitsubishi International Corporation of New York, N.Y. These optical fibers may each consist of a light transmitting PMMA (polymethylmethacrylate) core and a fluorinated polymer as the cladding. It should be appreciated that the above-described characteristics and properties of the optical fibers are exemplary and not all embodiments of the present invention are intended to be limited in these respects.

In some embodiments, optical elements may be oriented in alignment with the notches, cuts or openings in the nonlinear light-emitting portion of an optical fiber of the present disclosure to adjust the light output. Such optical elements may include lenses, prisms, filters, spliters, diffusers and/or holographic films. The light source, and more specifically, the optical fibers may have some or all of the properties and features listed in U.S. Pat. No. 6,289,150, which is hereby incorporated by reference in its entirety, as not all embodiments of the present invention are intended to be limited in these respects.

One or more optical elements, such as diffusers, polarizers, magnifying lenses, prisms, holograms or any other element capable of modifying the direction, quantity or quality of the illumination, individually or in combination can also be added and aligned with the core-clad, notches and channel, track or holder and/or reflector.

Further, the implant may be designed to amplify light to the surrounding areas using one of reflective prisms within, Fresnel lens, Magnification lens on the surface, shapes to the external form of the implant that are designed to magnify/amplify the light transmission.

Figure 9:
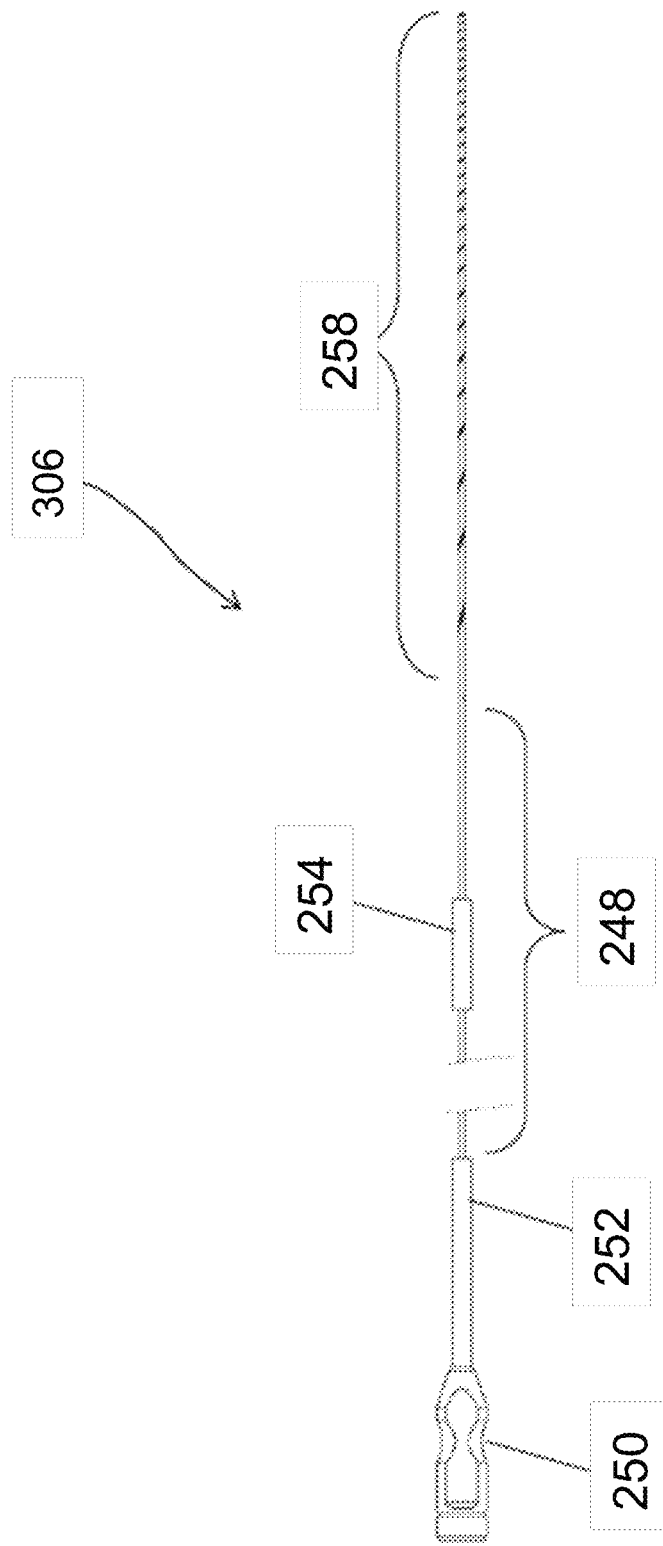
FIG. 9 shows an embodiment of an optical fiber of the present disclosure fabricated from a flexible light transmitting material that can be inserted into at least one channel, according to embodiments of the disclosure.

Customized Cuts Along Optical Fiber to Align with Channel Configurations to Maximize Light Amplification FIG. 9 shows an embodiment of an optical fiber 306 of the present disclosure fabricated from a flexible light transmitting material that can be inserted into at least one channel. The optical fiber 306 includes a hub 250 at a proximal end for attaching to a light source (either directly or indirectly, for example, through the use of an attachment system, see FIG. 1). The optical fiber 306 includes a linear elongated portion 248 for guiding light towards a nonlinear light-emitting portion, generally referred to as 258, which emits light from the outside of the fiber along its length. The nonlinear light-emitting portion 258 can be any length suitable for a given application. The distal tip of the optical fiber 306 may also emit light creating a small spotlight effect. In an embodiment, the optical fiber 306 also includes a flexible strain relief 252 just to the right of the hub 250 and a depth stop 254. In an embodiment, the strain relief 252 prevents snapping of the optical fiber 306 at the hub 250 junction. In an embodiment, the strain relief 252 and the depth stop 254 are made from a flexible material. In an embodiment, the strain relief 252 and the depth stop 254 are made from Santoprene™, a thermoplastic rubber. FIG. 9 shows the optical fiber 306 in an elongated stretched condition and being in a "temporary" shape. In the temporary shape, the nonlinear light-emitting portion 258 is stretched and assumes a linear conformation in which the nonlinear light-emitting portion 258 of the optical fiber 306 can be advanced through the inner lumen of the elongated shaft of the balloon catheter 110.

As illustrated in FIG. 9, for example, according to an embodiment, a helical design may be provided that includes cuts at a most proximal portion of the light-emitting portion that are spread farther apart than cuts at a most distal portion of the light-emitting portion. Typically, when an optical fiber is attached to a light source that is "on", the cuts at the proximal portion of the light-emitting portion will emit light that looks brighter than the cuts at the distal portion of the light-emitting portion when in at least one channel.

The optical fiber may include a non-shape memory optical fiber or a shape memory optical fiber depending on the application relating to one or more channels or not relating to one or more channels located within or on the outer surface (i.e. within ridges) of the expandable member. For example, it may be desirable to provide shape memory to the light-emitting portion of an optical fiber of the present disclosure so as to conform to a shape of at least one channel. In some embodiments, the shape memory can be imparted to the light-emitting portion using conventional techniques known in the art. By way of a non-limiting example, a distal length of an optical fiber of the present disclosure may first be heat treated to provide stress relief, that is, to remove any shape memory from the optical fiber induced into the optical fiber during the manufacturing process. Heat treatment can also be used to induce a pre-set into the optical fiber. The distal length of the stress-relieved optical fiber may then be wound around a circular mandrel to provide the distal length with a desired shape. Next, the mandrel with the coiled optical fiber can be subjected to heat treatment to induce the desired shape and then quenched to set the desired shape into the optical fiber. In an embodiment, the optical fiber may be heat treated using a water bath.

Figure 10:
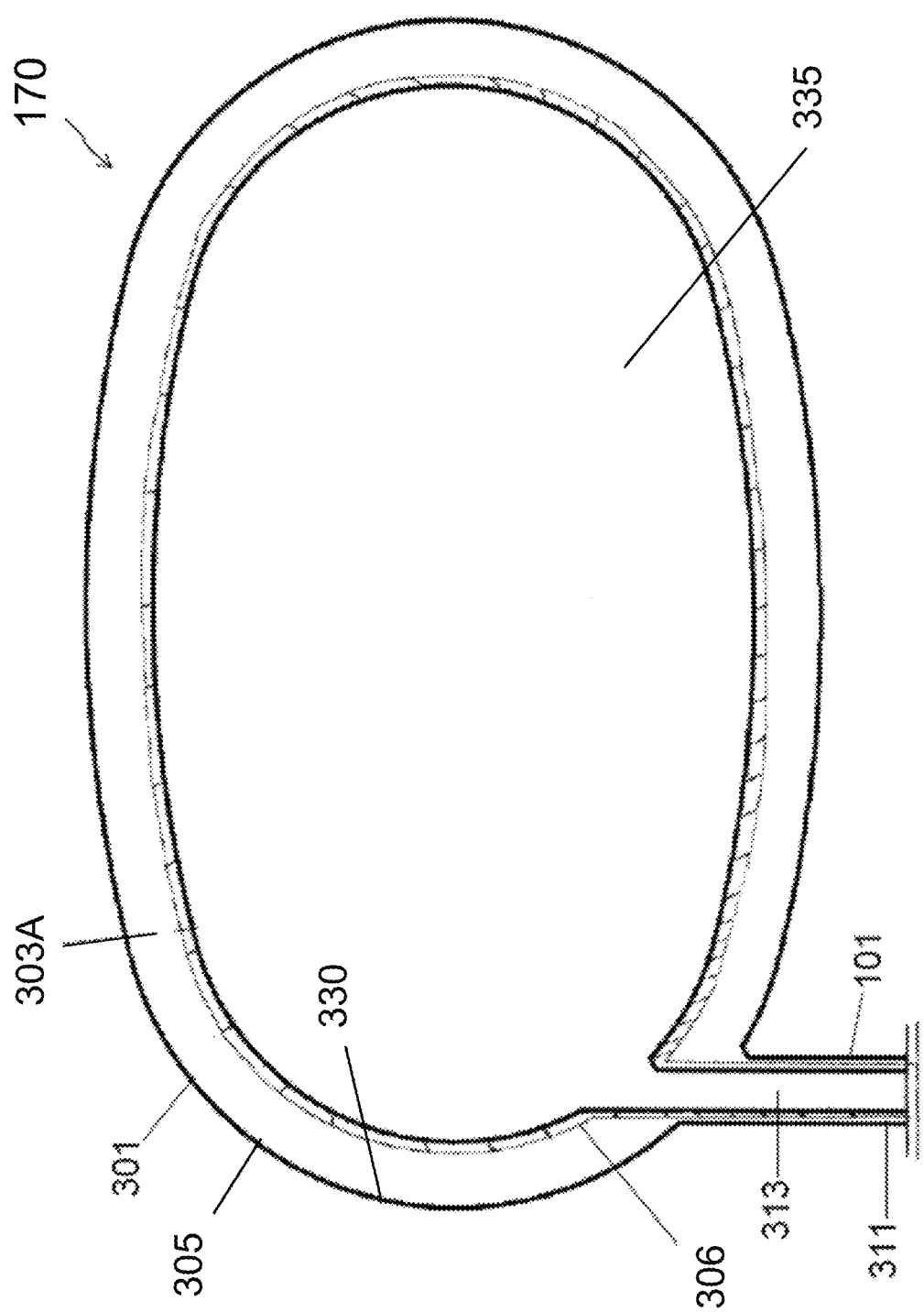
FIG. 10 shows a view of another embodiment of a distal end of a balloon catheter of the present disclosure, which is similar to FIG. 3, wherein the optical fiber has a pre-defined shape specific to the shape of the channel, according to embodiments of the disclosure.

FIG. 10 shows a view of another embodiment of a distal end of a balloon catheter of the present disclosure, which is similar to FIG. 3, wherein the optical fiber 306 has a pre-defined shape specific to the shape of the channel 303A. Wherein the optical fiber 306 can be incorporated within the elongated shaft of the balloon catheter and encircle the inner surface 330 of the expandable balloon 303A within the channel 303A.

The nonlinear light-emitting portion can be any given length suitable for a given application. For example, a nonlinear light-emitting portion of an optical fiber of the present disclosure can have a length ranging from about 60 mm to about 300 mm, 60 mm to about 400 mm, 60 mm to about 500 mm or 60 mm to about 600 mm. It is contemplated the optical fiber may be shaped to incorporate a single loop to extend an entire length of the channel 303A or only partially extend the entire length of the channel 303A.

It is possible illuminators may be made in the optical fiber core alone before the cladding is added and/or the illuminators may be made in the cladding and the core after it has been surrounded by the cladding. In some embodiments, when the cladding is heated to tightly shrink around the core, the cladding may affect the uniformity of the illuminators in the core by either entering the notch or closing the cut thereby reducing the potential light deflecting properties of the illuminator.

The illuminators may be positioned to direct light across the greater diameter of an elliptical optical fiber core out and out through a region opposite from each of the respective illuminators. This may be accomplished by angling the notches and/or cuts to direct light from the light source through the optic core. The illuminators allow better control of escaping light by making the notches, which are positioned on one side of the optic to direct the light rather than allowing the cuts to reflect/refract light in various directions which reduces the contribution of light to a desired focusing effect.

In an embodiment, the total light output from a nonlinear light-emitting portion of the present disclosure having a length of about 100 mm is the same as a nonlinear light-emitting portion of the present disclosure having a length of about 300 mm. In an embodiment, the total light output required for the nonlinear light-emitting portion of an optical fiber of the present disclosure is about 10 µW/cm$^2$, 20 µW/cm$^2$, 30 µW/cm$^2$, 40 µW/cm$^2$, 50 µW/cm$^2$ or 60 µW/cm$^2$.

In some embodiments, the optical fiber may include an optical fiber core surrounded by cladding material and one or more illuminators. The illuminators may be of uniform size and shape positioned in a predetermined, spaced-apart relation, linearly, along a side of the optical fiber core. The optical fiber core may be received in a track and/or holder and/or reflector comprising a channel constructed with a reflective interior surface centered about the illuminators. The holder and/or reflector may be positioned adjacent to or in contact with the plurality of illuminators.

Figure 11A:
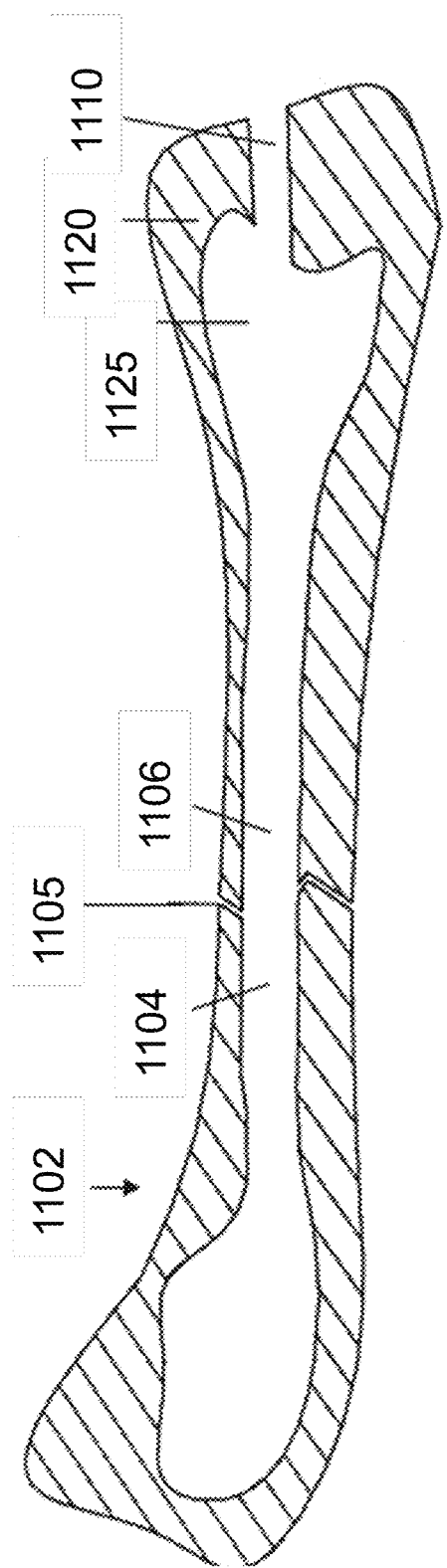
FIG. 11A, FIG. 11B, FIG. 11C, FIG. 11D and FIG. 11E provide embodiment methods for delivering light and/or implanting an intramedullary implant of the present disclosure within the intramedullary space of a weakened or fractured bone, according to embodiments of the disclosure.

Methods of Delivering Light to Cavities of the Bone to Provide for an Anti-Microbial Effect FIG. 11A, FIG. 11B, FIG. 11C, FIG. 11D and FIG. 11E provide embodiment methods for delivering light and/or implanting an intramedullary implant of the present disclosure within the intramedullary space of a weakened or fractured bone. A minimally invasive incision (not shown) may be made through the skin of the patient's body to expose a fractured bone 1102. The incision may be made at the proximal end or the distal end of the fractured bone 1102 to expose the bone surface. Once the bone 1102 is exposed, it may be necessary to retract some muscles and tissues that may be in view of the bone 1102. As shown in FIG. 11A, an access hole 1110 may be formed in the bone by drilling or other methods known in the art. In some embodiments, the access hole 1110 has a diameter of about 4 mm to about 7 mm. In some embodiments, the access hole 1110 has a diameter of about 9 mm.

The access hole 1110 extends through a hard compact (cortical) outer layer 1120 of the bone into the relatively porous inner or cancellous tissue 1125. For bones with marrow, the medullary material should be cleared from the medullary cavity prior to insertion of the inventive device. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be cleared or loosened to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,974 entitled "Apparatus for Preparing the Medullary Cavity," U.S. Pat. No. 6,478,751 entitled "Bone Marrow Aspiration Needle," and U.S. Pat. No. 6,958,252 entitled "Apparatus for Extracting Bone Marrow."

Figure 11B:
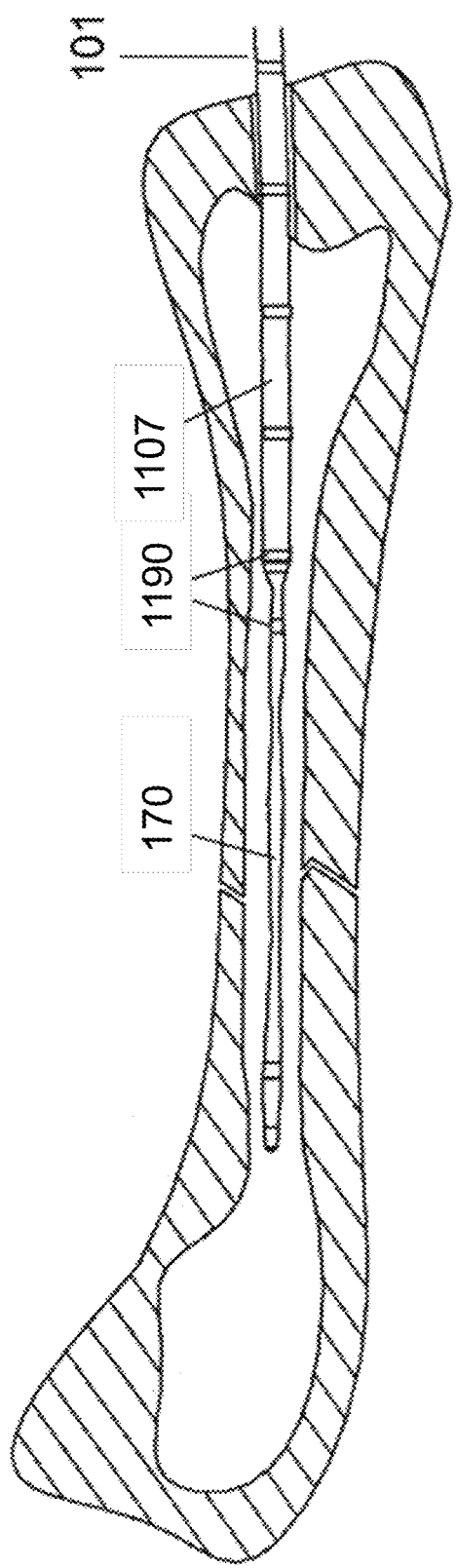

A guidewire (not shown) may be introduced into the bone 1102 via the access hole 1110 and placed between bone fragments 1104 and 1106 of the bone 1102 to cross the location of a fracture 1105. The guidewire may be delivered into the lumen of the bone 1102 and may cross the location of the break 905 so that the guidewire spans multiple sections of bone fragments. As shown in FIG. 11B, the expandable member 170 of the delivery catheter 101 for repairing a fractured bone, which is constructed and arranged to accommodate the guidewire, is delivered over the guidewire to the site of the fracture 1105 and spans the bone fragments 1104 and 1106 of the bone 1102.

In some embodiments, it is contemplated that at least one optical fiber or other light source may be introduced into the bone for a period of time prior to placing the expandable member 170 within the cavity of the bone to provide for an anti-microbial effect. That is, in some embodiments, the bone 1102, the cavity 1110, and/or the surrounding tissue can be pre-illuminated to substantially sterilize the repair site prior to introduction of the expandable member. In some embodiments, because the pre-illumination light source does not need to pass through the balloon catheter 110, the pre-illumination light source can advantageously be a larger, higher-powered light source than the in-process light source for greater initial anti-microbial effect.

In some embodiments, the guidewire can be placed by use of a split sheath and dilator (not shown). In some embodiments, the split sheath and dilator can include an outer tube-shaped sheath and an inner dilator extending coaxially through the sheath. In some embodiments, the inner dilator can include a passageway sized and shaped for passing the guidewire therethrough. In some embodiments, the guidewire, the sheath, and/or the dilator can include at least one optical fiber or other light source for illuminating the repair site. In some embodiments, the sheath, the dilator, and/or the guidewire can thereby be used to pre-illuminate the repair site, illuminate the repair site during installation of the expandable member 170, and/or to illuminate the repair site during curing and hardening of the expandable member 170. Thus, by providing light source integrated within the sheath, dilator, and/or guidewire, a duration of the illumination of the repair site can be increased, thereby improving the anti-microbial effect.

Once the expandable member 170 is in place, the guidewire may be removed. The location of the expandable member 170 may be determined using at least one radiopaque marker 1190 which is detectable from the outside or the inside of the bone 1102. Once the expandable member 170 is in the correct position within the fractured bone 1102, a delivery system which contains optical fiber(s) passes light from a light source through the first port 162, through the inner lumen of the elongated shaft of the balloon catheter 110, through the distal end 104 of the balloon catheter 110, through the inner lumen of the expandable member and into the cavity of the bone. It is contemplated the optical fiber(s) may pass through a channel located within the expandable member. It is also possible the optical fiber(s) may pass through a manifold located in the inner lumen of the expandable member and then into a channel located within the expandable member. It is possible for the optical fiber(s) to enter a channel located within a ridge positioned on an outer surface of the expandable member.

It is possible for radiopaque markers and guides to provide alignment towards steering the user towards a correct position. Further, the end of the implant may have a longer inner tube and light guide receptacle that is longer than the implant and extends several inches beyond. Further still, this end could be left attached to the implant and buried subcutaneously and sealed, so that when and, if needed, the end was exposed via a small incision, the rolled tube exposed and the light fiber introduced would all make for the delivery to be easier.

Once the optical fiber(s) is positioned within the cavity of the bone, the optical fiber(s) is capable of providing for an anti-microbial effect, either prior to, during the delivery of the light-sensitive liquid, or after the light-sensitive liquid has been cured and hardened. It is contemplated the optical fiber(s) may provide for an antimicrobial effect while light-sensitive liquid is infused through the inner void 210 in the delivery catheter 101 and enters the inner cavity 295 of the expandable member 170.

Figure 11C:
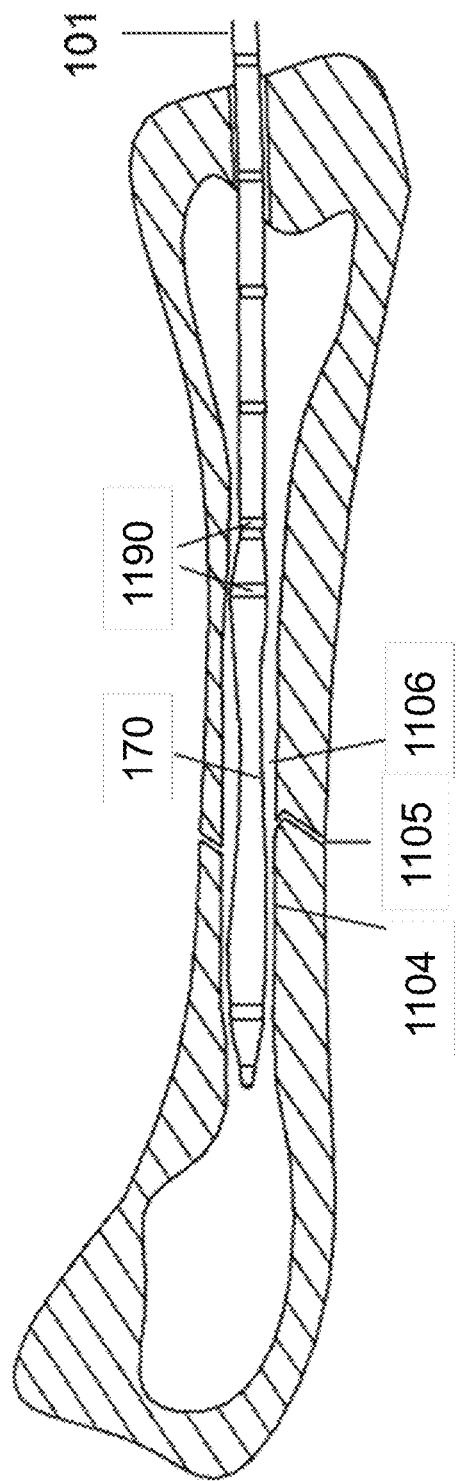

After the expandable member 170 is in the correct position within the fractured bone 1102, a delivery system which contains a light-sensitive liquid is attached to the port 195. The light-sensitive liquid is then infused through the inner void 210 in the delivery catheter 101 and enters the inner cavity 295 of the expandable member 170. This addition of the light-sensitive liquid within the expandable member 170 causes the expandable member 170 to expand, as shown in FIG. 11C. As the expandable member 170 is expanded, the fracture 1105 is reduced. Unlike traditional implants, such as rods, that span the fracture site, the expandable member 170 of the present disclosure does more than provide longitudinal strength to both sides of the fractured bone. In some embodiments, the expandable member 170 having the design can be a spacer for reducing the fracture and for holding the fractured and compressed bones apart at the point of the collapsed fracture.

Figure 11D:
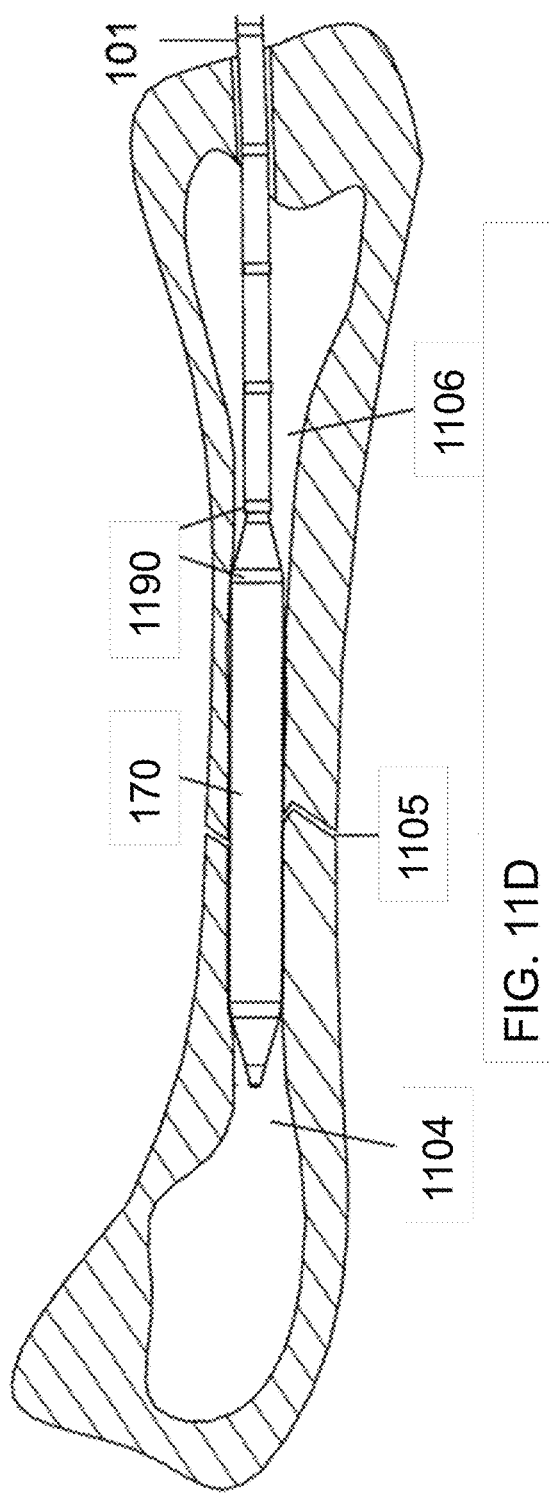

Once orientation of the bone fragments 1104 and 1106 are confirmed to be in a desired position, the light-sensitive liquid may be hardened within the expandable member 170, as shown in FIG. 11D, such as by illumination with a visible emitting light source. In some embodiments, during the curing step, a syringe housing a cooling media may be attached to the proximal end of the delivery catheter and continuously delivered to the expandable member 170. The cooling media can be collected by connecting tubing to the distal end of the inner lumen and collecting the cooling media via the second distal access hole. After the light-sensitive liquid has been hardened, the light source may be removed from the device. Alternatively, the light source may remain in the expandable member 170 to provide increased rigidity.

In some embodiments, subsequent illumination of the bone 1102 and surrounding tissue of the repair site can be performed after the expandable member 170 has been hardened. In some embodiments, where the light source has been removed from the expandable member 170, such subsequent illumination can be performed by reintroducing the light source into the hardened expandable member 170 and activating the light source. In some embodiments, where the light source has been removed from the expandable member 170, such subsequent illumination can be performed by positioning a light source adjacent to the hardened expandable member 170 and directing illumination into the expandable member 170 for distribution throughout the repair site. In some embodiments, where the light source remains in the expandable member 170 (e.g., to provide rigidity as discussed above), the light source can be reactivated to illuminate the repair site. In some embodiments, reactivation of the remaining light source can include reconnecting the light source to an external power or light generating device. In some embodiments, the remaining light source can include a power source (e.g., batteries) for remote activation as-needed. In some embodiments, the remaining light source can include inductive circuitry for example, for inductively activating the light source and/or for inductively charging batteries of the light source.

Figure 11E:
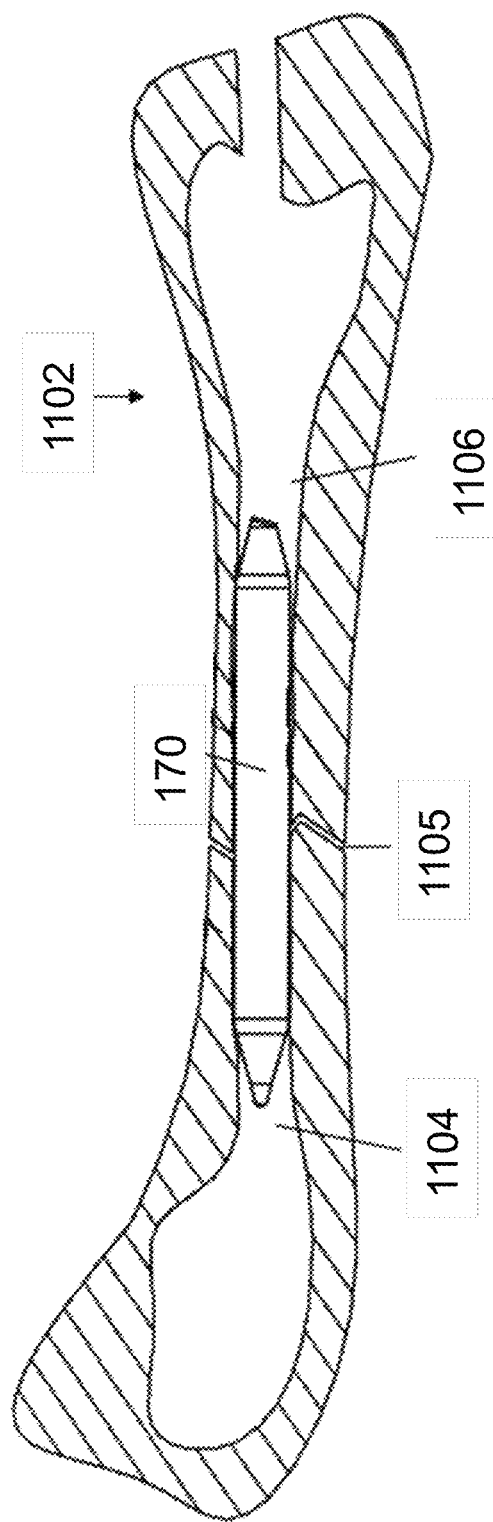

FIG. 11E shows at least one embodiment of a bone fixation device in a cavity of a bone after being separated from an introducer. For example, the expandable member 170 once hardened, may be released from the delivery catheter 101 to form a photodynamic bone fixation device inside the intramedullary cavity of the bone 1102. It is contemplated that optical fiber(s) may be passed in an inner lumen of the photodynamic bone fixation device, and optionally pass through a manifold located within the inner lumen and into a channel located in the photodynamic bone fixation device. Further, it is possible optical fiber(s) may be passed in a channel located within a ridge positioned on an outer surface of the photodynamic bone fixation device. Once the optical fiber(s) are positioned with the cavity of the bone, the optical fiber(s) may provide for an anti-microbial effect.

The following paragraphs provide experiments regarding the present disclosure relating to killing of orthopaedic relevant pathogens using blue light.

Overview

Figure 12:
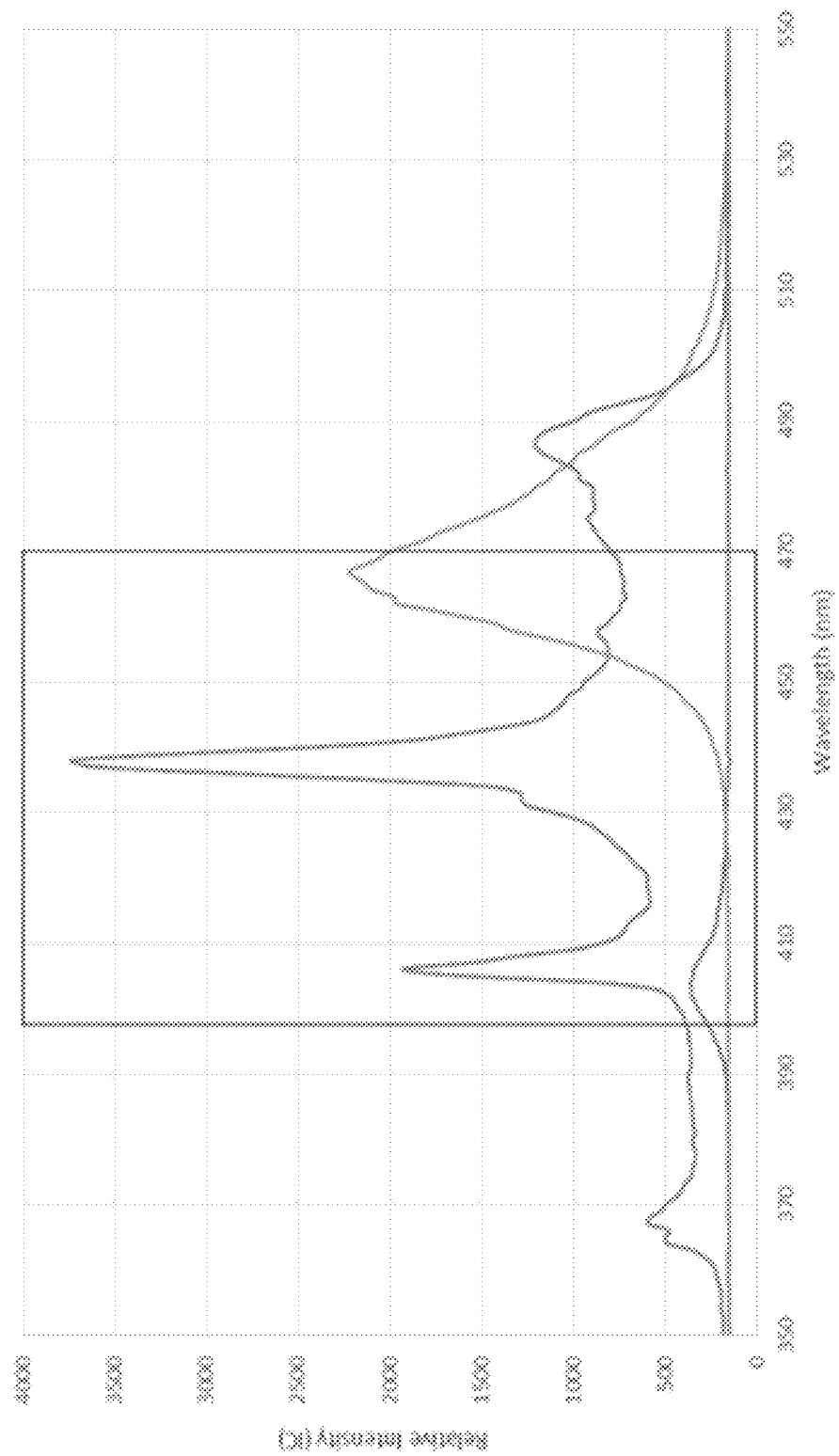
FIG. 12 illustrates the results of Experiment 1, that shows the output (Blue), positive control (405 nm—orange), positive control (470 nm—gray), wherein box area highlights the wavelengths of light (405 nm to 470 nm) that has shown to be antimicrobial against orthopaedic relevant bacteria. The blue light has a major peak in the region of 405 nm.

It is believed that blue light with wavelengths outside of the UV spectrum can have antimicrobial properties for both Gram-negative and Gram-positive bacteria. Currently, a clinical trial using blue light for photodynamic bone stabilization has begun, in accordance with aspects of the present disclosure. The question of whether the blue light used for photodynamic bone stabilization could kill orthopaedic relevant bacteria was asked because one of the major outputs from the optical fiber at 405 nm (see FIG. 12) has been shown to eradicate methicillin-resistant. FIG. 12 shows the output (Blue), positive control (405 nm—orange), positive control (470 nm—gray). The box area highlights the wavelengths of light (405 nm to 470 nm) that has shown to be antimicrobial against orthopaedic relevant bacteria. The blue light has a major peak in the region of 405 nm.

Null Hypothesis

Blue light is not capable of bactericidal activity against orthopaedic relevant bacteria because it does not have enough energy to be bacterial.

Objective

Using suspension cultures, we will test the following: (1) Does IlluminOss light kill MSSA and MRSA in a time dependent manner? (2) Does IlluminOss light kill patient isolated bacterial from orthopaedic infections? and (3) Does the IlluminOss implant have bactericidal activity during the time required for intra-operative polymerization (about 15 minutes)?

Significance

It is possible blue light may indicate that broad-spectrum antimicrobial effects that can be generated for both Gram-negative and Gram-positive bacteria. The antimicrobial effect may be due to bacteria intracellular porphyrins and the production of cytotoxic reactive oxygen molecules. Light in the visible spectrum may have the most effective wavelength for antimicrobial effects with the region of 402-420 nm, which appear to be most promising. It is encouraging that one of the major peaks for emission is in this blue light region (see FIG. 12). However, the blue light inactivation of bacteria may be dependent on dose. The dose of light needed to be bactericidal may be determined by an equation $E=Pt$, where E is in $J/cm^2$, P is in $mW/cm^2$ and t is time in seconds. It was determined from previous studies that a dose of 36 J/cm2 is toxic to bacteria but not harmful to mammalian cells.

Figure 13A:
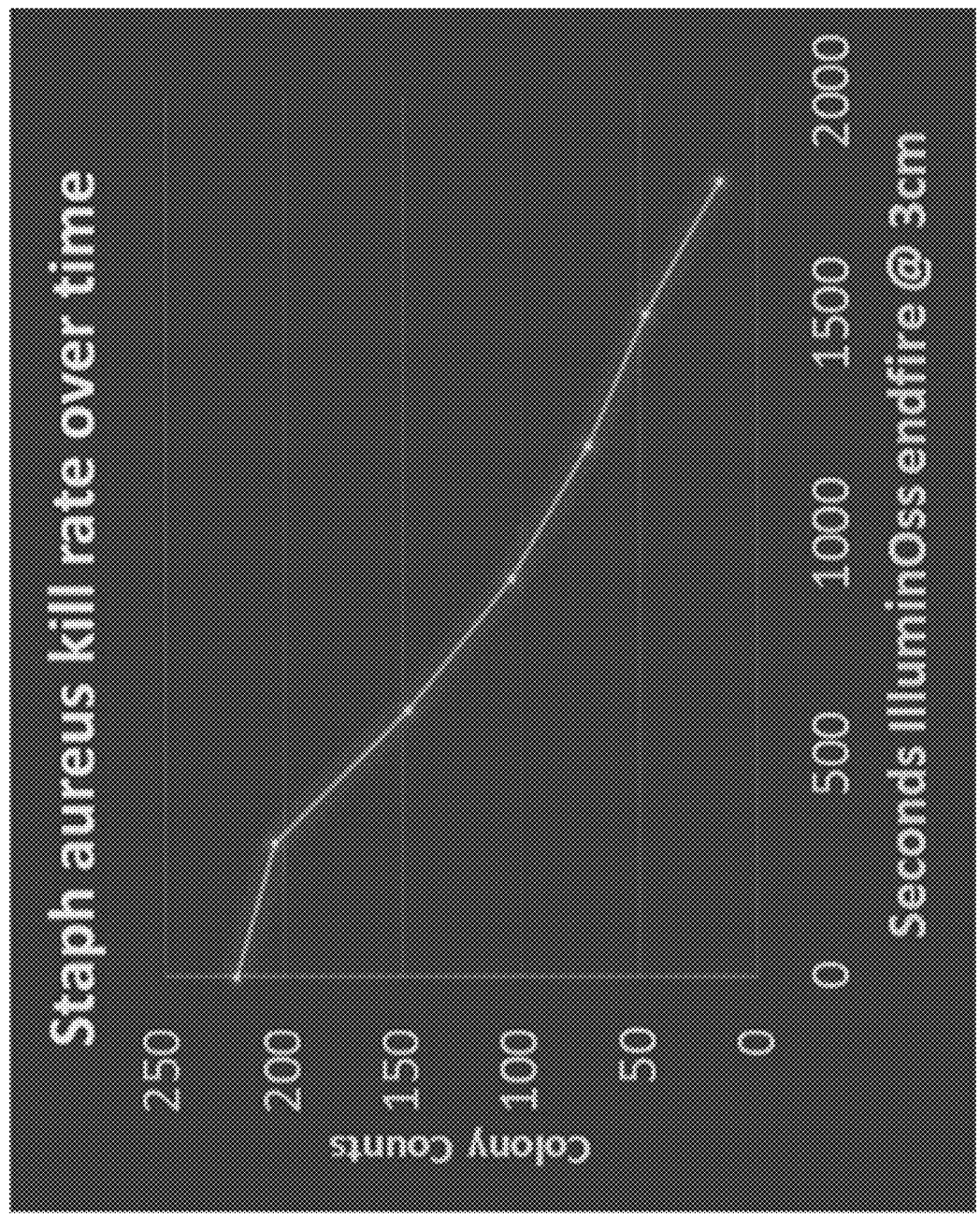
FIG. 13A and FIG. 13B illustrate the results of Experiment 1, that shows the initial suspension culture experiments were conducted demonstrating a time-dependent killing of MSSA with the light at energy levels that are not toxic to mammalian cells.
Figure 13B:
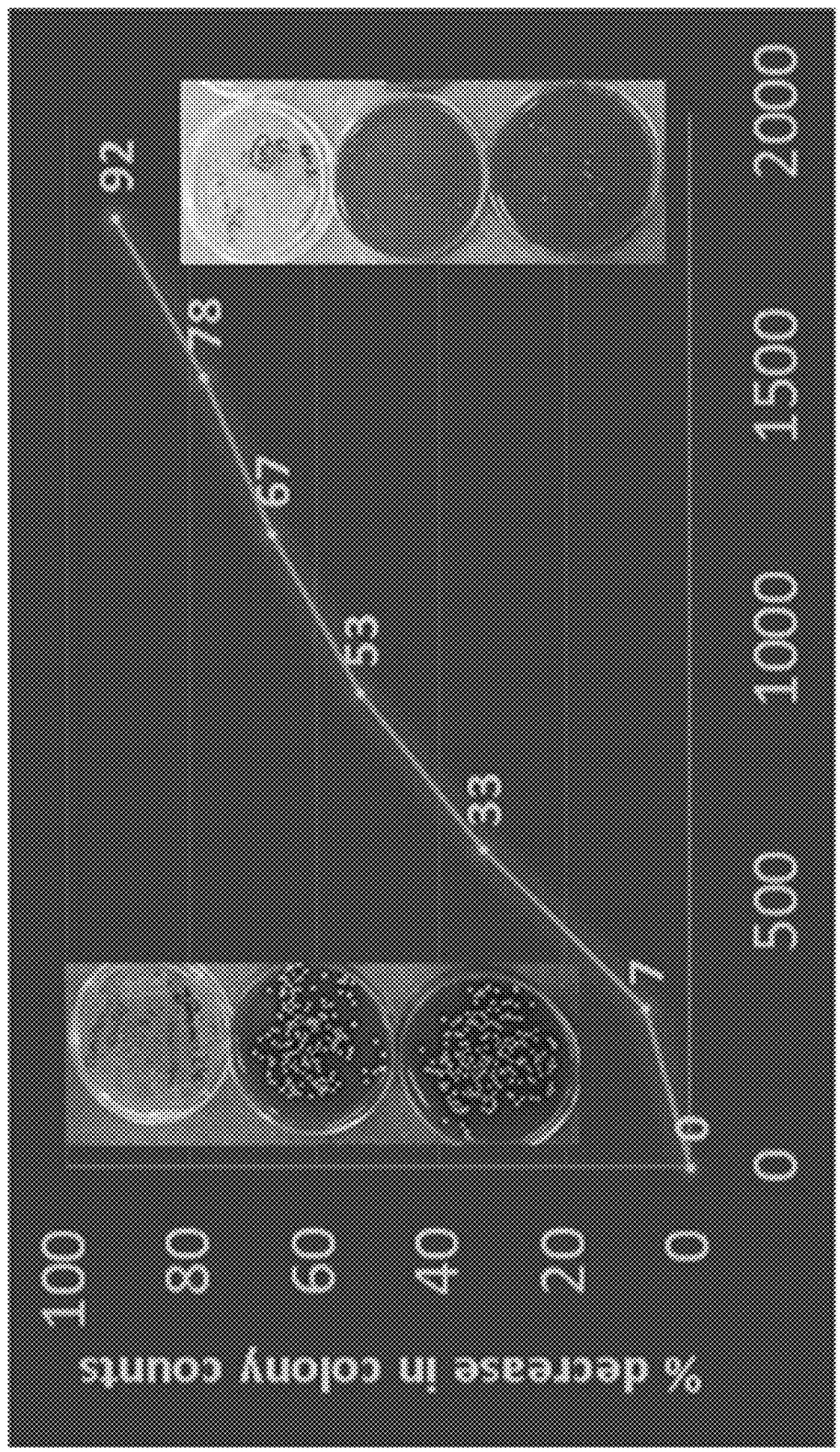

Initial suspension culture experiments were conducted demonstrating a time-dependent killing of MSSA with the light at energy levels that are not toxic to mammalian cells (see FIG. 13A and FIG. 13B). Further testing will allow for further characterization of this effect on patient isolated from orthopaedic infections and to test the potential bactericidal effect during a 15 minute implant curing process.

Research Design and Method

Suspension cultures have been used to determine the effect of blue light on bacterial inactivation. We have used this method to study the effect of IlluminOss blue light on MSSA ATCC 29213. The bacterial strain was diluted in 0.9% NSS until reaching an optical density of 0.5 McFarland units ($1.5 \times 10^8$ CFU/ml). Initial experiments were completed to determine the correct serial dilution in NSS to obtain about 200 colonies per 100 ul inoculum onto 100 mm blood agar plates (see FIG. 13A and FIG. 13B for colony counts). After final dilutions to a concentration that is relevant to cause orthopaedic related infections (around $10^5$), 3 ml of bacterial suspension was used for the light dosing experiments. A "end fire" fiber optic cable and R&D light box were included and then the intensity of light emitted from the end of the fiber optic cable to be 17.4 mW/cm$^2$ in the wavelengths from 395-415 nm was calculated. This "end fire" cable was used for the dosing experiments.

From a distance of 2 cm above the suspension culture surface the "end fire" IlluminOss light was delivered to the culture. 100 ul samples were taken after vortexing at 0, 5, 10, 15, 20, 25 and 30 minutes of continuous light treatment with duplicate experiments performed. The 100 ul bacterial suspension samples were streaked onto 100 mm blood agar plates and immediately placed into an incubator for 24 hrs at 37° C. at 5.5% $CO_2$. After 24 hrs the plates had colonies counted and data presented as % kill over time. Several controls were used including a 30 minute control of bacterial suspension in the 0.9% NSS with plating and colony counts that were not different from the 0 minute control indicating no effect of diluent over time. Additionally, since light generates heat the bacterial suspension cultures had direct temperature measurements. This did show that the suspensions increased from room temperature to 26.2° C. during the 30 minute treatment time indicating that the decrease in colony counts were not due to temperature effects. Initial experiments were done in a hospital microbiological laboratory.

It is noted the implant takes 15 minute for the polymerization step. It is therefore encouraging that the data in FIG. 13A and FIG. 13B indicate a bactericidal effect within this timeframe. The experiment showed to kill orthopaedic relevant bacteria.

Figure 14A:
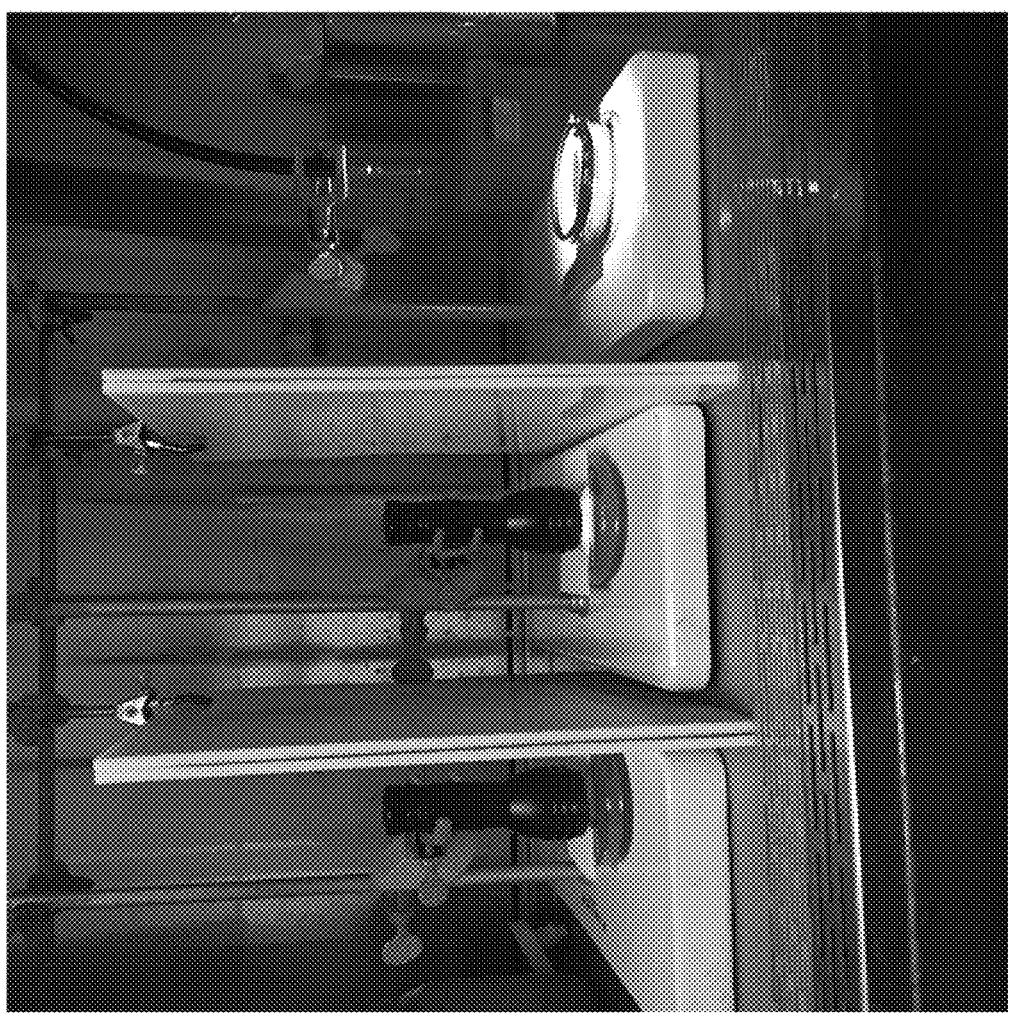
Figure 14D:
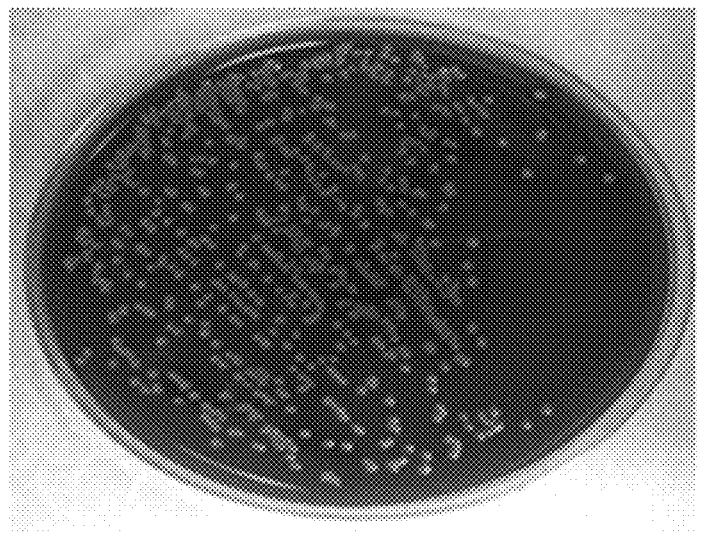
Figure 14C:
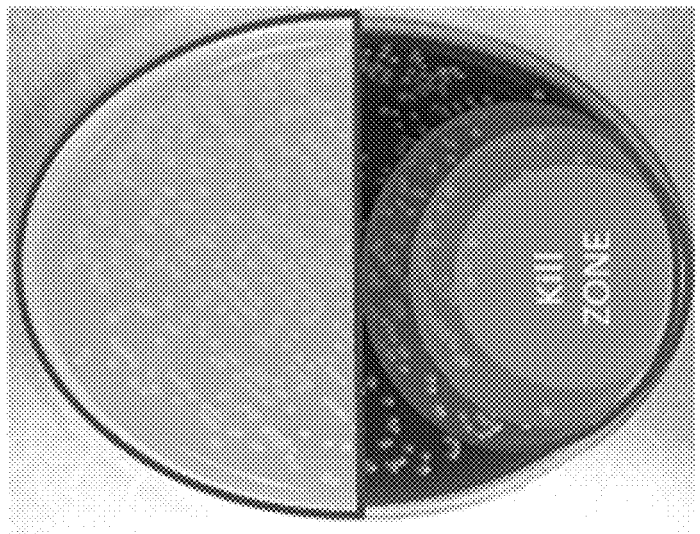
Figure 14B:
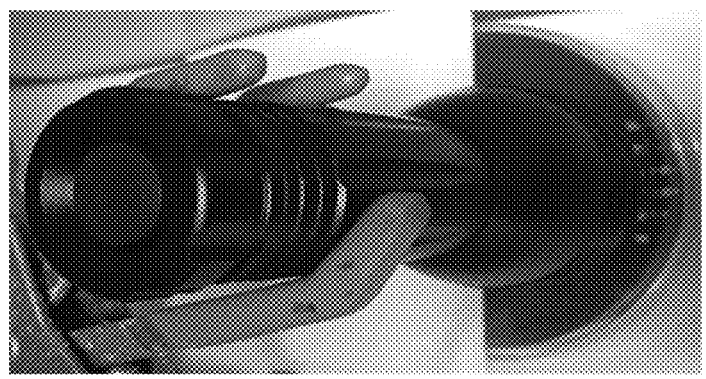
Figure 14E:
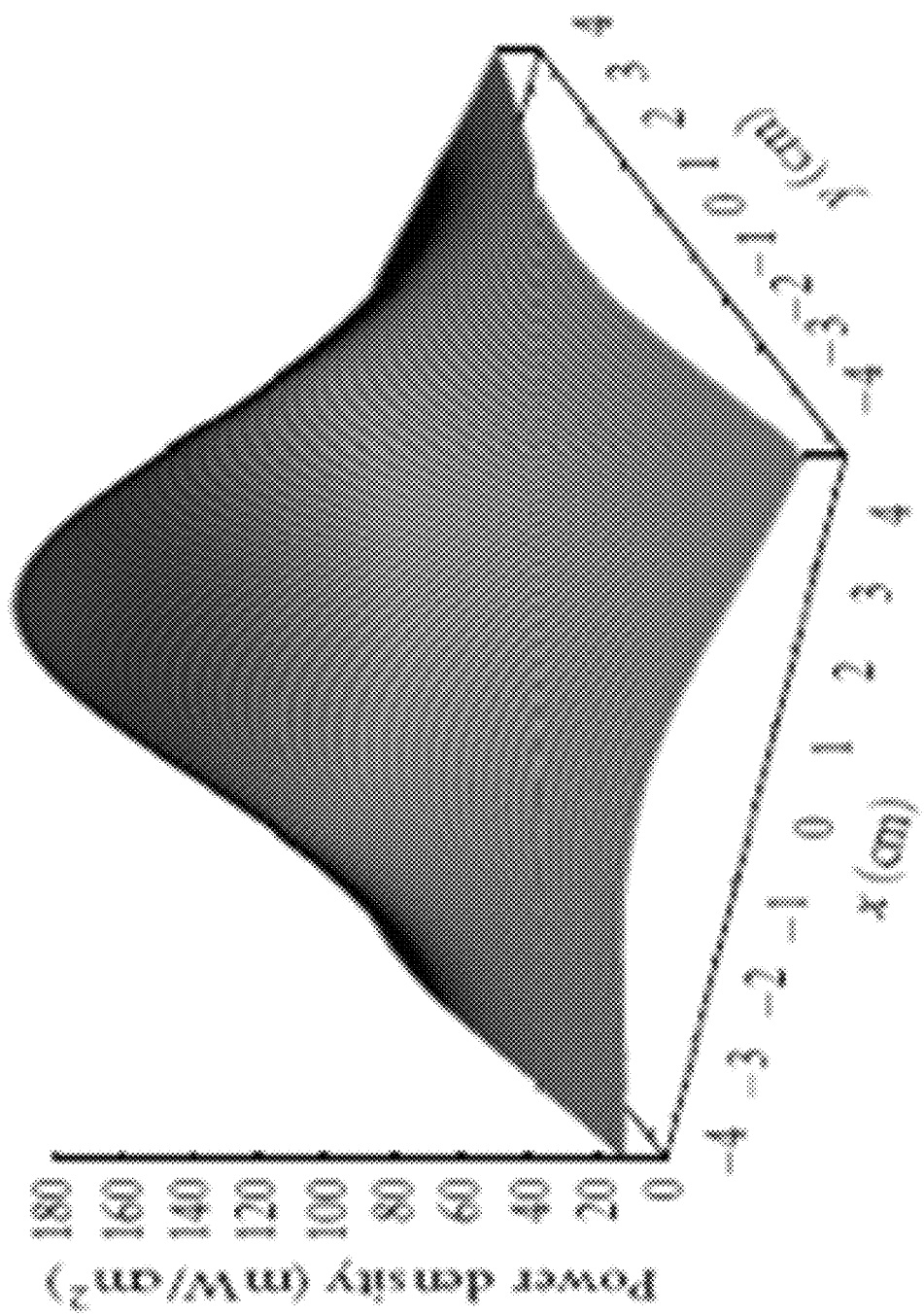
Figure 14F:
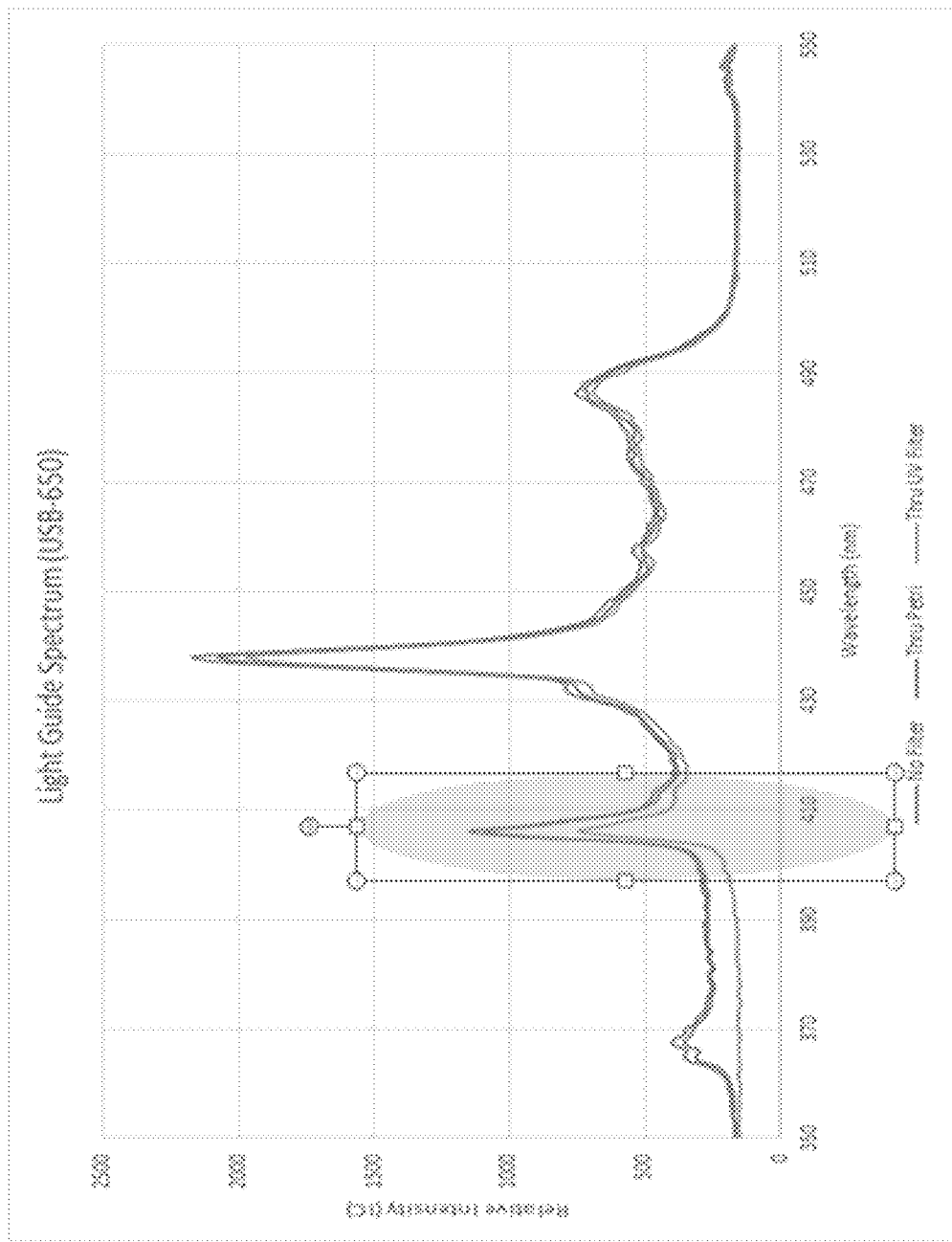

FIG. 14A, FIG. 14B, FIG. 14C, and FIG. 14D show the initial experimental set up. FIG. 14E indicates heat generation issues with change to optical fiber (POF). FIG. 14F indicates the identified wavelength via experimentation is about 405 nm. FIG. 14G indicates through results of experimentation that blue light works to have an anti-microbial effect on bones.

Figure 15B:
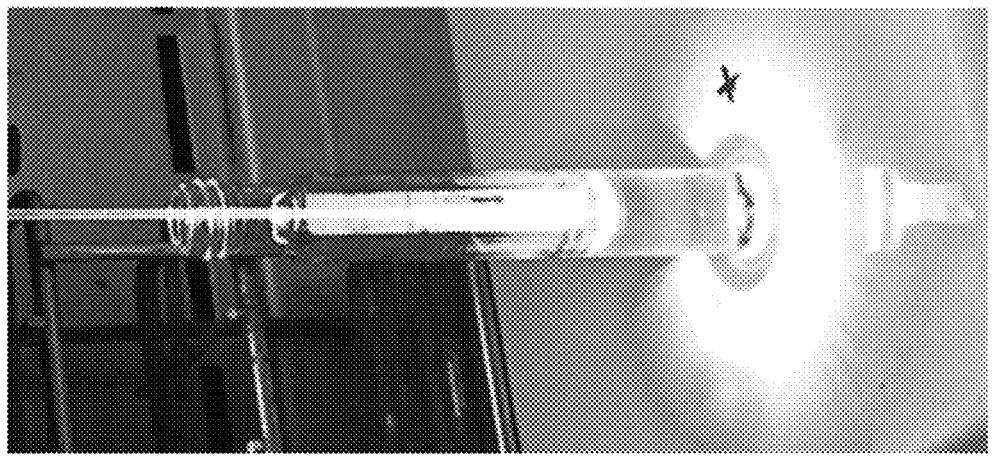
FIG. 15A, FIG. 15B, FIG. 15C, FIG. 15D, FIG. 15E, FIG. 15F, FIG. 15G, FIG. 15H, FIG. 15I, FIG. 15J, FIG. 15K, FIG. 15L, FIG. 15M, FIG. 15N, FIG. 15O, and FIG. 15P show the optical fiber (POF) experimental set up.
Figure 15A:
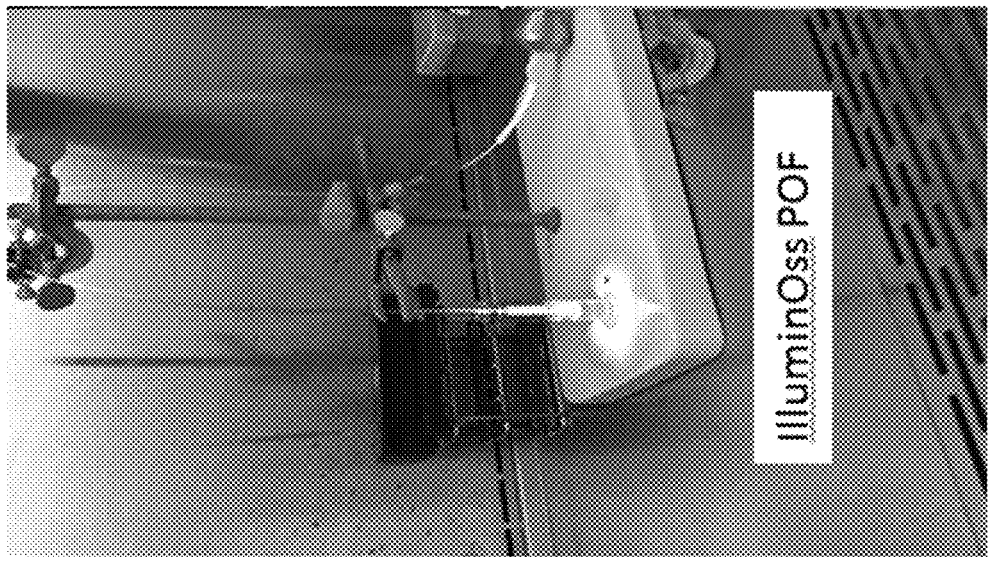
Figure 15C:
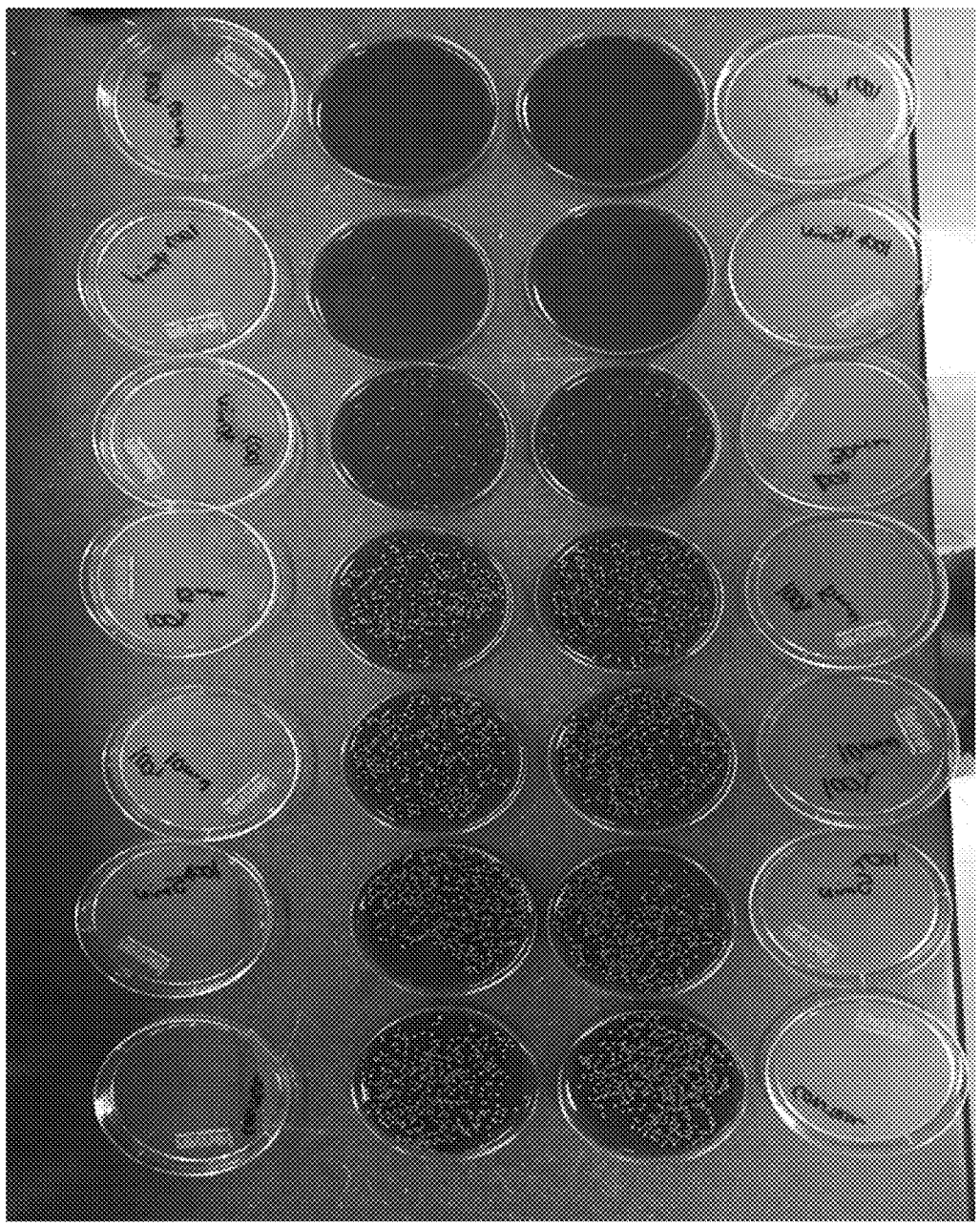
Figure 15D:
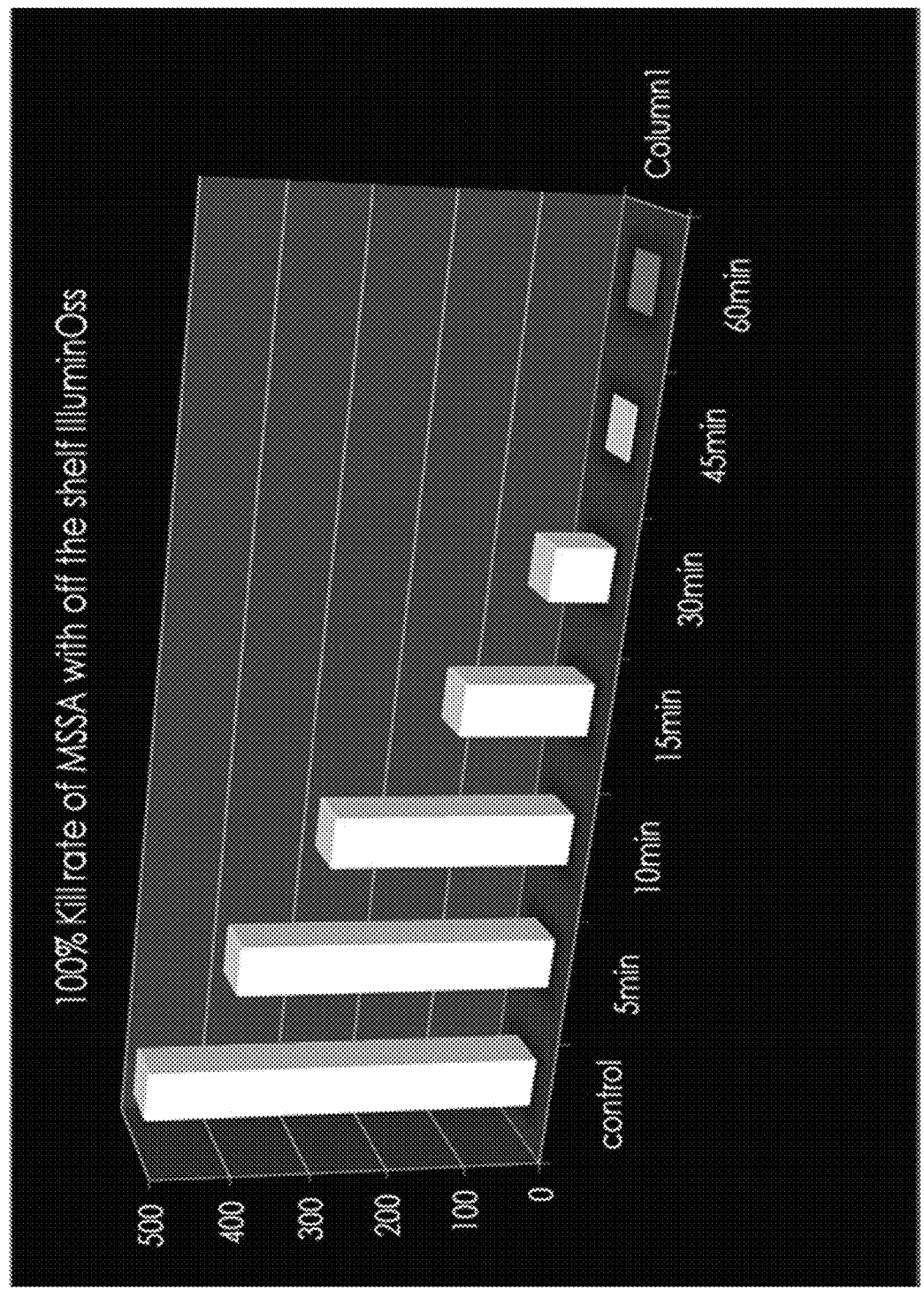

FIG. 15A, FIG. 15B, FIG. 15C, FIG. 15D, FIG. 15E, FIG. 15F, FIG. 15G, FIG. 15H, FIG. 15I, FIG. 15J, FIG. 15K, FIG. 15L, FIG. 15M, FIG. 15N, FIG. 15O, and FIG. 15P show the optical fiber (POF) experimental set up. FIG. 15A and FIG. 15B indicate the Oct. 18, 2015 trial that included: MISSA, ATCC29213, dilution in NSS, 3 cm distance from optical fiber (POF), 5, 10, 15, 30, 45 and 60 minute time. Plating over time of 100 ul, blood agar. FIG. 15C shows patient isolated cultures treated with blue light. FIG. 15D shows a graph resulting in a 100 percent kill rate of MSSA with a device.

Figure 15F:
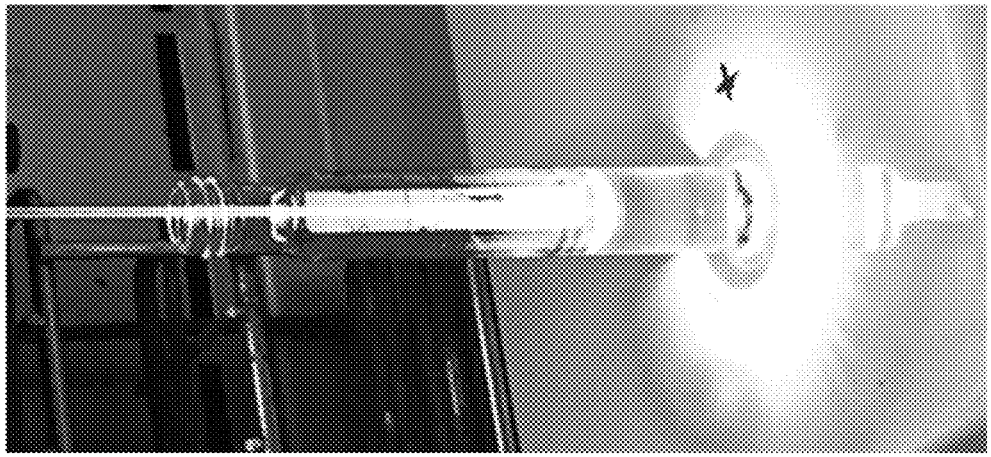
Figure 15E:
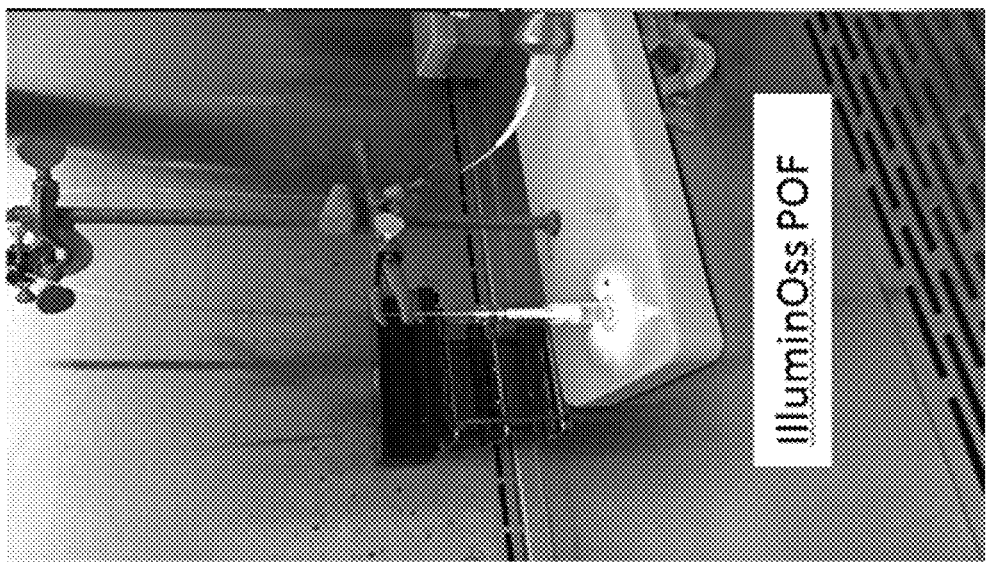
Figure 15G:
Figure 15I:
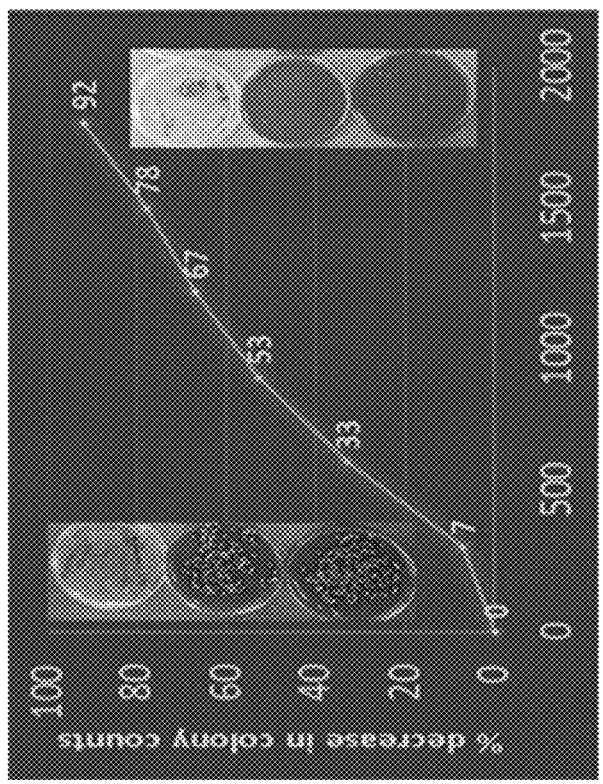
Figure 15H:
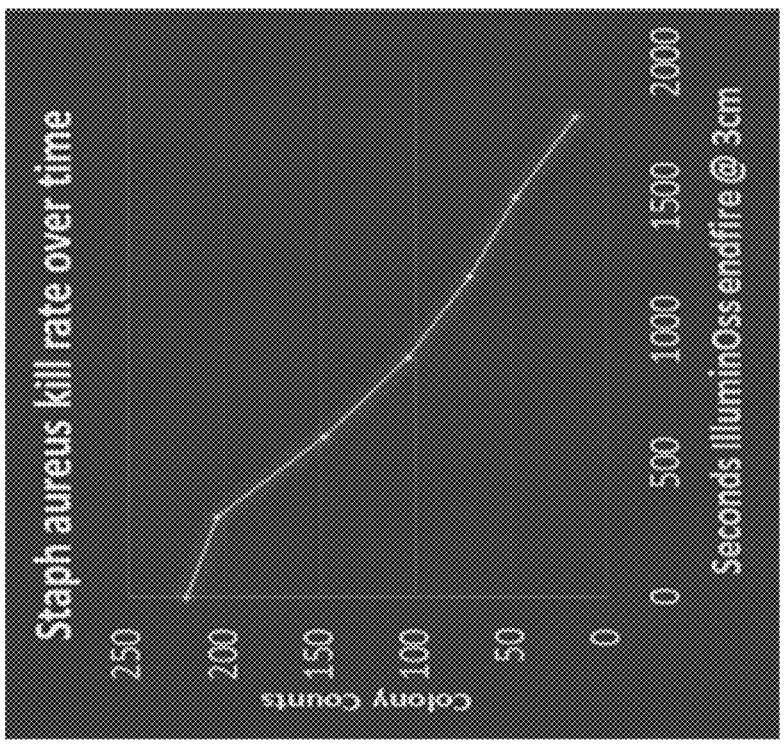
Figure 15J:
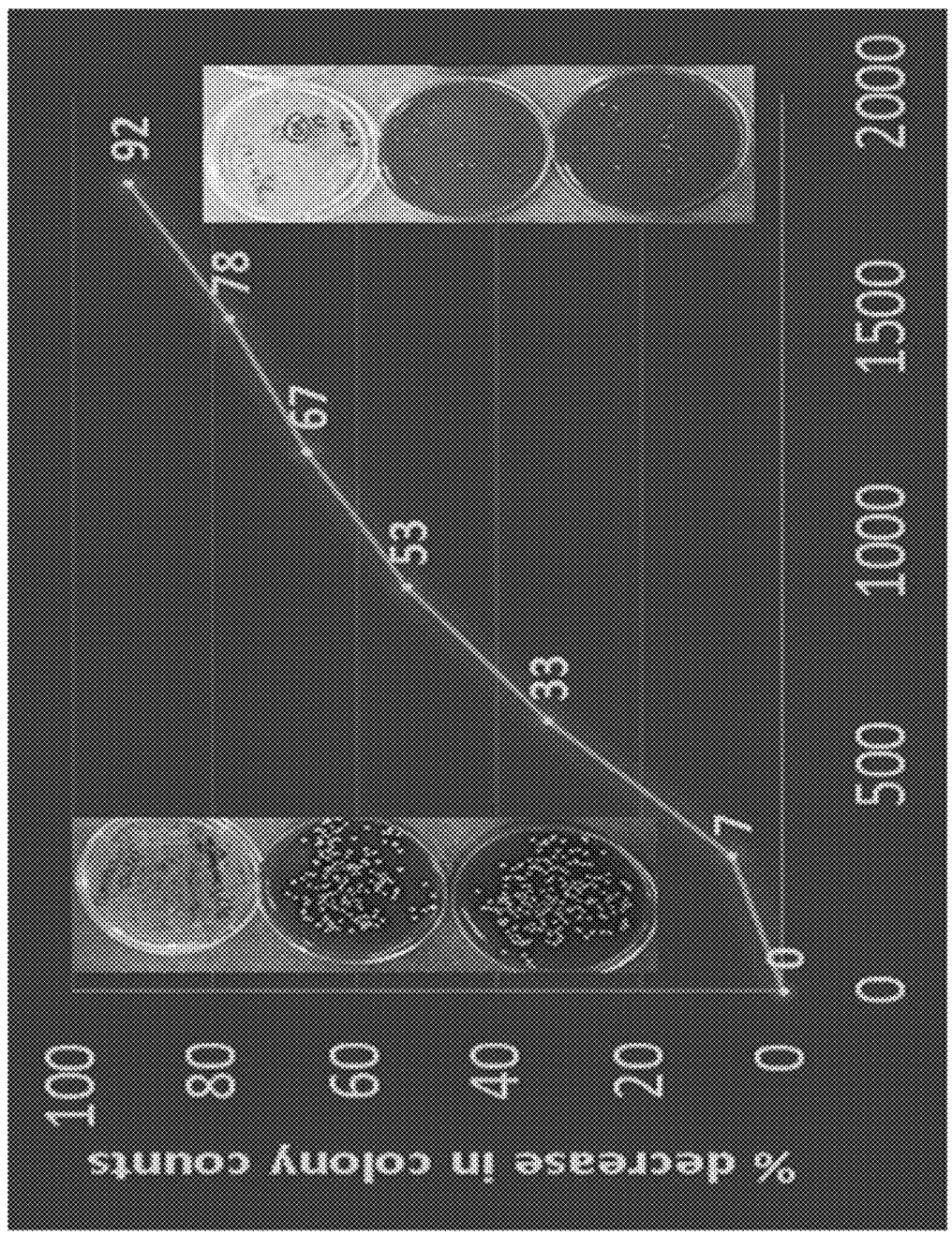

FIG. 15E and FIG. 15F indicate the Oct. 20, 2015 trial that included: MISSA, ATCC29213, dilution in NSS, 2 cm distance from the optical fiber (POF), 5, 10, 15, 20, 25 and 30 minute time. Plating over time of 100 ul, blood agar and additional control. FIG. 15G shows patient isolated cultures treated with blue light. FIG. 15H shows a graph resulting in a staph aureus kill rate over time. FIG. 15I and FIG. 15J show the percent decrease in colony counts versus time.

Figure 15L:
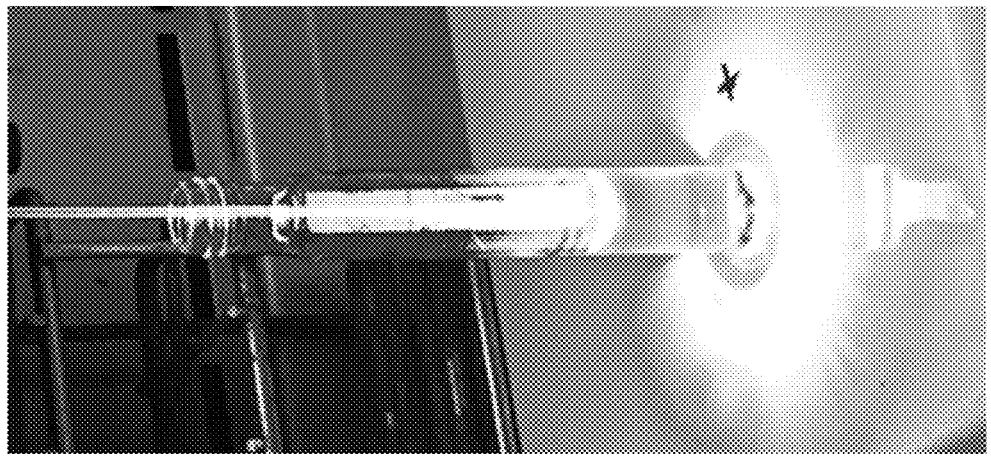
Figure 15K:
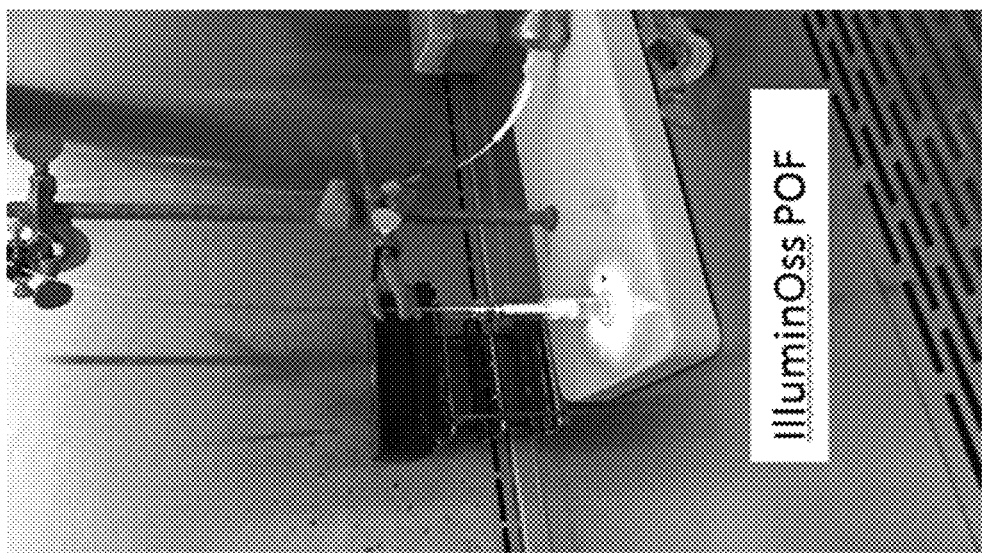
Figure 15M:
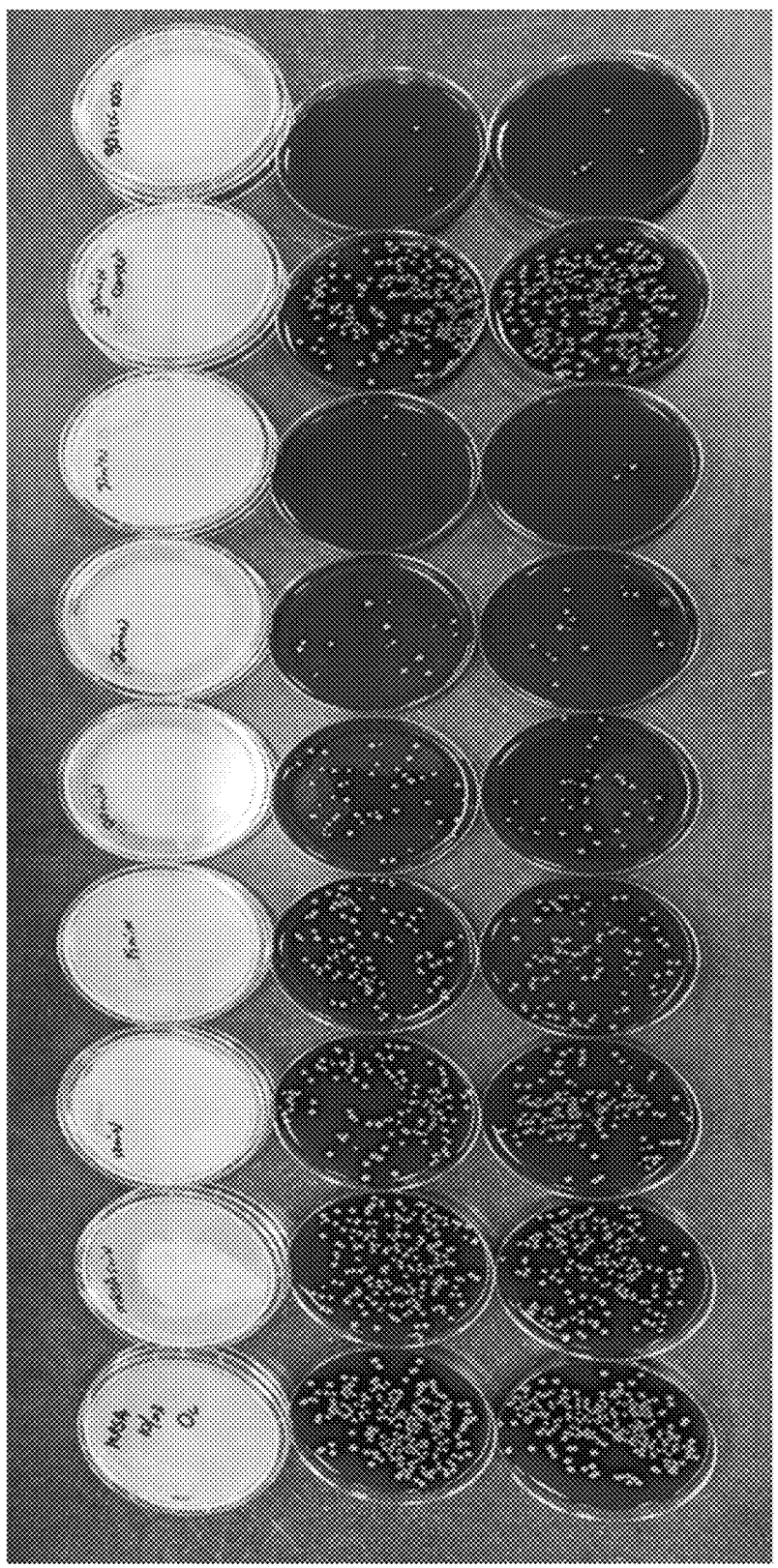
Figure 15O:
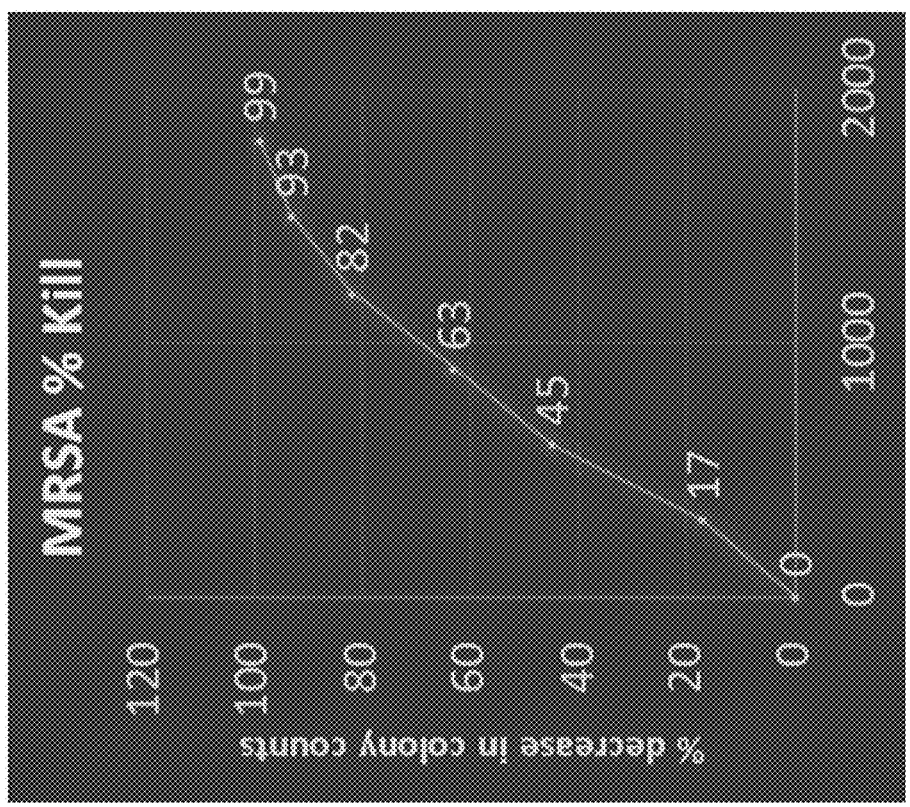
Figure 15N:
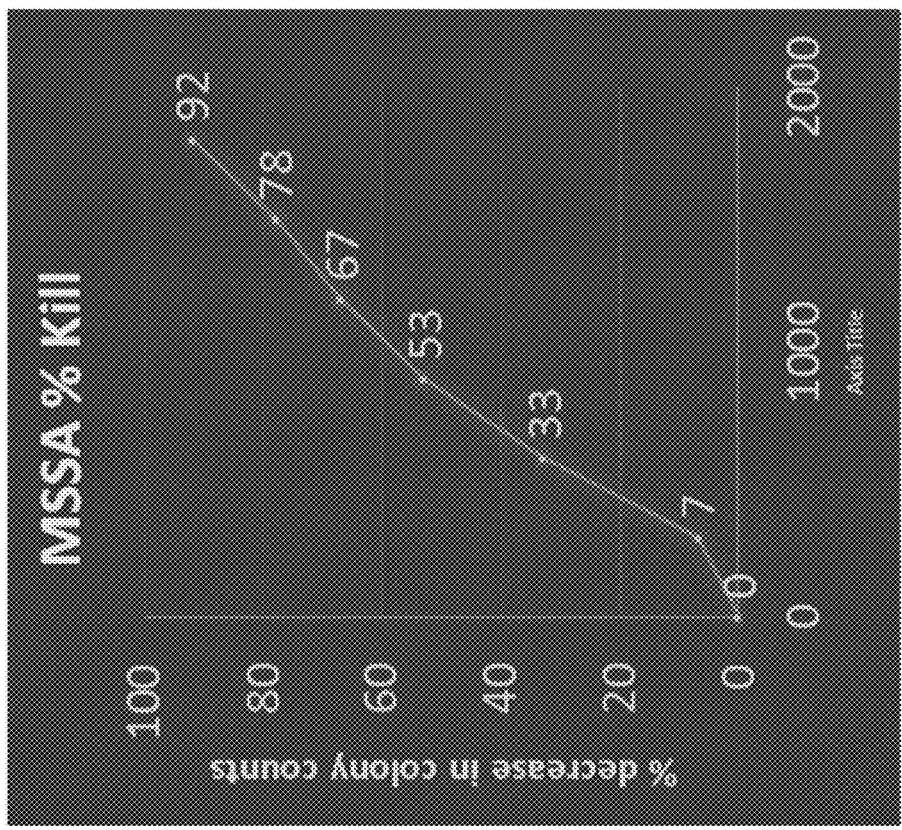
Figure 15P:
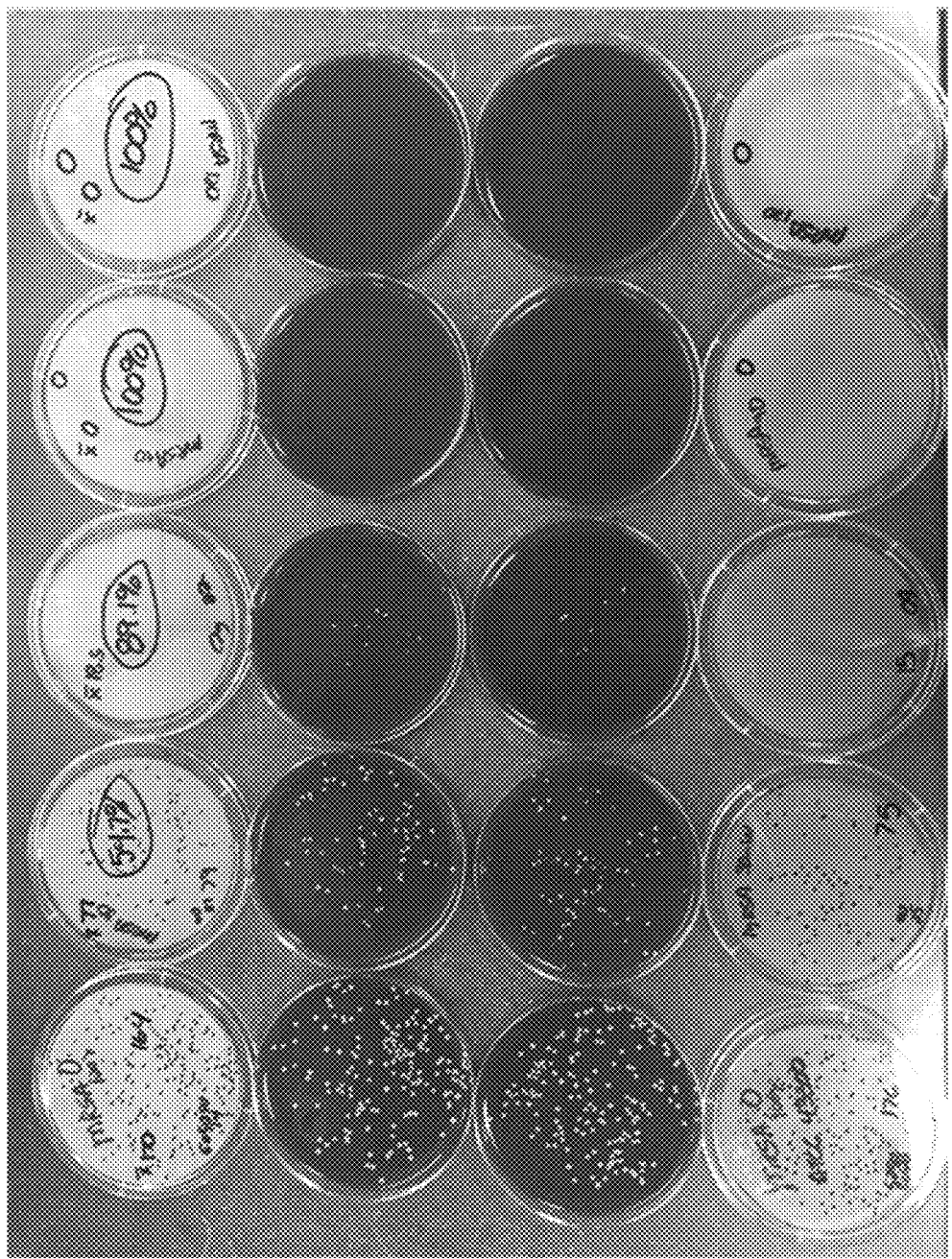

FIG. 15K and FIG. 15L indicate the Oct. 23, 2015 trial that included: Patient isolate MRSA, dilution in NSS, 2 cm distance from the optical fiber (POF), 5, 10, 15, 20, 25 and 30 minute time. Plating over time of 100 ul, blood agar and additional control. FIG. 15M shows patient isolated cultures treated with blue light. FIG. 15N and FIG. 15O indicate the optical fiber (POF) kills MSSA and MRSA. The POF experiment provided light delivered by the optical fiber (POF) that is bactericidal at clinically relevant times to clinically relevant bacteria. It is noted that completed experiments were in the "right" energy delivery in J/cm$^2$ at 405 nm. Finally, wound healing is NOT affected by blue light—(HINS light 5 mW/cm$^2$ for 1 hour no effect on fibroblast function). FIG. 15P shows patient isolated cultures treated with blue light.

Figure 16A:
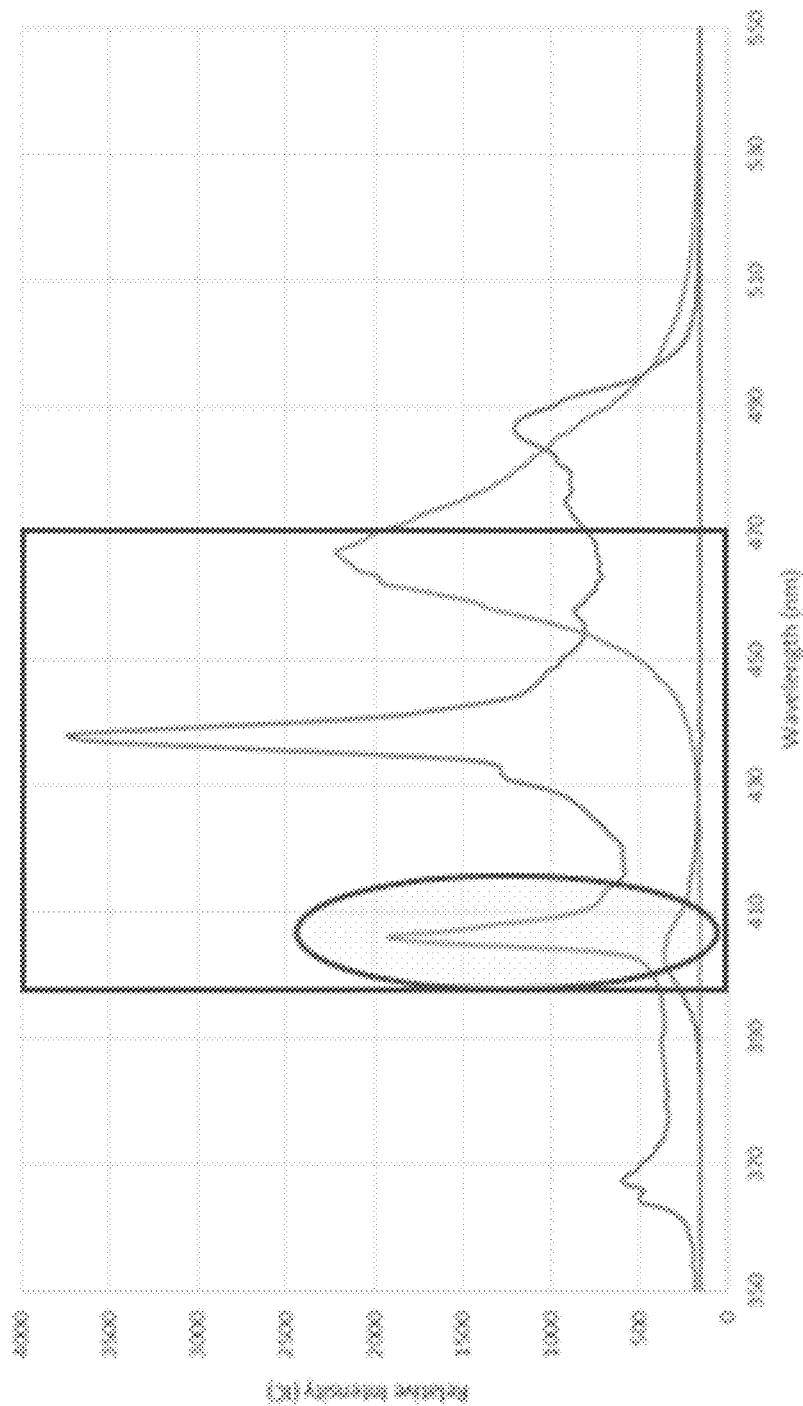
FIG. 16A is a graph that shows the spectral output from the fiber optic cable used in the device, according to embodiments of the disclosure.
Figure 16C:
FIG. 16B and FIG. 16C show the blue light output from the site of humeral biopsy, according to embodiments of the disclosure.
Figure 16B:

Referring to FIG. 16A, FIG. 16B and FIG. 16C show an intraoperative stabilization of a humerus fracture showing the blue light output. FIG. 16A is a graph that shows the spectral output from the fiberoptic cable used in the device. FIG. 16B and FIG. 16C show the blue light output from the site of humeral biopsy.

According to aspects of the disclosure, the use of blue light may kill MRSA, such that the blue light can provide sterilization of orthopaedically relevant pathogenic bacteria, among other things. For example, blue light, with wavelengths outside of the UV spectrum, can have antimicrobial properties for both Gram-negative and Gram-positive bacteria (using blue light for photodynamic bone stabilization, inventor's light fix clinical trial at Marshall University IRB 704603). It is possible, by non-limiting example this antimicrobial effect can be due to bacteria intracellular porphyrins and the production of cytotoxic reactive oxygen molecules, among other things.

Referring to FIG. 16A, the box area highlights the wavelengths of light (405-470 nm) in accordance with aspects of the disclosure. In particular, the wavelengths of light (405-470 nm) show it is possible for antimicrobial effects against orthopaedic relevant bacteria. Further, one of the blue light outputs from the optical fiber at 405 nm (see FIG. 16A, blue peak in yellow oval), show that this wavelength can eradicate methicillin-resistant *S. aureus* (MRSA), *S. aureus* and *P. aeruginosa* in a time and dose dependent manner due to the production of cytotoxic reactive oxygen molecules. Further, according to aspects of the disclosure, it is determined that the full spectrum light output during the 400 second implant curing process is capable of bactericidal activity to orthopaedically relevant pathogens.

Figures 17A, 17B:
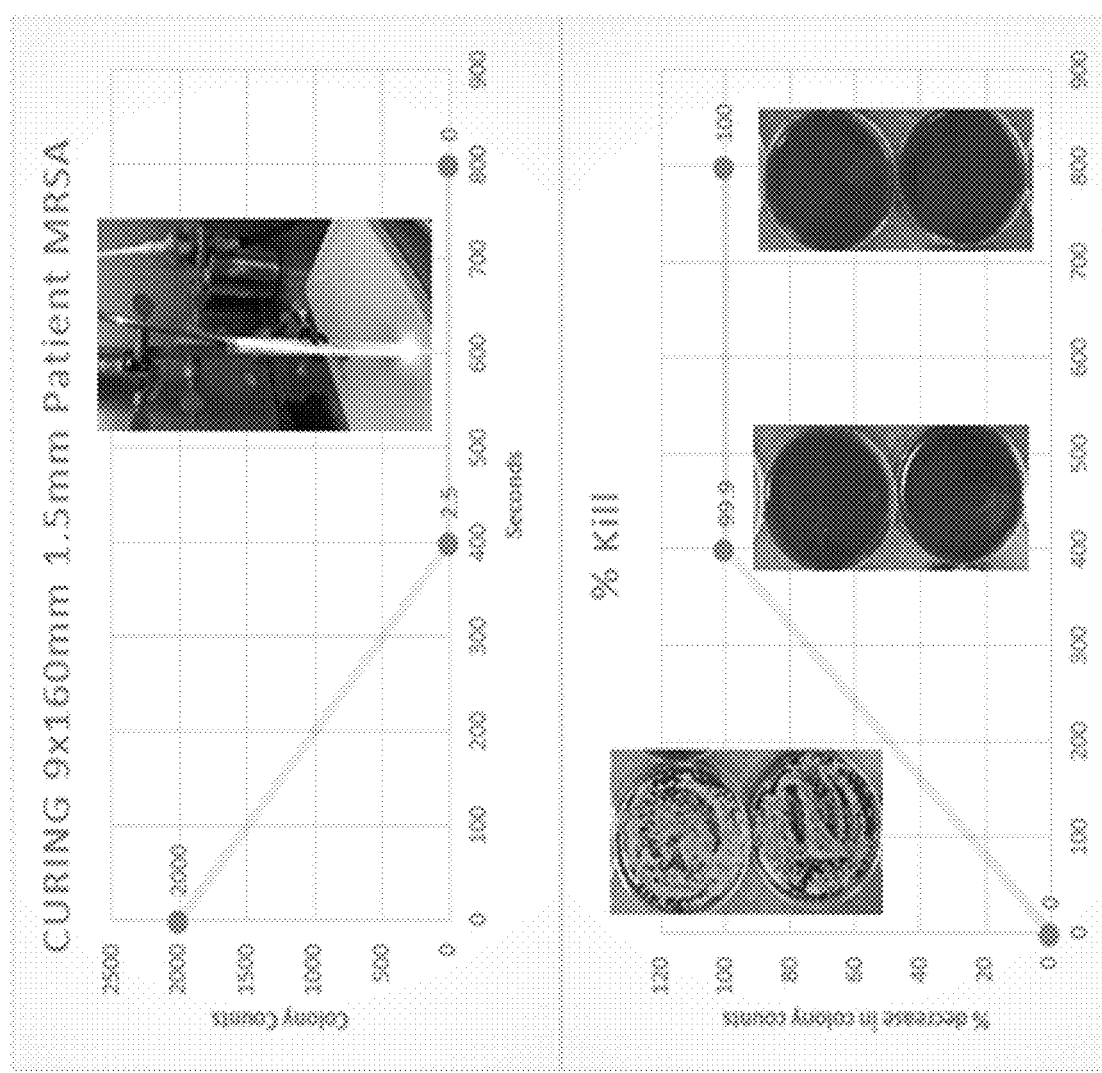
FIG. 17A shows a graph of the number of the patient isolated MRSA culture counts versus time in seconds curing with the blue light, according to embodiments of the disclosure
FIG. 17B shows the percent decrease in colony counts versus time in seconds curing with the blue light, according to embodiments of the disclosure.

FIG. 17A and FIG. 17B show patient isolated MRSA suspension cultures treated with blue light from an implant 9×160 mm with curing occurring at 400 seconds. FIG. 17A shows a graph of the number of the patient isolated MRSA culture counts versus time in seconds curing with the blue light. FIG. 17B shows the percent decrease in colony counts versus time in seconds curing with the blue light. FIG. 17A (top) and FIG. 17B (bottom) illustrates that 99.9% of bacteria is killed during the 400 seconds curing of the implant. Wherein an the additional time point at 800 seconds shows 100% inactivation of MRSA.

FIG. 17A shows time dependent inactivation of MRSA (samples taken at every 400 seconds) seen after plating 100 ul onto 100 mm blood agar plates and incubating for 24 hrs at 37° C. at 5.5% $CO_2$. FIG. 17B shows 99.9% of bacteria killed during the 400 seconds curing of the implant. An additional time point at 800 seconds is shown with 100% inactivation of MRSA. It is noted that temperature measurements were never above 26.2° C. indicating no bacterial inactivation due to heat.

According to methods of the disclosure, blue light inactivation of bacteria can be dependent on amount or dose of light as described by the equation:

$$\text{Energy (J/cm2)} = \text{Intensity (W/cm2)} \times \text{time (seconds)}$$

Wherein, it is noted that a dose of 36 J/cm2 is toxic to bacteria but not harmful to mammalian cells. It is possible to use suspension cultures to determine the effect of blue light on bacterial inactivation, wherein this method was used to study the effect of blue light on control bacteria, i.e. MSSA (ATCC 29213) and MRSA (ATCC 43300). Further, according to aspects of the disclosure the bacterial strain was diluted in 0.9% NSS until reaching an optical density of approximately 0.5 McFarland units ($1.5 \times 10^8$ CFU/ml). Initial experiments were completed to determine a correct serial dilution in NSS to obtain about 200 colonies per 100 ul inoculum onto 100 mm blood agar plates. After final dilutions to a concentration that is relevant to cause orthopaedic related infections (around $10^5$), 3 ml of bacterial suspension was used for the light dosing experiments. A time-depending bacterial killing was noted in these control experiments (data not shown). These suspension culture experiments were repeated in duplicate for patient isolated MRSA and data shown in FIG. 17A and FIG. 17B. FIG. 17B shows that a 99.9% killing of MRSA was obtained in 400 seconds used for curing at energy levels that are not toxic to mammalian cells.

According to aspects of methods and embodiments of the disclosure, MRSA is 99.9% inactivated during the 400 seconds cure for the disclosed implant. It is noted that the aspects of the disclosure of bactericidal activity associated with an Orthopaedic Implant that is not due to the intrinsic material properties of the implant. According to aspects of the disclosure, it is contemplated that the effectiveness of implant on bacterial pathogens most commonly causing Orthopaedically relevant infections can be a way to minimize or manage surgical site infections. It is possible aspects of the disclosure can be used for decontamination of wounds, implants, infected bone and environmental and biologically contaminated surfaces, among other things.

All patents, patent applications, and published references cited herein are hereby incorporated by reference in their entirety. It will be appreciated that several of the above-disclosed and other features and functions, or alternatives thereof, may be desirably combined into many other different systems or applications.

What is claimed is:

1. A system for providing an anti-microbial effect on a bone comprising:
    a delivery catheter having an elongated shaft with a proximal end, a distal end, and a longitudinal axis therebetween, an inner void for passing at least one light sensitive liquid, and an inner lumen;
    an expandable member releasably engaging the distal end of the delivery catheter, the expandable member being configured to be placed into a space within a bone and capable of moving from a deflated state to an inflated state by infusing the at least one light sensitive liquid into the expandable member
    at least one ridge disposed on the outer surface of the expandable member, the at least one ridge shaped longitudinally along the expandable member and extending from a first end to a second end of the expandable member;
    a light conducting fiber sized to pass through the inner lumen of the delivery catheter; and
    at least one channel defined in each of the at least one ridge, the at least one channel sized to accept the light conducting fiber.

2. The system of claim 1, wherein the at least one ridge is a plurality of ridges and each of the plurality of ridges includes at least one channel.

3. The system of claim 2, wherein, when the light conducting fiber is in the at least one channel of the plurality of ridges, the light conducting fiber is configured to disperse light energy to provide the anti-microbial effect, prior to infusing the at least one light sensitive liquid in the expandable member.

4. The system of claim 1, wherein the expandable member is designed to be at least partially placed into the space within the bone.

5. The system of claim 1, wherein the light conducting fiber is able to disperse light energy to provide the anti-microbial effect prior to infusing the at least one light sensitive liquid in the expandable member.

6. The system of claim 1, wherein the at least one light sensitive liquid is passed in and out of the expandable member to form fit the expandable member to a surface contact area within the space of the bone.

7. The system of claim 1, wherein an amount of the light sensitive liquid is hardened within the expandable member, such that a size and a shape of the formed photodynamic implant has a size and a shape of the space inside the bone, so the bone is restructured to a substantially original size and an original shape around the formed photodynamic implant.

8. The system of claim 1, wherein the dispersion of light energy to provide the anti-microbial effect is about 400 seconds, less than 400 seconds, or about 400 seconds to about 800 seconds.

9. A system for providing an anti-microbial effect on a bone comprising:
    a delivery catheter having an elongated shaft with a proximal end, a distal end, and a longitudinal axis therebetween, an inner void for passing at least one light sensitive liquid, and an inner lumen;
    an expandable member releasably engaging the distal end of the delivery catheter, the expandable member is being configured to be placed into a space within a bone and having an outer surface and an inner surface, wherein the inner surface defines a cavity, the expandable member movable from a deflated state to an inflated state when the at least one light sensitive liquid is passed into the cavity of the expandable member;
    at least one ridge disposed on the outer surface of the expandable member, the at least one ridge shaped longitudinally along the expandable member and extending from a first end to a second end of the expandable member;
    a light conducting fiber sized to pass through the inner lumen of the delivery catheter; and
    one or more channel defined in each of the at least one ridge, the one or more channel sized to accept the light conducting fiber.

10. The system of claim 9, wherein the expandable member is designed to be at least partially placed into the space within the bone, directly in contact with the bone and to form fit to a surface contact area within the space of the bone.

11. The system of claim 9, wherein an amount of the light sensitive liquid is hardened within the expandable member, such that a size and a shape of the formed photodynamic implant has a size and a shape of the space inside the bone, so the bone is restructured to a substantially original size and an original shape around the formed photodynamic implant.

* * * * *